US011440892B2

(12) United States Patent
Scheidt et al.

(10) Patent No.: US 11,440,892 B2
(45) Date of Patent: Sep. 13, 2022

(54) SUBSTITUTED DIHYDROBENZOXAZINONES, DIHYDROQUINOLONES, AND METHODS OF THEIR USE AND SYNTHESIS

(71) Applicant: Northwestern University, Evanston, IL (US)

(72) Inventors: Karl A. Scheidt, Evanston, IL (US); Ansoo Lee, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 16/920,566

(22) Filed: Jul. 3, 2020

(65) Prior Publication Data
US 2021/0024473 A1    Jan. 28, 2021

Related U.S. Application Data

(60) Provisional application No. 62/870,516, filed on Jul. 3, 2019.

(51) Int. Cl.
| | | |
|---|---|---|
| C07D 265/22 | (2006.01) | |
| C07D 413/04 | (2006.01) | |
| C07D 265/16 | (2006.01) | |
| C07D 215/233 | (2006.01) | |

(52) U.S. Cl.
CPC ....... *C07D 265/22* (2013.01); *C07D 215/233* (2013.01); *C07D 265/16* (2013.01); *C07D 413/04* (2013.01); *C07B 2200/07* (2013.01)

(58) Field of Classification Search
CPC .............. C07D 265/22; C07D 215/233; C07D 265/16; C07D 413/04
See application file for complete search history.

(56) References Cited

U.S. PATENT DOCUMENTS

| | | | |
|---|---|---|---|
| 4,894,374 A | 1/1990 | Skotnicki | |
| 7,851,640 B2 | 12/2010 | Scheidt | |
| 8,912,341 B2 | 12/2014 | Scheidt | |
| 9,090,634 B2 | 7/2015 | Scheidt | |
| 9,260,564 B2 | 2/2016 | Lombardo | |
| 9,309,217 B2 | 4/2016 | Scheidt | |
| 9,334,297 B2 | 5/2016 | Scheidt | |
| 9,512,146 B2 | 12/2016 | Scheidt | |
| 9,527,812 B2 | 12/2016 | Scheidt | |
| 9,624,190 B2 | 4/2017 | Scheidt | |
| 9,643,947 B2 | 5/2017 | Scheidt | |
| 9,839,625 B2 | 12/2017 | Bergan | |
| 9,840,487 B2 | 12/2017 | Scheidt | |
| 9,981,968 B2 | 5/2018 | Schiltz | |
| 10,231,949 B2 | 3/2019 | Bergan | |
| 10,308,624 B2 | 6/2019 | Scheidt | |
| 10,323,039 B2 | 6/2019 | Scheidt | |
| 10,654,865 B2 | 5/2020 | Scheidt | |
| 10,780,076 B2 | 9/2020 | Bergan | |
| 10,781,172 B2 | 9/2020 | Scheidt | |
| 2014/0206886 A1 | 7/2014 | Scheidt | |
| 2015/0065703 A1 | 3/2015 | Scheidt | |
| 2016/0002252 A1 | 1/2016 | Schiltz | |
| 2019/0276458 A1 | 9/2019 | Schiltz | |
| 2020/0181106 A1 | 6/2020 | Scheidt | |
| 2020/0399241 A1 | 12/2020 | Scheidt | |
| 2021/0009547 A1 | 1/2021 | Scheidt | |
| 2021/0009603 A1 | 1/2021 | Scheidt | |

FOREIGN PATENT DOCUMENTS

WO    2009108392 A2    9/2009

OTHER PUBLICATIONS

Castaing; Angew. Chem. Int. Ed. 2013, 52, 13280-13283. (Year: 2013).*
Cheong; Tetrahedron 2008, 64, 2329-2338. (Year: 2008).*
Hems; Tetrahedron Letters 1969, 5, 375-378. (Year: 1969).*
Lee; Angew.Chem. Int.Ed. 2019, 58,5941-5945. With Supporting Information. 115 pages. (Year: 2019).*
Macias; Nat. Prod. Rep. 2009, 26, 478-489. (Year: 2009).*
Powers; Chem. Rev. 2002, 102, 12, 4639-4750. (Year: 2002).*
Yamaguchi; Tetrahedron Letters 2017, 58, 4043-4047. (Year: 2017).*
Yoshida; J. Am. Chem. Soc. 2006, 128, 34, 11040-11041. (Year: 2006).*
Pisaneschi; Synlett 2011, 241-244. First Page and Supporting Information, 16 pages. (Year: 2011).*
Wright; Helvetica Chimica Acta 2012, 95, 2446-2459. (Year: 2012).*
Beutner, G. L., et al. "A practical method for preparation of 4-hydroxyquinolinone esters." The Journal of organic chemistry 72.18 (2007): 7058-7061.
Borrego, L. G., et al. "An Efficient and Practical Method for the Enantioselective Synthesis of Tertiary Trifluoromethyl Carbinols." Advanced Synthesis & Catalysis 360.6 (2018): 1273-1279.
Bose, D. S. et al. "First total synthesis of (-)-circumdatin H, a novel mitochondrial NADH oxidase inhibitor." Synthesis Apr. 2010 (2010): 643-650.
Chen, D-F, et al. "N-heterocyclic carbene and chiral Brønsted acid cooperative catalysis for a highly enantioselective [4+2] annulation." Synthesis 49.2 (2017): 293.
Chen, S., et al. "Arylketone p-Conjugation Controls Enantioselectivity in Asymmetric Alkynylations Catalyzed by Centrochiral Ruthenium Complexes." Journal of the American Chemical Society 140.15 (2018): 5146-5152.
Chen, X., et al. "Functionalization of Benzylic C (sp3) AH Bonds of Heteroaryl Aldehydes through N-Heterocyclic Carbene Organocatalysis." Angewandte Chemie International Edition 52.42 (2013): 11134-11137.

(Continued)

*Primary Examiner* — Daniel R Carcanague
(74) *Attorney, Agent, or Firm* — Quarles & Brady LLP

(57) ABSTRACT

Disclosed are dihydrobenzoxazinone compounds, dihydroquinolone compounds, and methods of their synthesis. The disclosed compounds may be prepared by reacting a benzoxazinedione compound and a ketone compound in the presence of an N-heterocyclic carbine (NHC) catalyst to perform a NHC-catalyzed decarboxylative cycloaddition. The disclosed compounds may be utilized to treat diseases and disorders associated with the biological activity of dihydrobenzoxazinone compounds and dihydroquinolone compounds.

19 Claims, 12 Drawing Sheets

(56) References Cited

OTHER PUBLICATIONS

Chen, X-Y, et al. "N-Heterocyclic Carbene Catalysis via Azolium Dienolates: An Efficient Strategy for Remote Enantioselective Functionalizations." Angewandte Chemie International Edition 57.15 (2018): 3862-3873.
Cheng, J, et al. "Carbene-Catalyzed Indole 3-Methyl C (sp3)-H Bond Functionalization." The Journal of organic chemistry 82.24 (2017): 13342-13347.
Cohen, D. T., et al. "Cooperative Lewis acid/N-heterocyclic carbene catalysis." Chemical science 3.1 (2012): 53-57.
Hu, Y, et al. "NHC-Catalyzed Efficient Syntheses of Isoquinolinones or Isochromanones through Formal [4+2] Cycloaddition of o-Quinodimethanes with Acylhydrazones or Ketones." ChemistrySelect 3.6 (2018): 1708-1712.
Ilas, J., et al. "Recent advances in the synthesis of 2H-1,4-benzoxazin-3-(4H)-ones and 3, 4-dihydro-2H-1,4-benzoxazines." Tetrahedron 31.61 (2005): 7325-7348.
Janssen-Muller, D, et al. "Annulation of o-quinodimethanes through N-heterocyclic carbene catalysis for the synthesis of 1-isochromanones." Organic letters 18.17 (2016): 4444-4447.
Katritzky, A. R., et al. "Recent progress in the synthesis of 1, 2, 3,4,-tetrahydroquinolines." Tetrahedron 52.48 (1996): 15031-15070.
Kawabata, T et al. "Memory of chirality: asymmetric induction based on the dynamic chirality of enolates." Topics in Stereochemistry 23 (2003): 175-206.
Kawabata, T et al. "Memory of chirality: enantioselective alkylation reactions at an asymmetric carbon adjacent to a carbonyl group." Journal of the American Chemical Society 113.25 (1991): 9694-9696.
Kumar, P., et al. "Radical-Induced, Palladium-Catalyzed C—H Activation: An Approach to Functionalize 4H-Benzo [d] [1, 3] oxazin-4-one Derivatives by Using Toluenes, Aldehydes, and Benzyl Alcohols." European Journal of Organic Chemistry 2018.13 (2018): 1552-1558.
Lee, A., et al. "Carbene-Catalyzed Enantioselective Decarboxylative Annulations to Access Dihydrobenzoxazinones and Quinolones." Angewandte Chemie International Edition 58.18 (Mar. 2019): 5941-5945.
Levens, A., et al. "Influence of the N-Substituents on the Nucleophilicity and Lewis Basicity of N-Heterocyclic Carbenes." Organic letters 18.15 (2016): 3566-3569.
Liu, F., et al. "Designing N-Heterocyclic Carbenes: Simultaneous Enhancement of Reactivity and Enantioselectivity in the Asymmetric Hydroacylation of Cyclopropenes." Angewandte Chemie International Edition 50.52 (2011): 12626-12630.
Lu, L-Q, et al. "Relay iron/chiral Brønsted acid catalysis: enantioselective hydrogenation of benzoxazinones." Journal of the American Chemical Society 137.7 (2015): 2763-2768.
Menon, R. S., et al. (2015). Recent advances in employing homoenolates generated by N-heterocyclic carbene (NHC) catalysis in carbon-carbon bond-forming reactions. Chemical Society Reviews, 44(15), 5040-5052.
Nammalwar, B. et al. "Recent Syntheses of 1, 2, 3, 4-Tetrahydroquinolines, 2, 3-Dihydro-4 (1H)-quinolinones and 4 (1H)-Quinolinones using domino reactions." Molecules 19.1 (2014): 204-232.
Nunez-Rico, J L, et al. "[Ir (P—OP)]-Catalyzed Asymmetric Hydrogenation of Diversely Substituted C=N-Containing Heterocycles." Organic Letters 15.8 (2013): 2066-2069.
Oshiro, Y., et al. "3, 4-Dihydro-2 (1 H)-quinolinone as a novel antidepressant drug: synthesis and pharmacology of 1-[3-[4-(3-chlorophenyl)-1-piperazinyl] propyl]-3, 4-dihydro-5-methoxy-2 (1 H)-quinolinone and its derivatives." Journal of medicinal chemistry 43.2 (2000): 177-189.
Patel, K., et al. "Secondary interactions arrest the hemiaminal intermediate to invert the Modus Operandi of Schiff Base Reaction: A Route to Benzoxazinones." The Journal of Organic Chemistry 82.8 (2017): 4342-4351.
Qi, X., et al. "Palladium-Catalyzed Carbonylative Synthesis of N-Acetyl Benzoxazinones." ChemCatChem 10.16 (2018): 3415-3418.
Rueping, M. et al. "Remarkably low catalyst loading in Brønsted acid catalyzed transfer hydrogenations: enantioselective reduction of benzoxazines, benzothiazines, and benzoxazinones." Angewandte Chemie International Edition 45.40 (2006): 6751-6755.
Seebach, D. et al. "Alkylation of amino acids without loss of optical activity: a- and β-alkylation of an aspartic acid derivative." Angewandte Chemie International Edition in English 20.11 (1981): 971-971.
Segura, JL et al. "o-Quinodimethanes: efficient intermediates in organic synthesis." Chemical reviews 99.11 (1999): 3199-3246.
Shen, L-T, et al. "N-Heterocyclic Carbene-Catalyzed Cyclization of Unsaturated Acyl Chlorides and Ketones." Advanced Synthesis & Catalysis 353.11-12 (2011): 1943-1948.
Smith III A. B., et al. "Evolution of the Petasis-Ferrier union/rearrangement tactic: construction of architecturally complex natural products possessing the ubiquitous cis-2, 6-substituted tetrahydropyran structural element." Accounts of chemical research 41.5 (2008): 675-687.
Smith, A. B., et al. "Total Synthesis of (+)-Phorboxazole A Exploiting the Petasis-Ferrier Rearrangement." Journal of the American Chemical Society 123.44 (2001): 10942-10953.
Terada, M. et al. "Double Bond Isomerization/Enantioselective Aza-Petasis-Ferrier Rearrangement Sequence as an Efficient Entry to Anti -and Enantioenriched β-Amino Aldehydes." Journal of the American Chemical Society 131.18 (2009): 6354-6355.
Trost, B. M., et al. "Enantioselective Palladium-Catalyzed [3+2] Cycloaddition of Trimethylenemethane and Fluorinated Ketones." Angewandte Chemie International Edition 57.38 (2018): 12333-12337.
Vora, H. U., et al. "Exploiting Acyl and Enol Azolium Intermediates via N-Hetero-cyclic Carbene-Catalyzed Reactions of a-Reducible Aldehydes." Advanced synthesis & catalysis 354.9 (2012): 1617-1639.
Wang, H., et al. "Addition of N-Heterocyclic Carbene Catalyst to Aryl Esters Induces Remote C—Si Bond Activation and Benzylic Carbon Functionalization." Organic letters 20.2 (2018): 333-336.
Wang, M. H., et al. "Cooperative Catalysis and Activation with N-Heterocyclic Carbenes." Angewandte Chemie International Edition 55.48 (2016): 14912-14922.
Wang, X. et al. "Mild Arl-Catalyzed C (sp2)-H or C (sp3)-H Functionalization/C—O Formation: An Intriguing Catalyst-Controlled Selectivity Switch." Angewandte Chemie International Edition 53.41 (2014): 11084-11087.
Wolfer, J., et al. "Catalytic, Asymmetric Synthesis of 1, 4-Benzoxazinones: A Remarkably Enantioselective Route to a-Amino Acid Derivatives from o-Benzoquinone Imides." Angewandte Chemie International Edition 45.44 (2006): 7398-7400.
Wurz, N. E., et al. "Highly Enantioselective Intermolecular Stetter Reaction of Simple Acrylates: Synthesis of a-Chiral ?-Ketoesters." Chemistry—A European Journal 18.51 (2012): 16297-16301.
Xu, J. et al. "N-Heterocyclic carbene catalyzed [4+2] annulation reactions with In Situ generated heterocyclic ortho-quinodimethanes." Organic letters 18.15 (2016): 3822-3825.
Yang, B. et al. "Recent advances in the application of Diels-Alder reactions involving o-quinodimethanes, aza-o-quinone methides and o-quinone methides in natural product total synthesis." Chemical Society Reviews 47.21 (2018): 7926-7953.
Yoshida, H., et al. "Aryne, ortho-quinone methide, and ortho-quinodimethane: Synthesis of multisubstituted arenes using the aromatic reactive intermediates." Bulletin of the Chemical Society of Japan 83.3 (2010): 199-219.
Zhang, N., et al. "Hypervalent Iodine-Mediated Oxygenation of N, N-Diaryl Tertiary Amines: Intramolecular Functionalization of sp3 C—H Bonds Adjacent to Nitrogen." The Journal of organic chemistry 79.21 (2014): 10581-10587.
Zhang, X., et al. "Rhodium-catalyzed asymmetric arylation of N-and O-containing cyclic aldimines: facile and efficient access to highly optically active 3, 4-dihydrobenzo [1, 4] oxazin-2-ones and dihydroquinoxalinones." Organic Chemistry Frontiers 3.8 (2016): 944-948.

(56) References Cited

OTHER PUBLICATIONS

Zhao, H., et al. "Design, synthesis, and discovery of 3-piperazinyl-3, 4-dihydro-2 (1H)-quinolinone derivatives: a novel series of mixed dopamine D2/D4 receptor antagonists." Bioorganic & medicinal chemistry letters 10.18 (2000): 2119-2122.

Zheng, Y., et al. "Octahedral ruthenium complex with exclusive metal-centered chirality for highly effective asymmetric catalysis." Journal of the American Chemical Society 139.12 (2017): 4322-4325.

* cited by examiner

SUBSTITUTED DIHYDROBENZOXAZINONES, DIHYDROQUINOLONES, AND METHODS OF THEIR USE AND SYNTHESIS

CROSS-REFERENCE TO RELATED APPLICATION

This application claims priority under 35 U.S.C. § 119(e) to U.S. Provisional Application No. 62/870,516, filed Jul. 3, 2019, the contents of which are herein incorporated by reference.

STATEMENT REGARDING FEDERALLY SPONSORED RESEARCH OR DEVELOPMENT

This invention was made with government support under GM073072 awarded by the National Institutes of Health. The government has certain rights in the invention.

FIELD

The field of the invention relates to dihydrobenzoxazinones compounds, dihydroquinolone compounds, and their methods of use and synthesis. In particular, the field of the invention relates to substituted dihydrobenzoxazinones compounds and dihydroquinolone compounds that exhibit a broad range of bioactivities, such as, antifungal, antimicrobial, and antifeedant effects, among others. Further, dihydrobenzoxazinone motifs and dihydroquinolone motifs commonly are used as an intermediate or scaffold for heterocyclic compounds that exhibit a broad range of bioactivities, such as antiinflammatory, immunoinflammatory treatments, antiulcer agents, antibacterial, heart disease treatment, diabetes, neurodegenerative, cardiovascular disorders, autoimmune, anxiety, depression, antipsychotic agents, antithrombotic action, among others.

BACKGROUND

Dihydrobenzoxazinones are an important class of N-heterocyclic compounds widely found in pharmaceutical molecules and natural products. (See, e.g., Powers et al., 2002; Ilas et al., 2005; and Macias et al. 2009). The dihydrobenzoxazinone structural motif also commonly is used as an intermediate for the construction of many other heterocyclic compounds. (See, e.g., Coppola et al. 1999).

In particular, substituted benzoxazin-4-ones have been well characterized as heterocyclic acylating agents of serine proteases and act as potent irreversible inhibitors of HLE, PPE, cathepsin G, and chymotrypsin. (See, e.g., Powers et al., 2002). Benzoxazin-4-ones have a core structure of two fused aromatic rings, which offers the possibility of broad chemical variation and optimization for a particular target serine protease. (See id.).

In addition, the 2H-1,4-benzoxazin-3-(4H)-one and 3,4-dihydro-2H-1,4-benzoxazine scaffolds have been studied intensively as important heterocyclic systems for building natural and designed synthetic compounds. (See Ilas et al., 2005). 2H-1,4-benzoxazin-3-(4H)-ones and 3,4-dihydro-2H-1,4-benzoxazines have been frequently utilized as suitable skeletons for the design of biologically active compounds, ranging from herbicides and fungicides. (See id.). 1,4-Benzoxazine-3-one derivatives are potential drugs for treating heart disease, myocardial necrosis or arrhythmia, and 1,4-benzoxazine derivatives possess peroxisome proliferator-activated receptor α (PPARα) and PPARγ agonist activity and could be used in treating diabetes, hyperlipidemia and other diabetic complications. (See id.). 1,4-benzoxazines are inhibitors of nitric oxide synthase (NOS) and are potential drugs for treating neurodegenerative, inflammatory, autoimmune and cardiovascular disorders. (See id.). 2-methyl-3-oxo-3,4-dihydro-2H-1,4-benzoxazine-2-carboxylic acid derivatives were found to be potent immunostimulants. (See id.).

4-aminoalkyl-2,3-dihydro-1,4-benzoxazin-3-ones exhibit antiphlogistic, antipyretic and analgesic effects, which led to the proposed use of some of these compounds as efficient pharmaceuticals. Indeed, calcium channel blockers based on substituted 1,4-benzoxazinones are claimed to be useful as antihypertensives, vasodilators, and anti-ischemia agents. (See id.). In addition, several 1,4-benzoxazinone derivatives have been described as useful antifungal drugs and broncholytics, whereas some synthetic benzoxazolinones have been proposed as useful central nervous system agents. (See id.). The application of benzoxazinone derivatives as pharmaceuticals for the treatment of mental disorders has been the most promising line in recent times. (See id.).

1,2-dihydro-4H-3,1-benzoxazine-4-one derivatives also have been disclosed in the art. (See, e.g., U.S. Pat. No. 4,894,374; the content of which is incorporated herein by reference in its entirety). These 1,2-dihydro-4H-3,1-benzoxazine-4-one derivatives have been shown to function as inhibitors of interleukin 1, and as such, these compounds can be used for treating immunoinflammatory conditions. (See id.).

Consequently, new synthetic methods for the preparation of enantio-enriched dihydrobenzoxazinones could fuel further studies on this versatile class of compound. To date, the majority of asymmetric methods for dihydrobenzoxazinone synthesis has focused on the dihydrobenzoxazin-2-one substructure, using a variety of methods including formal [4+2] cycloaddition of o-benzoquinone imides with ketenes (see, e.g., Wolfer et al., 2006), Rh-catalyzed conjugate addition (see, e.g., Zhang et al. 2016), Ir-catalyzed hydrogenation (see, e.g., Nunez-Rico et al., 2013), and Brønsted acid-catalyzed transfer hydrogenation (see, e.g, Rueping et al., 2006 and Lu et al., 2015). The isomeric dihydrobenzoxazin-4-one substructure is also prevalent in both natural products and drug candidates. Although several straightforward racemic syntheses of dihydrobenzoxazin-4-ones have been reported, enantioselective methods for their construction remain underdeveloped to date. (See, e.g., Wang et al., 2014; Zhang et al. 2014; Patel et al., 2017; Qi et al., 2018; and Kumar et al., 2018).

N-heterocyclic carbene (NHC) catalysis has emerged as a powerful strategy for the construction of carbo- and heterocyclic compounds over the past decade. (See, e.g., Enders et al., 2007; Bugaut et al., 2012; Vora et al., 2012; Izquierdo et al., 2012; Cohen et al., 2012; Mahatthananchai et al., 2014; Hopkinson et al., 2014; Menon et al., 2015; Flanigan et al., 2015; and Wang et al., 2016). NHC-catalyzed Umpolung reactions employing enals has provided access to numerous divergent nucleophilic species, including acyl anion, enolate, and homoenolate equivalents. In 2011, Ye demonstrated that NHC catalysis could also access dienolate equivalents. (See Shen et al., 2011). Following Ye's preliminary disclosure, several reports of reactions employing "azolium dienolates" generated from various carbonyl precursors have emerged. (See Chen et al. 2018). Particularly, the NHC-catalyzed γ-functionalization of aromatic substrates has received attention due to the innovative deployment of unconventional o-quinodimethanes (o-QDMs) as substrates. (See Segura et al., 1999; and Hiroto et al., 2010).

In 2013, Chi and co-workers initially reported NRC-bound o-QDM intermediates could be generated from o-methyl heteroaryl aldehydes (see Chen et al., 2013) and o-methyl heteroaryl esters (see Xu et al., 2016). Following these studies, several approaches to extend this reactivity to carbocyclic aromatic systems have emerged, notably, Glorius (see Glorious et al., 2016) and Rovis (see Rovis et al., 2017) found that NHCs could displace an appropriate benzylic leaving group to access the corresponding NHC-bound o-QDMs. There have been significantly fewer developments employing o-quinone methides (o-QMs) or aza-o-quinone methides (aza-o-QMs) as nucleophiles in NHC catalysis. A notable recent advance by Chi employed salicylaldehydes in the presence of a stoichiometric oxidant and a base to generate an NHC-bound o-QM, which participated in an annulation with trifluoromethyl ketone electrophiles (see Chen et al., 2017). These contributions have expanded the scope of carbene catalysis, while simultaneously presenting opportunities to develop new and complementary methods employing NHC-bound o-QDM-like nucleophiles.

Here, the inventors disclose a direct decarboxylative strategy for the generation of aza-o-quinone methides (aza-o-QMs) by N-heterocyclic carbene (NHC) catalysis. This process requires no stoichiometric additives in contrast with current approaches. Aza-o-QMs react with trifluoromethyl ketones via a formal [4+2] manifold to access highly enantioenriched dihydrobenzoxazin-4-one products, which can be converted to dihydroquinolones via an interesting stereoretentive aza-Petasis-Ferrier rearrangement sequence. Complementary DFT studies provided an accurate prediction of the reaction enantioselectivity and lend further insight to the origins of stereocontrol. Additionally, a computed potential energy surface around the major transition structure suggests a concerted asynchronous mechanism for the formal annulation.

SUMMARY

Disclosed are dihydrobenzoxazinone compounds, dihydroquinolone compounds, and methods of their synthesis. The disclosed compounds may be prepared by reacting a benzoxazinedione compound and a ketone compound in the presence of an N-heterocyclic carbine (NHC) catalyst to perform a NHC-catalyzed decarboxylative cycloaddition. The disclosed compounds may be utilized to treat diseases and disorders associated with the biological activity of dihydrobenzoxazinone compounds and dihydroquinolone compounds.

In some embodiments, the disclosed compounds may have a formula as follows, or a salt or hydrate thereof:

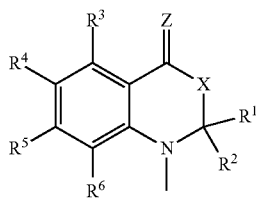

The disclosed compounds are optionally substituted. In some embodiments, $R^1$ is selected from alkyl, alkoxy, carboxyalkyl, haloalkyl, and amino. In some embodiments, $R^2$ is selected from cycloalkyl, aryl, heteroaryl, which optionally is substituted at one or more positions with a substituent selected from alkyl, alkoxy, halo, haloalkyl, and amino. In some embodiments, $R^3$, $R^4$, $R^5$, and $R^6$ are independently selected from hydrogen, alkyl, alkoxy, halo, haloalkyl, and amino. In some embodiments, X is selected from O and $CH_2$. In some embodiments, Z is selected from O and $CH_2$.

Also disclosed are pharmaceutical compositions that comprise the disclosed compounds together with a suitable carrier, diluent, or excipient. The pharmaceutical compositions may comprise an effective amount of the disclosed compounds (or salts or hydrates thereof) for treating or preventing a disease, disorder, disorders, conditions, such as, but not limited to, inflammatory conditions, autoimmune inflammation, ulcers, bacterial infections, heart disease, diabetes, neurodegenerative disorders, cardiovascular disorders, autoimmune disorders, anxiety, thrombosis, psychotic disorders, and depression. The pharmaceutical compositions also may comprise an effective amount of the disclosed compounds (or salts or hydrates thereof) for treating or preventing viral infections, bacterial infections, and fungal infections Also disclosed herein are methods of treating or preventing any of the aforementioned diseases or disorders that include administering the disclosed compounds to a subject in need thereof in an effective amount to treat or prevent the disease or disorder. For example, the compound may be formulated in a pharmaceutical composition and administered to a subject having or suspected of having an inflammatory condition, autoimmune inflammation, ulcers, bacterial infections, heart disease, diabetes, neurodegenerative disorders, cardiovascular disorders, autoimmune disorders, anxiety, thrombosis, psychotic disorders, and depression. Alternatively, the compound may be formulated in a pharmaceutical composition and administered to a subject having or suspected of having a viral infection, a bacterial infection, or a fungal infection.

BRIEF DESCRIPTION OF THE DRAWINGS

FIG. 2. Potential energy surface plot showing a concerted mechanism for the conversion of I and 2a.

DETAILED DESCRIPTION

Figure 1:
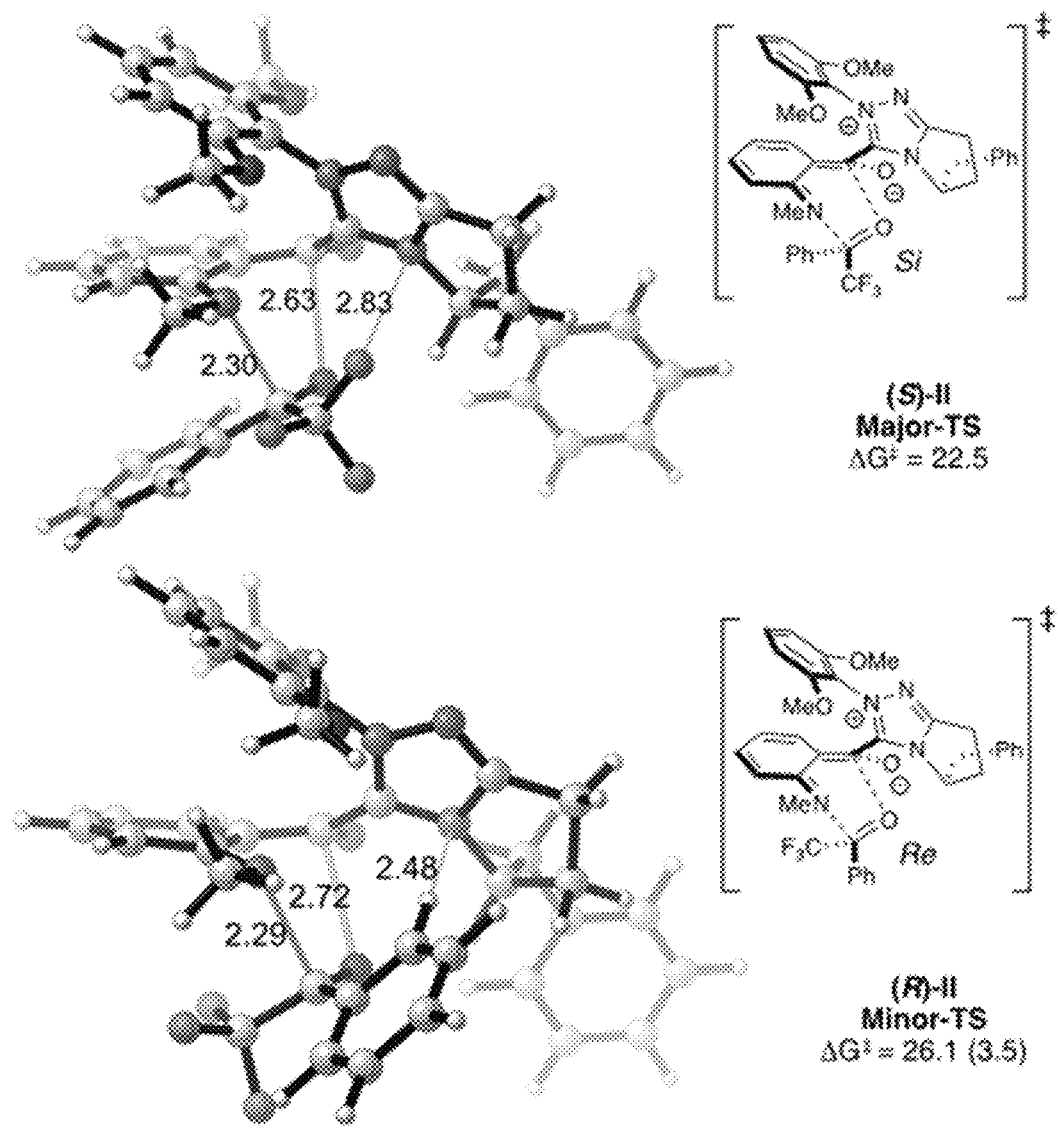
FIG. 1. DFT major and minor [4+2] cycloaddition transition structures. Distances in A and energies in kcal/mol.

The present invention is described herein using several definitions, as set forth below and throughout the application.

Definitions

The disclosed subject matter may be further described using definitions and terminology as follows. The definitions and terminology used herein are for the purpose of describing particular embodiments only, and are not intended to be limiting.

As used in this specification and the claims, the singular forms "a," "an," and "the" include plural forms unless the context clearly dictates otherwise. For example, the term "a substituent" should be interpreted to mean "one or more substituents," unless the context clearly dictates otherwise.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The phrase "such as" should be interpreted as "for example, including." Moreover the use of any and all exemplary language, including but not limited to "such as", is intended merely to better illuminate the invention and does not pose a limitation on the scope of the invention unless otherwise claimed.

Furthermore, in those instances where a convention analogous to "at least one of A, B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together.). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or 'B or "A and B."

All language such as "up to," "at least," "greater than," "less than," and the like, include the number recited and refer to ranges which can subsequently be broken down into ranges and subranges. A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

A "subject in need thereof" as utilized herein refers to a subject in need of treatment for a disease or disorder associated with a compound(s) disclosed herein, such as a substituted chromane. For example, a "subject in need thereof" may include a patient having a viral infection, bacterial infection, fungal infection, tumor growth, allergic reactions, inflammatory conditions, cancer and cell proliferative disorders. The term "subject" may be used interchangeably with the terms "individual" and "patient" and includes human and non-human mammalian subjects.

Chemical Entities

New chemical entities and uses for chemical entities are disclosed herein. The chemical entities may be described using terminology known in the art and further discussed below.

As used herein, an asterisk "*" or a plus sign "+" may be used to designate the point of attachment for any radical group or substituent group.

The term "alkyl" as contemplated herein includes a straight-chain or branched alkyl radical in all of its isomeric forms, such as a straight or branched group of 1-12, 1-10, or 1-6 carbon atoms, referred to herein as C1-C12 alkyl, C1-C10-alkyl, and C1-C6-alkyl, respectively.

The term "alkylene" refers to a diradical of straight-chain or branched alkyl group (i.e., a diradical of straight-chain or branched C1-C6 alkyl group). Exemplary alkylene groups include, but are not limited to —$CH_2$—, —$CH_2CH_2$—, —$CH_2CH_2CH_2$—, —$CH(CH_3)CH_2$—, —$CH_2CH(CH_3)$ $CH_2$—, —$CH(CH_2CH_3)CH_2$—, and the like.

The term "halo" refers to a halogen atom or a halogen radical, for example, —F, —Cl, —Br, or —I.

The term "haloalkyl" refers to an alkyl group that is substituted with at least one halogen. For example, —$CH_2F$, —$CHF_2$, —$CF_3$, —$CH_2CF_3$, —$CF_2CF_3$, and the like.

The term "heteroalkyl" as used herein refers to an "alkyl" group in which at least one carbon atom has been replaced with a heteroatom (e.g., an O, N, or S atom). One type of heteroalkyl group is an "alkoxy" group.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as C2-C12-alkenyl, C2-C10-alkenyl, and C2-C6-alkenyl, respectively.

The term "alkynyl" as used herein refers to an unsaturated straight or branched hydrocarbon having at least one carbon-carbon triple bond, such as a straight or branched group of 2-12, 2-10, or 2-6 carbon atoms, referred to herein as C2-C12-alkynyl, C2-C10-alkynyl, and C2-C6-alkynyl, respectively.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "C4-8-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido or carboxyamido, amidino, amino, aryl, arylalkyl, azido, carbamate, carbonate, carboxy, cyano, cycloalkyl, ester, ether, formyl, halo, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term "cycloheteroalkyl" refers to a monovalent saturated cyclic, bicyclic, or bridged cyclic hydrocarbon group of 3-12, 3-8, 4-8, or 4-6 carbons in which at least one carbon of the cycloalkane is replaced with a heteroatom such as, for example, N, O, and/or S.

The term "cycloalkylene" refers to a cycloalkyl group that is unsaturated at one or more ring bonds.

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number oring carbon atoms. For example, the partially unsaturated carbocyclyl may contain 5-14, 5-12, 5-8, or 5-6 ring carbon atoms, and accordingly be referred to as a 5-14, 5-12, 5-8, or 5-6 membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido or carboxyamido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. The term "heteroaryl" is art-recognized and refers to an aryl group in which carbon atom within a ring of the aryl group is substituted with a hetereoatom, which may include N, O, and S, for example. Unless specified otherwise, the aromatic ring or an aryl group or a heteroaryl group may be substituted at one or more ring positions with, for example, halogen, azide, alkyl, aralkyl, alkenyl, alkynyl, cycloalkyl, hydroxyl, alkoxy, amino, nitro, sulfhydryl, imino, amido or carboxyamido, carboxylic acid, —C(O)alkyl, —C(O)O-alkyl, carbonyl, carboxyl, thioalkyl, sulfonyl, sulfonamido, sulfonamide, ketone, aldehyde, ester, heterocyclyl, aryl or heteroaryl moieties, —$CF_3$, —CN, or the like. In certain embodiments, the aromatic ring or an aryl group or a heteroaryl group is substituted at one or more ring positions with halogen, alkyl, hydroxyl, or alkoxyl. In certain other embodiments, the aromatic ring or an aryl group or a heteroaryl group is not substituted, i.e., it is unsubstituted. In certain embodiments, the aromatic ring or an aryl group or a heteroaryl group is a 6-10 membered single ring structure or a bicyclic ring structure.

The term "arylalkyl" is art-recognized and refers to a radical defined as -alkyl-aryl, where "alkyl" and "aryl" are as defined herein. The term "heteroarylalkyl" is art-recognized and refers to a radical defined as -alkyl-heteroaryl, where "alkyl" and "heteroaryl" are as defined herein.

The terms "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using 5 Cx-Cx nomenclature where x is an integer specifying the number of ring atoms. For example, a C3-C7 heterocyclyl group refers to a saturated or partially unsaturated 3- to 7-membered ring structure containing one to four heteroatoms, such as nitrogen, oxygen, and sulfur. The designation "C3-C7" indicates that the heterocyclic ring contains a total of from 3 to 7 ring atoms, inclusive of any heteroatoms that occupy a ring atom position.

The terms "amine" and "amino" are art-recognized and refer to both unsubstituted and substituted amines (e.g., mono-substituted amines or di-substituted amines), wherein substituents may include, for example, alkyl, cycloalkyl, heterocyclyl, alkenyl, and aryl.

The terms "alkoxy" or "alkoxyl" are art-recognized and refer to an alkyl group, as defined above, having an oxygen radical attached thereto. Representative alkoxy groups include methoxy, ethoxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and the like.

The term "carbonyl" as used herein refers to the radical —C(O)—.

The term "oxo" refers to a divalent oxygen atom —O—.

The term "carboxy" as used herein refers to the radical —COOH or its corresponding salts, e.g. —COONa, etc.

The term "carboxyalkyl" as used herein refers to the radical -alkyl-COOH, in which "alkyl" is an alkyl radical which may be straight chain or branched as described herein.

The term "amide" or "amido" or "amidyl" as used herein refers to a radical of the form —$R^1C(O)N(R^2)$—, —$R^1c(O)N(R^2)R^3$—, —$C(O)NR^2R^3$, or —$C(O)NH_2$, wherein $R^1$, $R^2$ and $R^3$, for example, are each independently hydrogen, alkyl, alkoxy, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro. The term "carboxamido" as used herein refers to the radical —C(O)NRR', where R and R' may be the same or different. R and R', for example, may be independently hydrogen, alkyl, aryl, arylalkyl, cycloalkyl, formyl, haloalkyl, heteroaryl, or heterocyclyl.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," "+" or "−" depending on the configuration of substituents around the stereogenic carbon atom and or the optical rotation observed. The present invention encompasses various stereo isomers of these compounds and mixtures thereof. Stereoisomers include enantiomers and diastereomers. Mixtures of enantiomers or diastereomers may be designated (±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise. Also contemplated herein are compositions comprising, consisting essentially of, or consisting of an enantiopure compound, which composition may comprise, consist essential of, or consist of at least about 50%, 60%, 70%, 80%, 90%, 95%, 96%, 97%, 98%, 99%, or 100% of a single enantiomer of a given compound (e.g., at least about 99% of an R enantiomer of a given compound).

Pharmaceutical Compositions and Formulations

The compounds employed in the compositions and methods disclosed herein may be administered as pharmaceutical compositions and, therefore, pharmaceutical compositions incorporating the compounds are considered to be embodiments of the compositions disclosed herein. Such compositions may take any physical form which is pharmaceutically acceptable; illustratively, they can be orally administered pharmaceutical compositions. Such pharmaceutical compositions contain an effective amount of a disclosed compound, which effective amount is related to the daily dose of the compound to be administered. Each dosage unit may contain the daily dose of a given compound or each dosage unit may contain a fraction of the daily dose, such as one-half or one-third of the dose. The amount of each compound to be contained in each dosage unit can depend, in part, on the identity of the particular compound chosen for the therapy and other factors, such as the indication for which it is given. The pharmaceutical compositions disclosed herein may be formulated so as to provide quick, sustained, or delayed release of the active ingredient after administration to the patient by employing well known procedures.

The compounds for use according to the methods of disclosed herein may be administered as a single compound or a combination of compounds. For example, a compound that modulates the dihydrobenzoxazinones activity may be administered as a single compound or in combination with another compound that modulates dihydrobenzoxazinones activity or that has a different pharmacological activity.

As indicated above, pharmaceutically acceptable salts of the compounds are contemplated and also may be utilized in the disclosed methods. The term "pharmaceutically acceptable salt" as used herein, refers to salts of the compounds which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Acids commonly employed to form acid addition salts may include inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of suitable pharmaceutically acceptable salts may include the sulfate, pyrosulfate, bisulfate, sulfite, bisulfate, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleat-, butyne-.1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, α-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Bases useful in preparing such salts include sodium hydroxide, potassium hydroxide, ammonium hydroxide, potassium carbonate, sodium carbonate, sodium bicarbonate, potassium bicarbonate, calcium hydroxide, calcium carbonate, and the like.

The particular counter-ion forming a part of any salt of a compound disclosed herein is may not be critical to the activity of the compound, so long as the salt as a whole is pharmacologically acceptable and as long as the counterion does not contribute undesired qualities to the salt as a whole. Undesired qualities may include undesirably solubility or toxicity.

Pharmaceutically acceptable esters and amides of the compounds can also be employed in the compositions and methods disclosed herein. Examples of suitable esters include alkyl, aryl, and aralkyl esters, such as methyl esters, ethyl esters, propyl esters, dodecyl esters, benzyl esters, and the like. Examples of suitable amides include unsubstituted amides, monosubstituted amides, and di substituted amides, such as methyl amide, dimethyl amide, methyl ethyl amide, and the like.

In addition, the methods disclosed herein may be practiced using solvate forms of the compounds or salts, esters, and/or amides, thereof. Solvate forms may include ethanol solvates, hydrates, and the like.

The pharmaceutical compositions may be utilized in methods of treating a disease or disorder associated with the substituted dihydrobenzoxazinone's activity. As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disease or disorder. As such, the methods disclosed herein encompass both therapeutic and prophylactic administration.

As used herein the term "effective amount" refers to the amount or dose of the compound, upon single or multiple dose administration to the subject, which provides the desired effect in the subject under diagnosis or treatment. The disclosed methods may include administering an effective amount of the disclosed compounds (e.g., as present in a pharmaceutical composition) for treating one or more of the aforementioned diseases or disorders.

An effective amount can be readily determined by the attending diagnostician, as one skilled in the art, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the disease or disorder involved; the response of the individual subject; the particular compound administered; the mode of administration; the bioavailability characteristics of the preparation administered; the dose regimen selected; the use of concomitant medication; and other relevant circumstances.

A typical daily dose may contain from about 0.01 mg/kg to about 100 mg/kg (such as from about 0.05 mg/kg to about 50 mg/kg and/or from about 0.1 mg/kg to about 25 mg/kg) of each compound used in the present method of treatment.

Compositions can be formulated in a unit dosage form, each dosage containing from about 1 to about 500 mg of each compound individually or in a single unit dosage form, such as from about 5 to about 300 mg, from about 10 to about 100 mg, and/or about 25 mg. The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

Oral administration is an illustrative route of administering the compounds employed in the compositions and methods disclosed herein. Other illustrative routes of administration include transdermal, percutaneous, intravenous, intramuscular, intranasal, buccal, intrathecal, intracerebral, or intrarectal routes. The route of administration may be varied in any way, limited by the physical properties of the compounds being employed and the convenience of the subject and the caregiver.

As one skilled in the art will appreciate, suitable formulations include those that are suitable for more than one route of administration. For example, the formulation can be one that is suitable for both intrathecal and intracerebral administration. Alternatively, suitable formulations include those that are suitable for only one route of administration as well as those that are suitable for one or more routes of administration, but not suitable for one or more other routes of administration. For example, the formulation can be one that is suitable for oral, transdermal, percutaneous, intravenous, intramuscular, intranasal, buccal, and/or intrathecal administration but not suitable for intracerebral administration.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches, and suspensions. In general, compositions contain from about 0.5% to about 50% of the compound in total, depending on the desired doses and the type of composition to be used. The amount of the compound, however, is best defined as the "effective amount", that is, the amount of the compound which provides the desired dose to the patient in need of such treatment. The activity of the compounds employed in the compositions and methods disclosed herein are not believed to depend greatly on the nature of the composition, and, therefore, the compositions can be chosen and formulated primarily or solely for convenience and economy.

Capsules are prepared by mixing the compound with a suitable diluent and filling the proper amount of the mixture in capsules. The usual diluents include inert powdered substances (such as starches), powdered cellulose (especially crystalline and microcrystalline cellulose), sugars (such as fructose, mannitol and sucrose), grain flours, and similar edible powders.

Tablets are prepared by direct compression, by wet granulation, or by dry granulation. Their formulations usually incorporate diluents, binders, lubricants, and disintegrators (in addition to the compounds). Typical diluents include, for example, various types of starch, lactose, mannitol, kaolin, calcium phosphate or sulfate, inorganic salts (such as sodium chloride), and powdered sugar. Powdered cellulose derivatives can also be used. Typical tablet binders include substances such as starch, gelatin, and sugars (e.g., lactose, fructose, glucose, and the like). Natural and synthetic gums can also be used, including acacia, alginates, methylcellulose, polyvinylpyrrolidine, and the like. Polyethylene glycol, ethylcellulose, and waxes can also serve as binders.

Tablets can be coated with sugar, e.g., as a flavor enhancer and sealant. The compounds also may be formulated as chewable tablets, by using large amounts of pleasant-tasting substances, such as mannitol, in the formulation. Instantly dissolving tablet-like formulations can also be employed, for example, to assure that the patient consumes the dosage form and to avoid the difficulty that some patients experience in swallowing solid objects.

A lubricant can be used in the tablet formulation to prevent the tablet and punches from sticking in the die. The lubricant can be chosen from such slippery solids as talc, magnesium and calcium stearate, stearic acid, and hydrogenated vegetable oils.

Tablets can also contain disintegrators. Disintegrators are substances that swell when wetted to break up the tablet and release the compound. They include starches, clays, celluloses, algins, and gums. As further illustration, corn and potato starches, methylcellulose, agar, bentonite, wood cellulose, powdered natural sponge, cation-exchange resins, alginic acid, guar gum, citrus pulp, sodium lauryl sulfate, and carboxymethylcellulose can be used.

Compositions can be formulated as enteric formulations, for example, to protect the active ingredient from the strongly acid contents of the stomach. Such formulations can be created by coating a solid dosage form with a film of a polymer which is insoluble in acid environments and soluble in basic environments. Illustrative films include cellulose acetate phthalate, polyvinyl acetate phthalate, hydroxypropyl methylcellulose phthalate, and hydroxypropyl methylcellulose acetate succinate.

Transdermal patches can also be used to deliver the compounds. Transdermal patches can include a resinous composition in which the compound will dissolve or partially dissolve; and a film which protects the composition and which holds the resinous composition in contact with the skin. Other, more complicated patch compositions can also be used, such as those having a membrane pierced with a plurality of pores through which the drugs are pumped by osmotic action.

As one skilled in the art will also appreciate, the formulation can be prepared with materials (e.g., actives excipients, carriers (such as cyclodextrins), diluents, etc.) having properties (e.g., purity) that render the formulation suitable for administration to humans. Alternatively, the formulation can be prepared with materials having purity and/or other properties that render the formulation suitable for administration to non-human subjects, but not suitable for administration to humans.

Substituted Dihydrobenzoxazinones, Dihydroquinolones, and Methods of Their Use and Synthesis In some embodiments, the disclosed compounds may have formula as follows, or a salt or hydrate thereof:

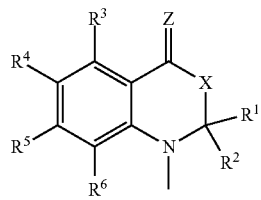

The compounds are optionally substituted, where at least one of $R^1$, $R^2$, $R^3$, $R^4$, $R^5$, and $R^6$ is not hydrogen.

In some embodiments, $R^1$ is selected from alkyl, alkoxy, carboxyalkyl, haloalkyl, and amino.

In some embodiments, $R^2$ is selected from cycloalkyl, aryl, and heteroaryl, which optionally is substituted at one or more positions selected from alkyl, alkoxy, halo, haloalkyl, and amino.

In some embodiments, $R^3$, $R^4$, $R^5$, and $R^6$ are independently selected from hydrogen, alkyl, alkoxy, halo, haloalkyl, and amino.

In some embodiments, optionally, at least one of $R^3$, $R^4$, $R^5$, and $R^6$ is not hydrogen.

In some embodiments, X is independently selected from O and $CH_2$.

In some embodiments, Z is independently selected from O and $CH_2$.

In some embodiments, $R^1$ is trifluoroalkyl (e.g., trifluoromethyl).

In some embodiments, $R^2$ is phenyl or thiophene, which optionally is substituted at one or more positions with a substituent selected from halo (e.g., fluoro, bromo, or chloro), alkoxy (e.g., methoxy), and alkyl (e.g., methyl). In some embodiments, $R^2$ is phenyl which is ortho-substituted, meta-substituted, di-meta-substituted, and/or para-substituted.

In some embodiments, at least one of $R^3$, $R^4$, $R^5$, and $R^6$ is a halo moiety, such as bromo, fluoro, chloro.

In some embodiments, at least one of $R^3$, $R^4$, $R^5$, and $R^6$ is an alkyl such as methyl, or alkoxy such as methoxy.

In some embodiments, at least one of $R^3$, $R^4$, $R^5$, and $R^6$ is hydrogen. For example, in some embodiments, $R^3$ is hydrogen. In other embodiments, $R^6$ is hydrogen.

Exemplary compounds as contemplated herein may include, but are not limited to compounds having a formula selected from:

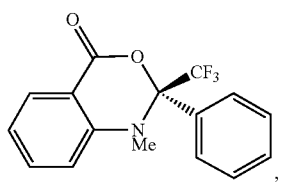

-continued

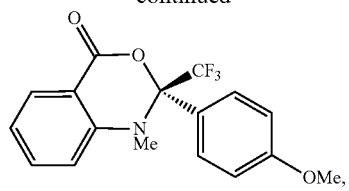

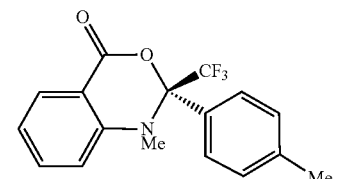

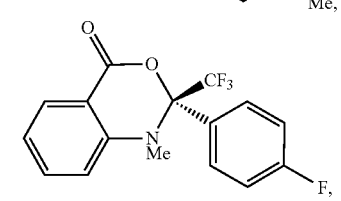

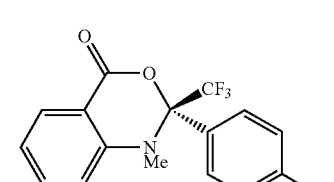

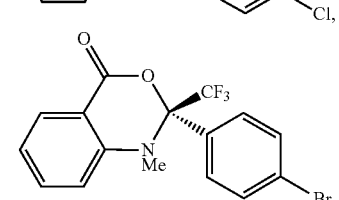

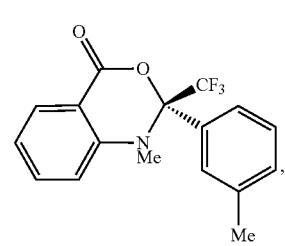

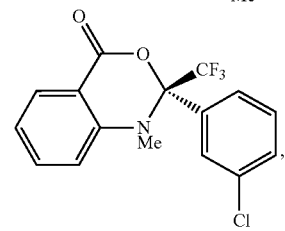

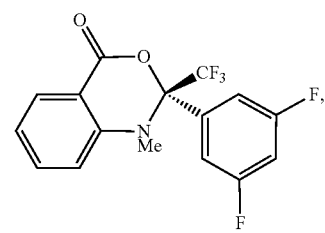

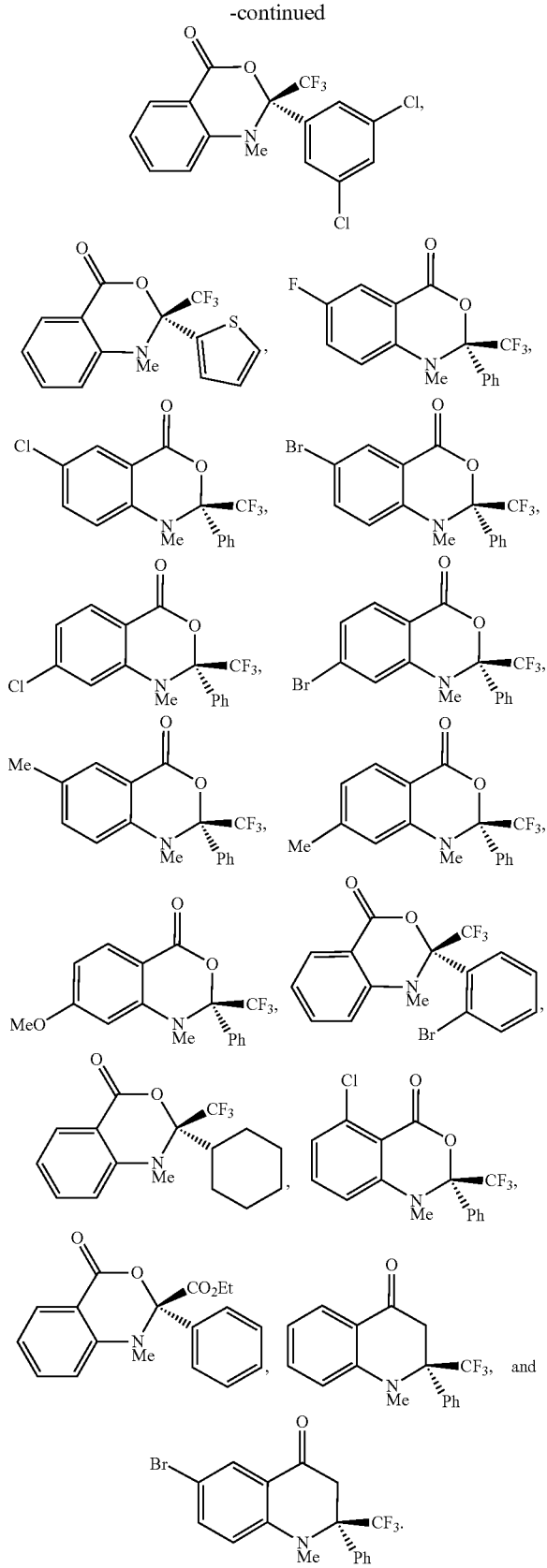

The disclosed compounds may be synthesized by N-heterocyclic carbine (NHC)-catalyzed decarboxylative cycloaddition reactions. In some embodiments, the disclosed compounds may be synthesized by methods comprising reacting:

(a) a compound of a formula

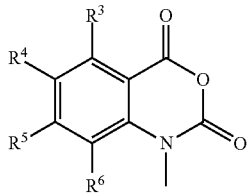

wherein:
$R^3$, $R^4$, $R^5$, and $R^6$ are independently selected from hydrogen, alkyl, alkoxy, halo, haloalkyl, and amino; and (b) a compound of a formula

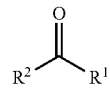

wherein:
$R^1$ is selected from alkyl, carboxyalkyl, and haloalkyl;
$R^2$ is selected from cycloalkyl, aryl, and heteroaryl, which optionally is substituted at one or more positions with a substituent selected from alkyl, alkoxy, halo, haloalkyl, and amino; wherein the compound (a) and the compound (b) are reacted in the presence of an N-heterocyclic carbine (NHC) catalyst to perform a NHC-catalyzed decarboxylative cycloaddition.

The disclosed compounds, salts thereof, and/or hydrates thereof may be formulated as pharmaceutical compositions comprising the compounds, salts thereof, and/or hydrates thereof, in a pharmaceutically acceptable carrier. The pharmaceutical compositions may be formulated for treating one or more of the aforementioned diseases or disorders.

In some embodiments, the disclosed compounds may be used for treating a patient in need of treatment. The method includes administering the disclosed compound(s) to the patient in an effective amount to treat the disease or disorder, such as a patient having an inflammatory condition, autoimmune inflammation, ulcers, bacterial infections, heart disease, diabetes, neurodegenerative disorders, cardiovascular disorders, autoimmune disorders, anxiety, thrombosis, psychotic disorders, and depression.

In some embodiments, the disclosed compounds may be used for treating subjects in need of treatment. The method includes administering the disclosed compound(s) to the subject in an effective amount to treat a viral infection, a bacterial infection, or a fungal infection.

In some embodiments, the disclosed compounds may be used for treating a plant in need of treatment. The method includes administering the disclosed compound(s) to the plant in an effective amount to treat the disease, such as bacterial infections, fungal infections, and insect infections.

EXAMPLES

The following Examples are illustrative and are not intended to limit the scope of the claimed subject matter.

Example I—Carbene-Catalyzed Enantioselective Decarboxylative Annulations to Access Dihydrobenzoxazinones and Quinolones Reference is made to Lee et al., "Carbene-Catalyzed Enantioselective Decarboxylative Annulation to Access Dihydrobenzoxazinones and Quinolones," Angewandte Chemie, Volume 58, Issue 18, Apr. 23, 2019, Pages 5941-5945, the content of which is incorporated herein by reference in its entirety.

Abstract

A direct decarboxylative strategy for the generation of aza-o-quinone methides (aza-o-QMs) by N-heterocyclic carbene (NHC) catalysis has been discovered and explored. This process requires no stoichiometric additives in contrast with current approaches. Aza-o-QMs react with trifluoromethyl ketones via a formal [4+2] manifold to access highly enantioenriched dihydrobenzoxazin-4-one products, which can be converted to dihydroquinolones via an interesting stereoretentive aza-Petasis-Ferrier rearrangement sequence. Complementary DFT studies provided an accurate prediction of the reaction enantioselectivity, and lend further insight to the origins of stereocontrol. Additionally, a computed potential energy surface around the major transition structure suggests a concerted asynchronous mechanism for the formal annulation.

Introduction

Dihydrobenzoxazinones are an important class of N-heterocyclic compounds widely found in pharmaceutical molecules and natural products.[1] The dihydrobenzoxazinone structural motif is also commonly used as an intermediate for the construction of many other heterocyclic compounds.[2] Consequently, new synthetic methods for the preparation of enantioenriched dihydrobenzoxazinones could fuel further studies on this versatile compound class. To date, the majority of asymmetric methods for dihydrobenzoxazinone synthesis has focused on the dihydrobenzoxazin-2-one substructure, using a variety of methods including formal [4+2] cycloaddition of o-benzoquinone imides with ketenes,[3] Rh-catalyzed conjugate addition,[4] Ir-catalyzed hydrogenation,[5] and Brønsted acid-catalyzed transfer hydrogenation.[6] The isomeric dihydrobenzoxazin-4-one substructure is also prevalent in both natural products and drug candidates. Although several straightforward racemic syntheses of dihydrobenzoxazin-4-ones have been reported, enantioselective methods for their construction remain underdeveloped to date.[7]

N-heterocyclic carbene (NHC) catalysis has emerged as a powerful strategy for the construction of carbo- and heterocyclic compounds over the past decade.[8] NHC-catalyzed Umpolung reactions employing enals has provided access to numerous divergent nucleophilic species, including acyl anion, enolate, and homoenolate equivalents. In 2011, Ye demonstrated that NHC catalysis could also access dienolate equivalents.[9] Following Ye's preliminary disclosure, several reports of reactions employing "azolium dienolates" generated from various carbonyl precursors have emerged.[10] Particularly, the NHC-catalyzed γ-functionalization of aromatic substrates[11] has received attention due to the innovative deployment of unconventional o-quinodimethanes (o-QDMs) as substrates (Scheme 1a).[12]

Scheme 1. Generation of NHC-bound o-QDMs and o-QMs.

(a) Annulations via NHC-Bound o-QDM Intermediate

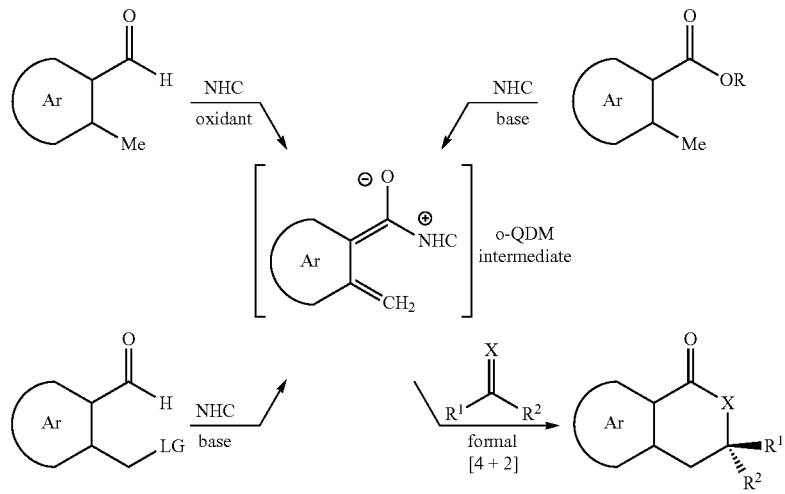

(b) Annulation via NHC-Bound o-QM Intermediate

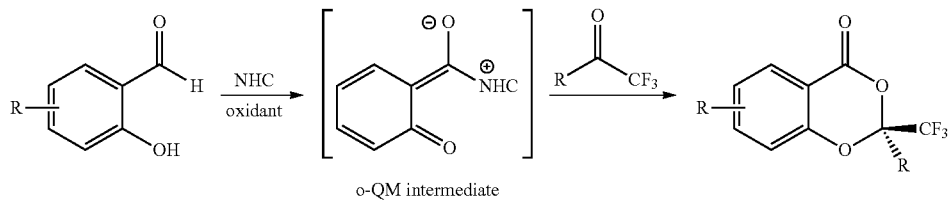

(c) This Work

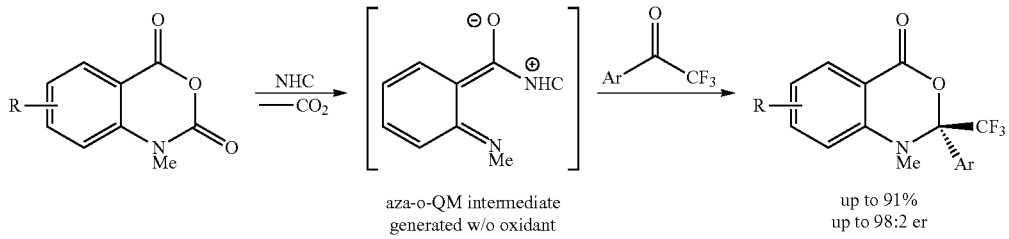

aza-o-QM intermediate
generated w/o oxidant up to 91%
up to 98:2 er

In 2013, Chi and co-workers initially reported NHC-bound o-QDM intermediates could be generated from o-methyl heteroaryl aldehydesr[11a] and o-methyl heteroaryl esters.[11b] Following these studies, several approaches to extend this reactivity to carbocyclic aromatic systems have emerged, notably, Glorius[11c] and Rovis[11d] found that NHCs could displace an appropriate benzylic leaving group to access the corresponding NHC-bound o-QDMs (Scheme 1a). There have been significantly fewer developments employing o-quinone methides (o-QMs) or aza-o-quinone methides (aza-o-QMs) as nucleophiles in NHC catalysis. A notable recent advance by Chi employed salicylaldehydes in the presence of stoichiometric oxidant and base to generate an NEC-bound o-QM, which participated in an annulation with trifluoromethyl ketone electrophiles (Scheme 1b).[13] These contributions have expanded the scope of carbene catalysis, while simultaneously presenting opportunities to develop new and complementary methods employing NHC-bound o-QDM-like nucleophiles. Herein, we report a decarboxylative transformation proceeding via an NHC-bound aza-o-QM intermediate to access enantioenriched dihydrobenzoxazin-4-ones (Scheme 1c). This advance generates $CO_2$ as the byproduct and does not require external oxidants or stoichiometric bases, and represents the first use of NHC-bound aza-o-QMs as nucleophilic partners in asymmetric catalysis.

Results

We initiated our studies on the decarboxylative cycloaddition using N-methylisatoic anhydride substrate 1a with trifluoromethyl ketone 2a (Scheme 2). An achiral triazolium catalyst with the strong, and non-nucleophilic base KHMDS provided the desired dihydrobenzoxazinone 3a in moderate isolated yield at 30° C. After evaluating triazolium catalysts A-D, we found that catalyst D bearing a mesityl substituent gave the product 3a in 19% yield and 98:2 er, while less nucleophilic NHCs (B and C) did not provide desired reactivity with 1a.[15] We thus investigated the reaction using catalyst E[16] and obtained 3a in 72% yield and 97:3 er at 50° C. With the optimal catalyst system identified, we moved to explore the reaction scope of these new NHC-catalyzed decarboxylative cycloadditions.

A survey of different N-methyl isatoic anhydrides and trifluoromethyl ketones is summarized in Table 1. Trifluoromethyl ketones (2) with para and meta substituents of varying electronic and steric parameters were all suitable substrates for the reaction. Ketones 2a-h reacted with 1a in the presence of catalyst E generating the desired products 3b-h in moderate to good yields (49-91%) and with high stereoselectivity in all cases (95:5-98:2 er). The reactions of 3,5-substituted ketones also provided the desired products 3i and 3j in moderate yields and high stereoselectivity (56%, 97:3 er and 77%, 95:5 er, respectively). We next investigated the reaction scope of a variety of isatoic anhydrides (1). The reactions of anhydride substrates possessing electron-withdrawing halogen substituents provided products 3l-p with good yields (66-78%) and high stereoselectivity (95:5-96:4 er), although we found that for these substrates reducing the reaction temperature to 35° C. was necessary to observe high stereoselectivity. When anhydrides with electron-donating substituents such as methyl and methoxy groups were reacted with the trifluoromethyl ketone 2a, products 3q-s were also obtained in moderate to good yields (47-80%) and high stereoselectivity (96:4-97:3 er). Reactions attempted using ortho-substituted aryl trifluoromethyl ketones,[17] alkyl-trifluoromethyl ketones,[18] or α-keto esters gave the desired products with diminished yields, whereas isatins did not react under the current conditions (Table 1, bottom). In addition, different N-substituted isatoic anhydrides showed poor reactivity under current conditions.

Figure 11:
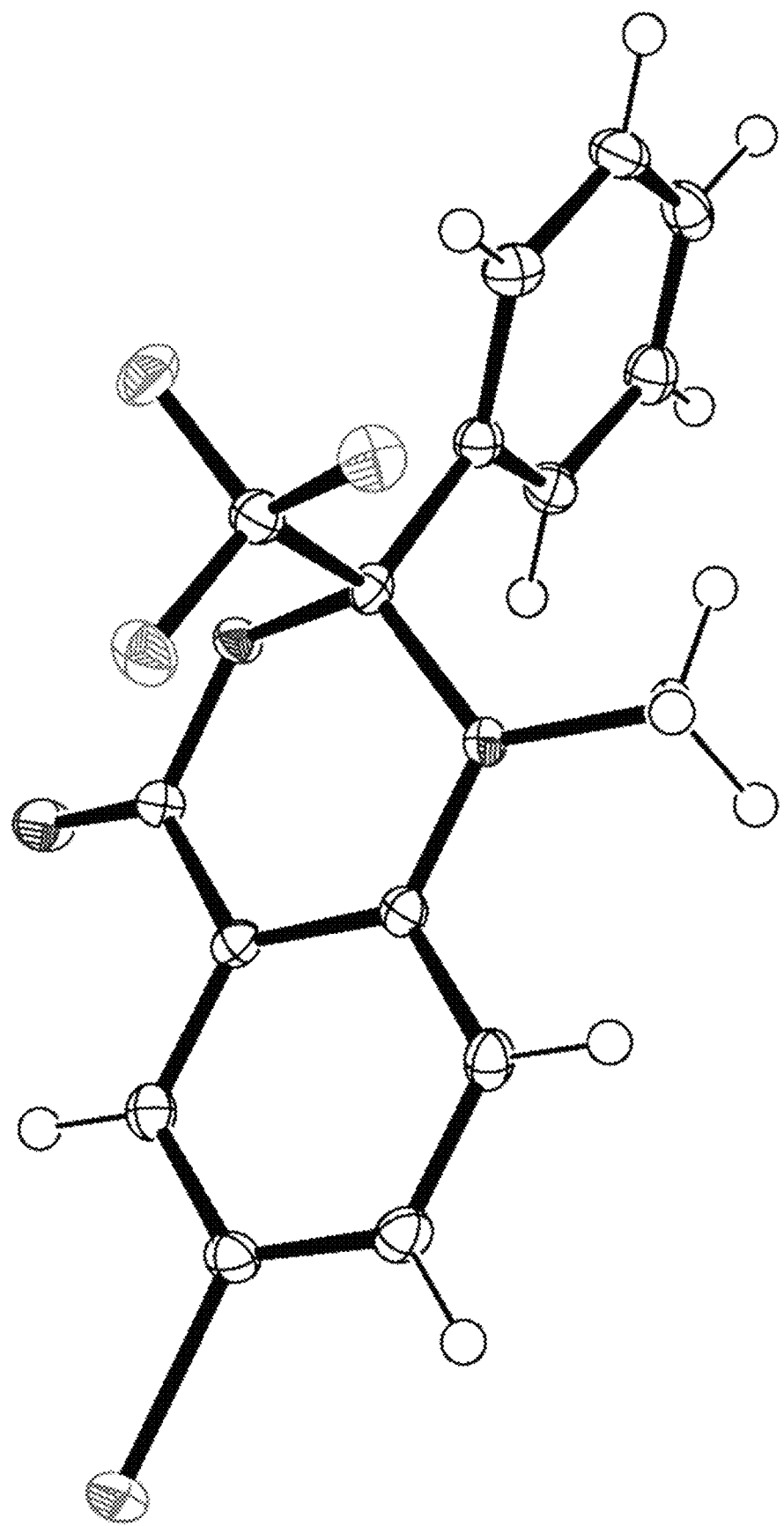
FIG. 11. X-ray crystal structure of 3n.

Scheme 2.
NHC screening for [4 + 2] cycloaddition. Conditions: 0.1 mmol 1a, 0.11 mmol 2a, 20 µmol NHC, 30 µmol KHMDS, 50 mg 4 Å MS, 0.1M in toluene. Absolute configuration of 3a was determined based on X-ray crystal analysis of 3n (see FIG. 11).[14]

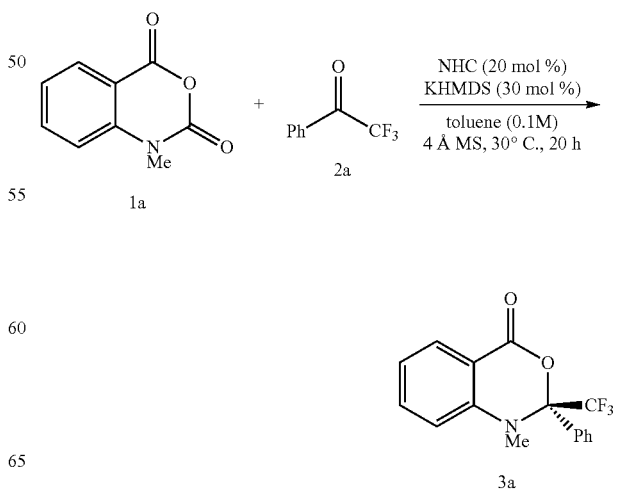

-continued

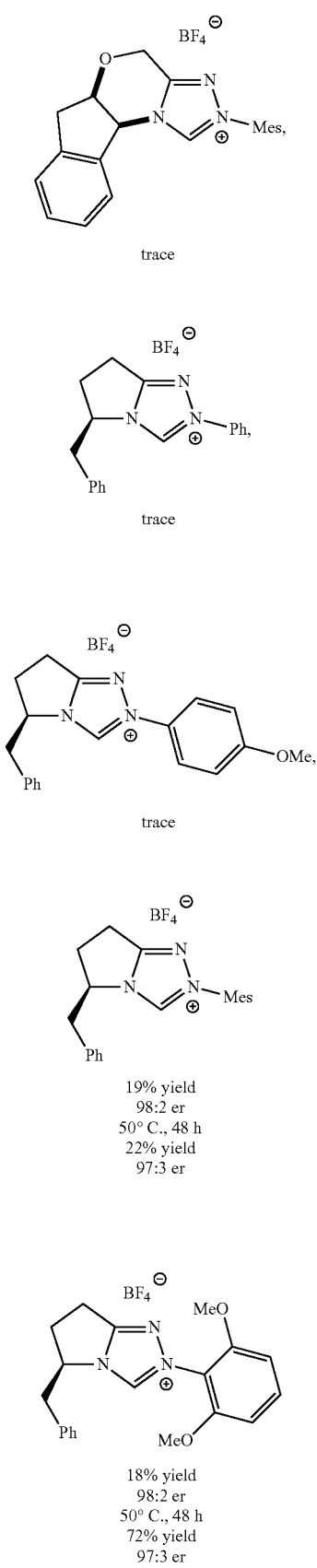

trace trace trace

19% yield
98:2 er
50° C., 48 h
22% yield
97:3 er

18% yield
98:2 er
50° C., 48 h
72% yield
97:3 er

TABLE 1

Substrate Scope[a] [a]Reaction scale
0.2 mmol. See the SI for reaction details.
Yields reported for compounds isolated. Er determined
by chiral-phase SFC analysis.
[b]Performed at 35° C.

1

2

E (20 mol %)
KHMDS (30 mol %)
───────────────→
toluene (0.1M)
4 Å MS, 50° C., 48 h

3

3a, 72%
97:3 er

R = MeO, 3b, 49%, 98:2 er
Me, 3c, 67%, 97:3 er
F, 3d, 68%, 98:2 er
Cl, 3e, 78%, 97:3 er
Br, 3f, 91%, 98:2 er

R = Me, 3g, 75%, 97:3 er
Cl, 3h, 73%, 95:5 er

TABLE 1-continued
Substrate Scope[a] [a]Reaction scale
0.2 mmol. See the SI for reaction details.
Yields reported for compounds isolated. Er determined
by chiral-phase SFC analysis.
[b]Performed at 35° C.
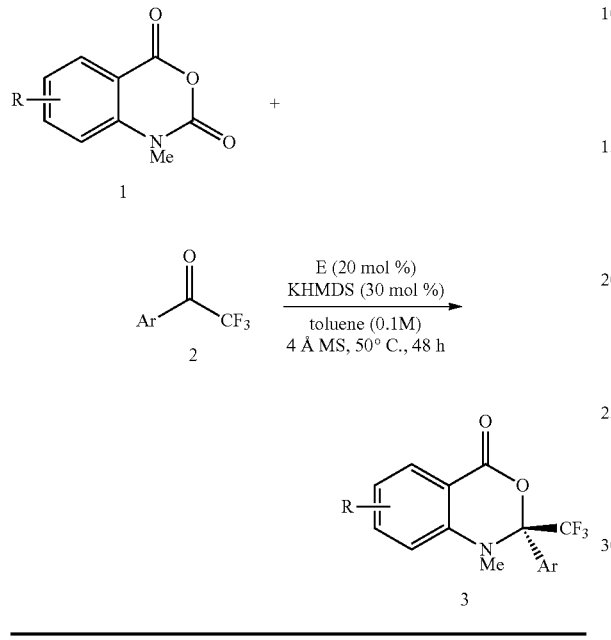
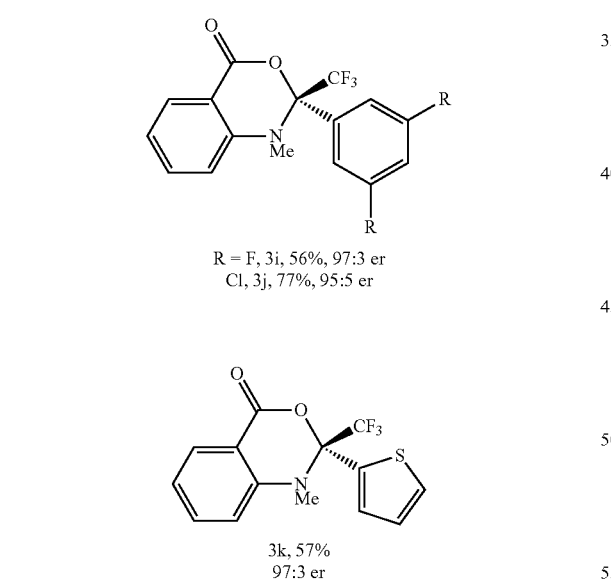
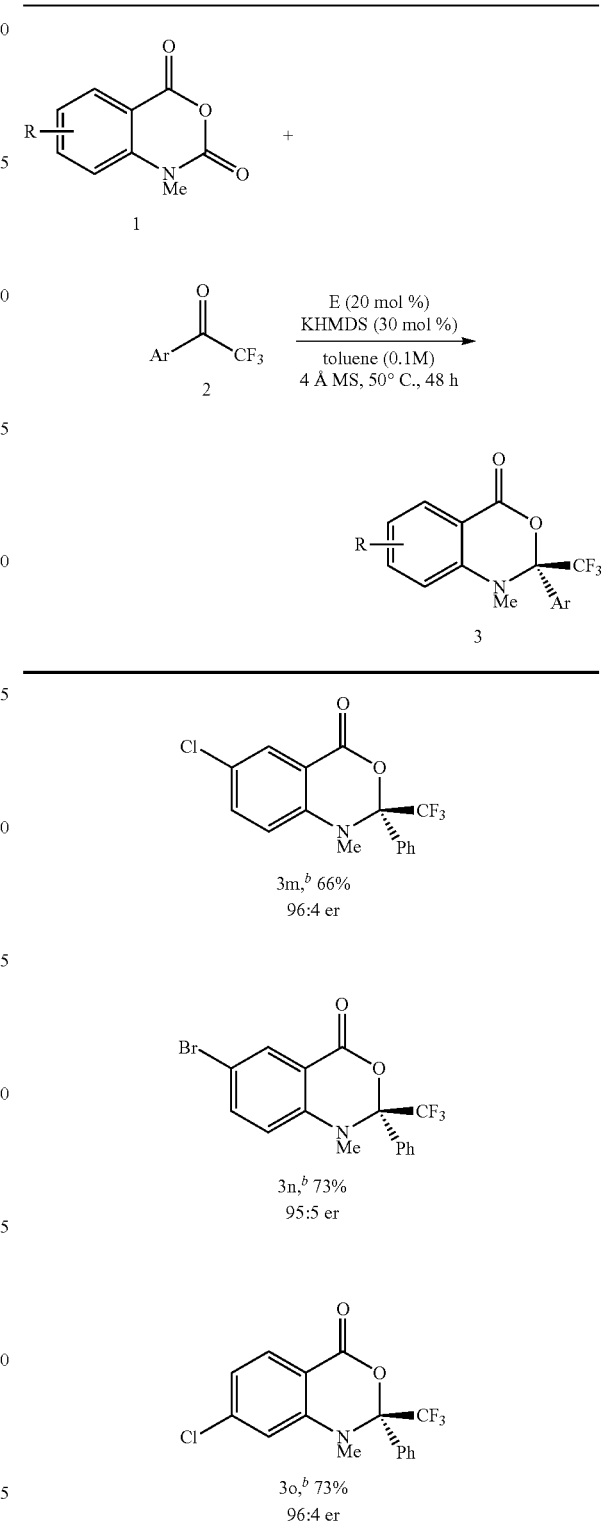

TABLE 1-continued

Substrate Scope[a] [a]Reaction scale
0.2 mmol. See the SI for reaction details.
Yields reported for compounds isolated. Er determined
by chiral-phase SFC analysis.
[b]Performed at 35° C.

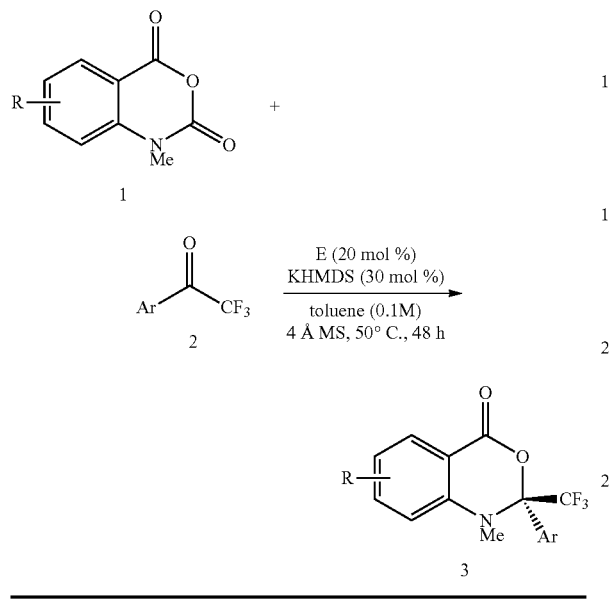

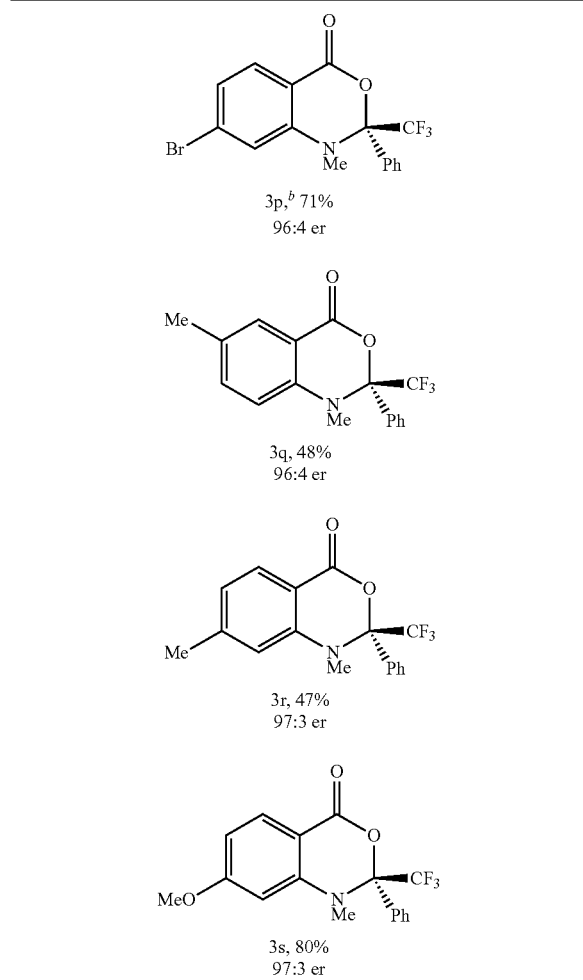

3p,[b] 71%
96:4 er 3q, 48%
96:4 er 3r, 47%
97:3 er 3s, 80%
97:3 er

TABLE 1-continued

Substrate Scope[a] [a]Reaction scale
0.2 mmol. See the SI for reaction details.
Yields reported for compounds isolated. Er determined
by chiral-phase SFC analysis.
[b]Performed at 35° C.

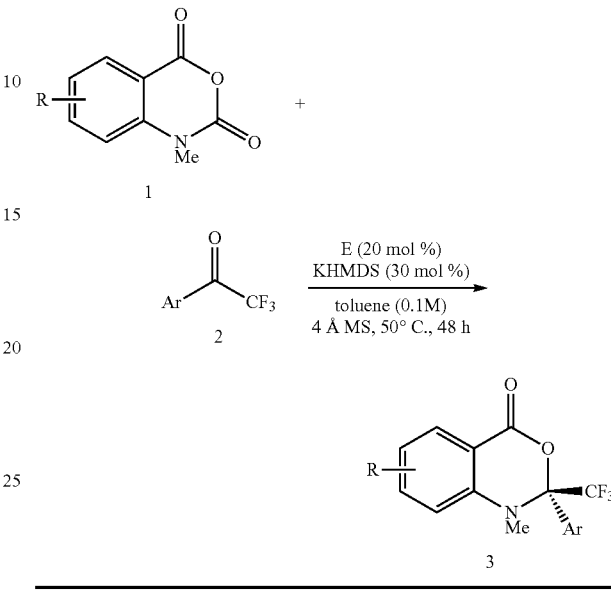

Instead of 2:

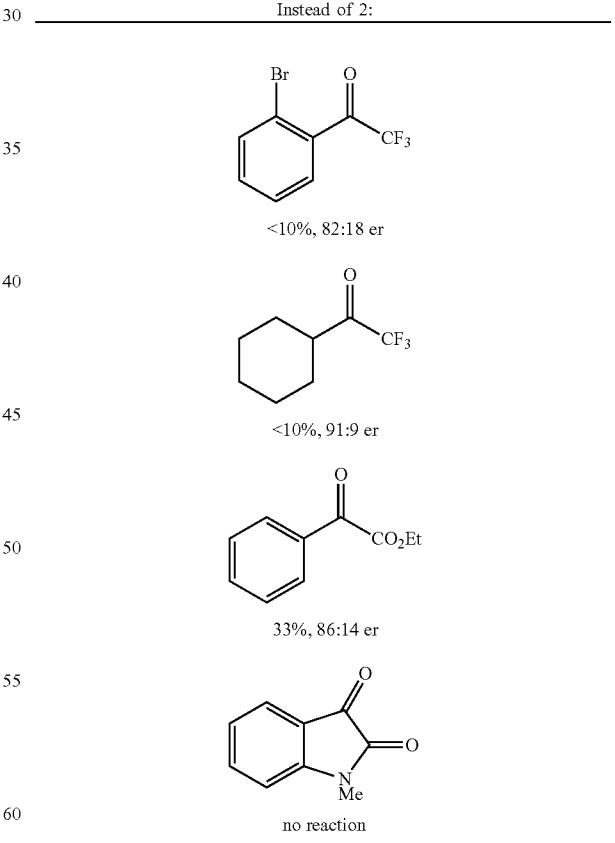

<10%, 82:18 er

<10%, 91:9 er

33%, 86:14 er no reaction

Potential catalytic pathways for the annulation are summarized in Scheme 3. The addition of catalyst E to anhydride 1a and subsequent release of $CO_2$ generates NHC-bound aza-o-QM intermediate I. Notably, we observed a mass correlating to intermediate I by high-resolution mass spectrometry (data not shown), which was somewhat surprising as aza-o-QMs are perceived to be highly reactive and transient species.[19] This key intermediate I can undergo a concerted [4+2] pathway or a stepwise Michael addition/acylation. In the [4+2] pathway, concerted addition of trifluoromethyl ketone 2 and the intermediate I via II affords the product 3. In the Michael addition/acylation pathway, a carbon-nitrogen bond is formed via III to generate intermediate IV, which undergoes O-acylation to regenerate the NHC E.

Gas-phase electronic energies of the TS fragments were compared to their corresponding ground-state structures.[22] Three important observations resulted: (1) The NHC-bound aza-o-QM complexes in both TSs were similarly distorted (ΔΔE=1.0 kcal/mol). (2) The trifluoromethyl ketone in the Major-TS, (S)-II was also similarly distorted compared to the Minor-TS, (R)-II by 1.8 kcal/mol. (3) Most importantly, the Major-TS, (S)-II was significantly more stabilized by the interaction energy than the Minor-TS, (R)-II (−33.6 kcal/mol versus −27.9 kcal/mol, respectively). We hypothesize

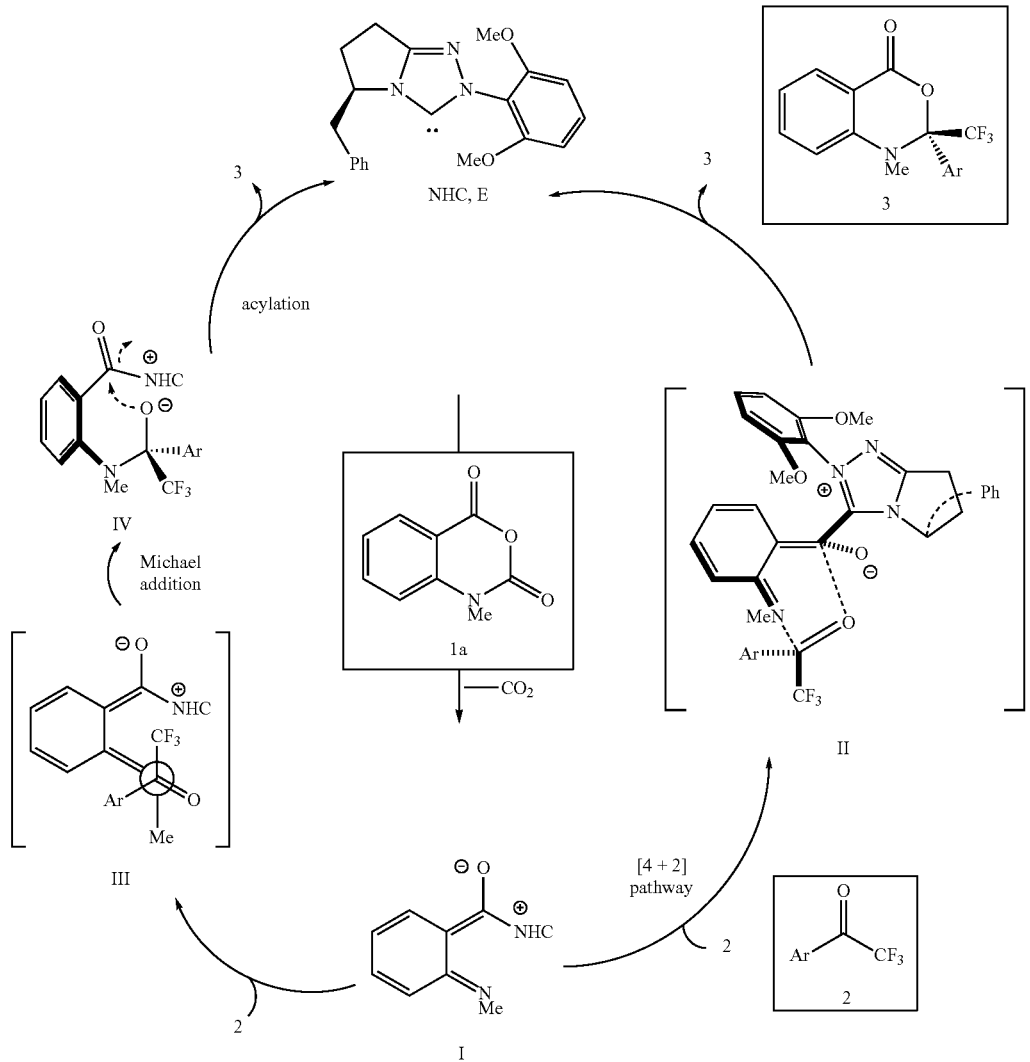

Scheme 3. Proposed reaction pathways.

To first gain insight into the origins of stereocontrol, we analyzed the cycloaddition transition structures involving catalyst E, anhydride 1a and trifluoromethyl ketone 2a with the ωB97XD/6-31G(d)/SMD(Toluene) level of theory at 323 K to match experimental conditions (FIG. 1).[20] The transition structure (TS) leading to the (S)-product ((S)-II) was predicted to be 3.5 kcal/mol more stable than that leading to the (R)-product ((R)-II). After these predictions were made, experiments indeed validated these predictions (% ee=94; $\Delta G^{\ddagger}_{exp}$=2.2 kcal/mol).

Distortion-interaction analyses of the two TSs were performed to elucidate the origins of selectivity (see the SI).[21]

this drastic difference in stabilizing interaction energy is due to a more favorable electrostatic interaction in the Major-TS, (S)-II over the Minor-TS, (R)-II. In (S)-II, the positively charged NHC-bound o-QM is stabilized by close proximity to the $CF_3$-group, bearing a partial negative charge. In contrast, (R)-II exhibits a relatively weak C—H . . . π interaction between the trifluoromethyl ketone phenyl group and the positively charged NHC complex (FIG. 1).

Figure 2:
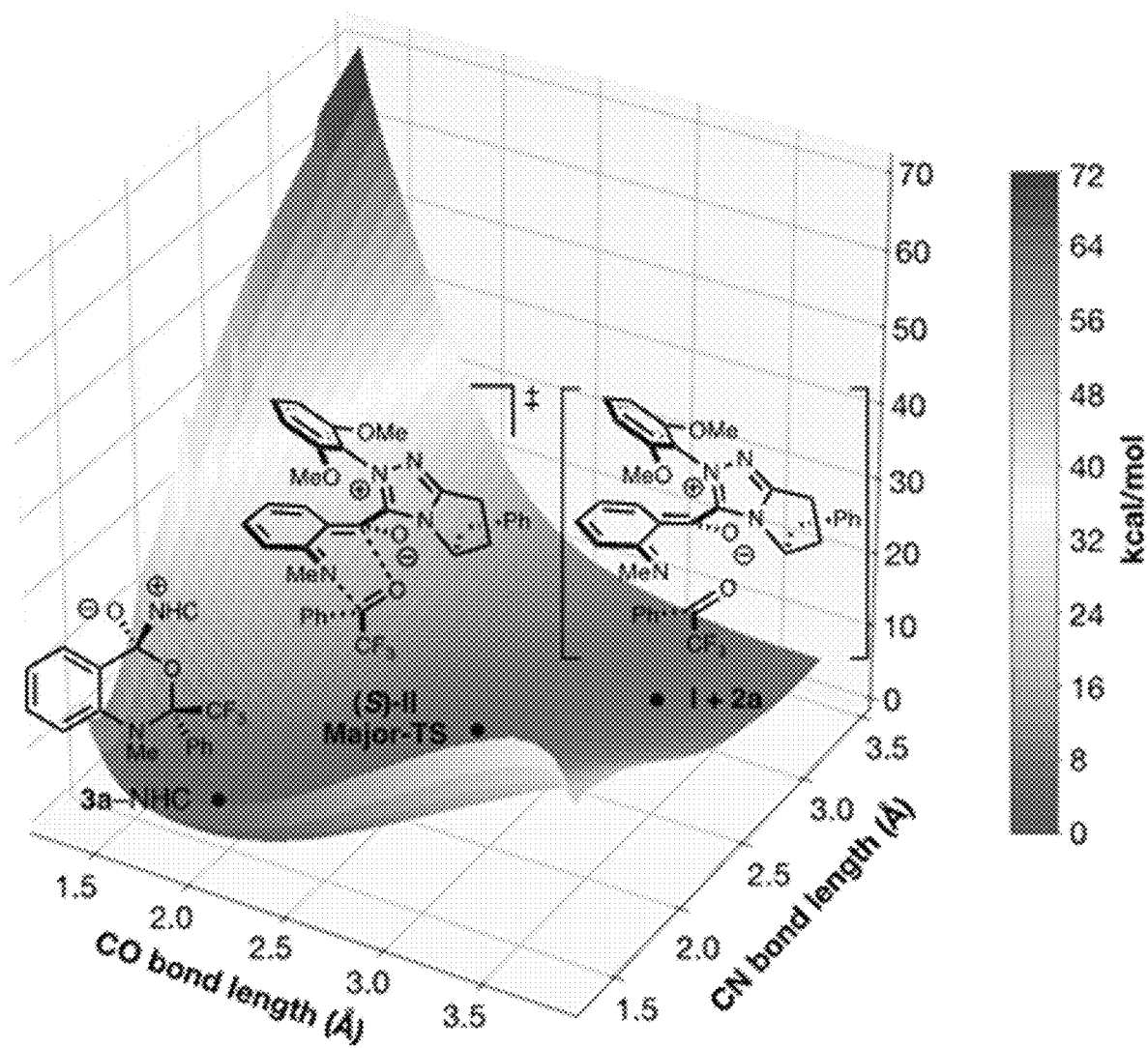

To better understand if the NHC-catalyzed annulation was concerted or stepwise (Scheme 3), we next computed the potential energy surface around the Major-TS, (S)-II (see FIG. 2). The energies were computed by fixing the distance between the nucleophilic nitrogen of the NHC-bound o-QM and the electrophilic carbon of trifluoromethyl ketone 2a (C—N bond) and varying distances corresponding to the second forming σ-bond. The surface shows that only one saddle point exists, suggesting a concerted process with no intervening intermediates[23]

Finally, the utility of these new enantioenriched dihydrobenzoxazinone products was explored (Scheme 4). The methylenation of 3a or 3n using the Tebbe reagent provided vinyl ether derivatives (4). A subsequent aza-Petasis-Ferrier rearrangement[24] gave the corresponding dihydroquinolone 5 with retention of chirality as determined by X-ray crystallography. This unprecedented sequence involving memory of chirality[25] presumably involves a Lewis acid-promoted ring opening to generate initially a single atropisomer of the Me$_2$AlCl-enolate intermediate (A1) from 4. The interconversion of this iminium enolate to atropisomer A2 is apparently slow relative to a rapid intramolecular Mannich reaction affording dihydroquinolones (5) with a CF$_3$-group at the C2 position. Trifluoromethyl groups are common in pharmaceutical molecules to improve metabolic stability, lipophilicity and permeability.[26] Therefore, we anticipate that these enantioenriched heterocycles with a CF$_3$-bearing stereocenter can be leveraged to explore new bioactive dihydroquinolone scaffolds.[27]

bearing stereocenter. Investigations involving these new NHC-bound intermediates and a variety of electrophile classes are ongoing.

REFERENCES

[1] For selected reviews, see: a) J. C. Powers, J. L. Asgian, Ö. D. Ekici, K. E. James, Chem. Rev. 2002, 102, 4639-4750; b) J. Ilaš, P. Š. Anderluh, M. S. Dolenc, D. Kikelj, Tetrahedron 2005, 61, 7325-7348; c) F. A. Macias, D. Marin, A. Oliveros-Bastidas, J. M. G. Molinillo, Nat. Prod. Rep. 2009, 26, 478-489.

[2] G. M. Coppola, J. Heterocyclic. Chem 1999, 36, 563-588.

[3] J. Wolfer, T. Bekele, C. J. Abraham, C. Dogo-Isonagie, T. Lectka, Angew. Chem. Int. Ed. 2006, 45, 7398-7400.

[4] X. Zhang, B. Xu, M.-H. Xu, Org. Chem. Front. 2016, 3, 944-948.

[5] J. L. Núñez-Rico, A. Vidal-Ferran, Org. Lett. 2013, 15, 2066-2069.

[6] a) M. Rueping, A. P. Antonchick, T. Theissmann, Angew. Chem. Int. Ed. 2006, 45, 6751-6755; b) L.-Q. Lu, Y. Li, K. Junge, M. Beller, J. Am. Chem. Soc. 2015, 137, 2763-2768.

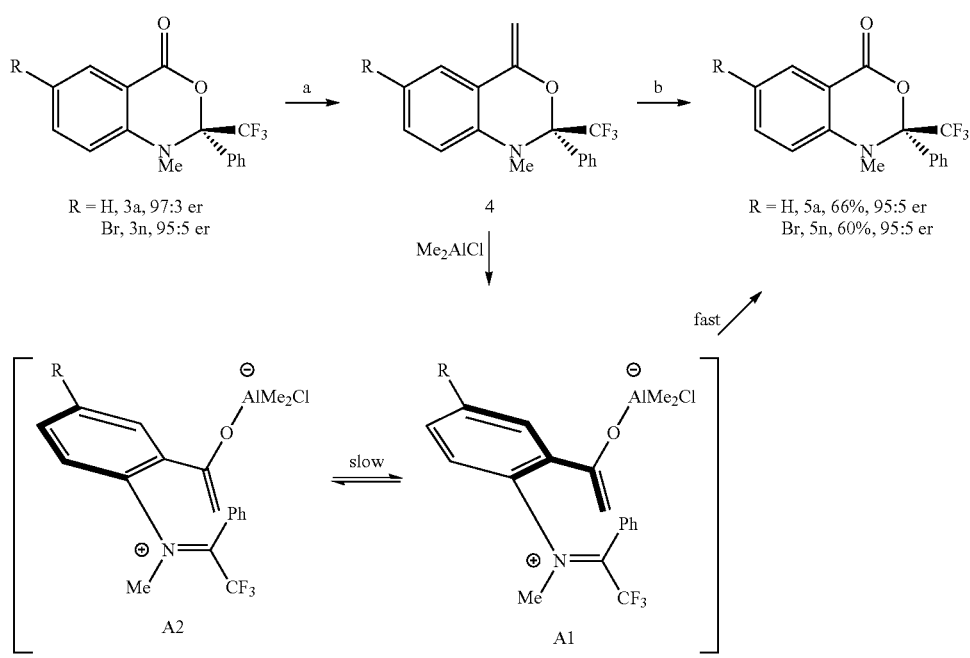

Scheme 4.
Transformation of 3. Conditions: a) Tebbe reagent, toluene/THF, -40° C. to 25° C.; (b) Me$_2$AlCl, CH$_2$Cl$_2$, -78° C.

An efficient asymmetric formal [4+2] cycloaddition of isatoic anhydride with trifluoromethyl ketones through NHC-mediated decarboxylative catalysis has been developed. This process generates an NHC-bound aza-o-QM as a key intermediate through liberation of carbon dioxide and avoids stoichiometric additives. Computations elucidated the origins of stereocontrol and revealed the concerted nature of the [4+2] process. This approach represents a highly versatile and selective transformation to provide enantioenriched dihydrobenzoxazin-4-ones with a CF$_3$-

[7] For selected examples on the synthesis of dihydrobenzoxazin-4-ones, see: a) X. Wang, J. Gallardo-Donaire, R. Martin, Angew. Chem. Int. Ed. 2014, 53, 11084-11087; b) N. Zhang, R. Cheng, D. Zhang-Negrerie, Y. Du, K. Zhao, J. Org. Chem. 2014, 79, 10581-10587; c) K. Patel, S. S. Deshmukh, D. Bodkhe, M. Mane, K. Vanka, D. Shinde, P. R. Rajamohanan, S. Nandi, R. Vaidhyanathan, S. H. Chikkali, J. Org. Chem. 2017, 82, 4342-4351; d) X. Qi, R. Li, H. P. Li, J. B. Peng, J. Ying, X. F. Wu, ChemCatChem 2018, 10, 3415-3418; e) P. Kumar, M. Gupta, V. Bahadur, V. S. Parmar, B. K. Singh, Eur. J. Org. Chem. 2018, 2018, 1552-1558.

[8] For reviews on NHC catalysis, see: a) D. Enders, O. Niemeier, A. Henseler, Chem. Rev. 2007, 107, 5606-5655; b) X. Bugaut, F. Glorius, Chem. Soc. Rev. 2012, 41, 3511-3522; c) H. U. Vora, P. Wheeler, T. Rovis, Adv. Synth. Catal. 2012, 354, 1617-1639; d) J. Izquierdo, G. E. Hutson, D. T. Cohen, K. A. Scheidt, Angew. Chem. Int. Ed. 2012, 51, 11686-11698; e) D. T. Cohen, K. A. Scheidt, Chem. Sci. 2012, 3, 53-57; f) J. Mahatthananchai, J. W. Bode, Acc. Chem. Res. 2014, 47, 696-707; g) M. N. Hopkinson, C. Richter, M. Schedler, F. Glorius, Nature 2014, 510, 485; h) R. S. Menon, A. T. Biju, V. Nair, Chem. Soc. Rev. 2015, 44, 5040-5052; i) D. M. Flanigan, F. Romanov-Michailidis, N. A. White, T. Rovis, Chem. Rev. 2015, 115, 9307-9387; j) M. H. Wang, K. A. Scheidt, Angew. Chem. Int. Ed. 2016, 55, 14912-14922.

[9] L. T. Shen, P. L. Shao, S. Ye, Adv. Synth. Catal. 2011, 353, 1943-1948.

[10] For a recent review on the transformations via azolium dienolate, see: X. Y. Chen, Q. Liu, P. Chauhan, D. Enders, Angew. Chem. Int. Ed. 2018, 57, 3862-3873.

[11] a) X. Chen, S. Yang, B. A. Song, Y. R. Chi, Angew. Chem. Int. Ed. 2013, 52, 11134-11137; b) J. Xu, S. Yuan, M. Miao, Org. Lett. 2016, 18, 3822-3825; c) D. Janssen-Müller, S. Singha, T. Olyschläger, C. G. Daniliuc, F. Glorius, Org. Lett. 2016, 18, 4444-4447; d) D.-F. Chen, T. Rovis, Synthesis 2017, 49, 293-298; e) J. Cheng, J. Sun, J. Yan, S. Yang, P. Zheng, Z. Jin, Y. R. Chi, J. Org. Chem. 2017, 82, 13342-13347; f) H. Wang, X. Chen, Y. Li, J. Wang, S. Wu, W. Xue, S. Yang, Y. R. Chi, Org. Lett. 2018, 20, 333-336; g) Y. Hu, D. Pan, L. Cong, Y. Yao, C. Yu, T. Li, C. Yao, ChemistrySelect 2018, 3, 1708-1712.

[12] For selected reviews on the o-QDMs, see: a) J. L. Segura, N. Martin, Chem. Rev. 1999, 99, 3199-3246; b) Y. Hiroto, O. Joji, K. Atsutaka, Bull. Chem. Soc. Jpn. 2010, 83, 199-219.

[13] X. Chen, H. Wang, K. Doitomi, C. Y. Ooi, P. Zheng, W. Liu, H. Guo, S. Yang, B.-A. Song, H. Hirao, Y. R. Chi, Nat. Commun. 2017, 8, 15598.

[14] CCDC 1876027 (3n) and CCDC 1888653 (5n) contain the supplementary crystallographic data for this paper. This data can be obtained free of charge from The Cambridge Crystalographic Data Centre.

[15] A. Levens, F. An, M. Breugst, H. Mayr, D. W. Lupton, Org. Lett. 2016, 18, 3566-3569.

[16] a) N. E. Wurz, C. G. Daniliuc, F. Glorius, Chem. Eur. J. 2012, 18, 16297-16301; b) F. Liu, X. Bugaut, M. Schedler, R. Frohlich, F. Glorius, Angew. Chem. Int. Ed. 2011, 50, 12626-12630.

[17] Ortho-subsitution presumably disfavors formation of intermediate II through steric effects as has been described before, for recent examples see: a) L. G. Borrego, R. Recio, M. Alcarranza, N. Khiar, I. Fernández, Adv. Synth. Catal. 2018, 360, 1273-1279; b) B. M. Trost, G. Mata, Angew. Chem. Int. Ed. 2018, 57, 12333-12337; c) Y. Zheng, Y. Tan, K. Harms, M. Marsch, R. Riedel, L. Zhang, E. Meggers, J. Am. Chem. Soc. 2017, 139, 4322-4325.

[18] Alkyl-trifluoromethyl ketones are not compatible under our reaction conditions, presumably due to keto/enol tautomerism as has been described previously (see ref 11d and 17).

[19] For selected reviews on the (aza-)o-QMs, see: a) A. A. Jaworski, K. A. Scheidt, J. Org. Chem. 2016, 81, 10145-10153; b) B. Yang, S. Gao, Chem. Soc. Rev. 2018, 47, 7926-7953.

[20] The original work was done using ωB97X/6-311++G (2df,p)//PBE/6-31G(d)/SMD(Toluene). However, the ground state and transition state structures were recomputed at the ωB97XD/6-31G(d)/SMD(Toluene) to account for dispersion interactions present in this system. For computational methodology, see: a) J. Chai, M. Head-Gordon, J. Chem. Phys. 2008, 10, 6615-6620; b) W. J. Hehre, R. Ditchfield and J. A. Pople, J. Chem. Phys. 1972, 56, 2257-2261; c) A. V. Marenich, C. J. Cramer and D. G. Truhlar, J. Phys. Chem. 2009, 113, 6378-6396.

[21] F. M. Bickelhaupt, K. N. Houk, Angew. Chem. Int. Ed. 2017, 56, 10070-10086.

[22] S. Chen, Y. Zheng, T. Cui, E. Meggers, K. N. Houk, J. Am. Chem. Soc. 2018, 140, 5146-5152.

[23] D. H. Ess, S. E. Wheeler, R. G. Iafe, L. Xu, N. Çelebi-Ölçcüm, K. N. Houk, Angew. Chem. Int. Ed. 2008, 47, 7592-7601.

[24] For selected reviews on the (aza)-Petasis-Ferrier rearrangement, see: a) A. B. Smith, R. J. Fox, T. M. Razler, Acc. Chem. Res. 2008, 41, 675-687; b) E. C. Minbiole, K. P. C. Minbiole, J. Antibiot. 2016, 69, 213; For selected examples on the (aza)-Petasis-Ferrier rearrangement, see: c) A. B. Smith, K. P. Minbiole, P. R. Verhoest, M. Schelhaas, J. Am. Chem. Soc. 2001, 123, 10942-10953; d) M. Terada, Y. Toda, J. Am. Chem. Soc. 2009, 131, 6354-6355; e) M. Terada, T. Komuro, Y. Toda, T. Korenaga, J. Am. Chem. Soc. 2014, 136, 7044-7057.

[25] For reviews on the memory of chirality, see: a) K. Fuji, T. Kawabata, Chem. Eur. J. 1998, 4, 373-376; b) T. Kawabata, K. Fuji, In Topics in Stereochemistry, Vol. 23; Denmark, S. E., Ed.; John Wiley & Sons Inc.: New York, 2003, 175-205; c) H. Zhao, D. C. Hsu, P. R. Carlier, Synthesis 2005, 1-16; For seminal examples on the memory of chirality, see: d) D. Seebach, D. Wasmuth, Angew. Chem Int. Ed. Engl. 1981, 20, 971-971; e) T. Kawabata, K. Yahiro, K. Fuji, J. Am. Chem. Soc. 1991, 113, 9694-9696; f) K. Fuji, T. Kawabata, Chem. Eur. J. 1998, 4, 373-376.

[26] For selected reviews on the CF3-containing drugs, see: a) J. Wang, M. Sanchez-Roselló, J. L. Aceña, C. del Pozo, A. E. Sorochinsky, S. Fustero, V. A. Soloshonok, H. Liu, Chem. Rev. 2014, 114, 2432-2506; b) W. Zhu, J. Wang, S. Wang, Z. Gu, J. L. Acerb, K. Izawa, H. Liu, V. A. Soloshonok, J. Fluorine Chem. 2014, 167, 37-54; c) Y. Zhou, J. Wang, Z. Gu, S. Wang, W. Zhu, J. L. Aceña, V. A. Soloshonok, K. Izawa, H. Liu, Chem. Rev. 2016, 116, 422-518.

[27] For selected reviews and examples on the synthesis of dihydroquinolones, see: a) A. R. Katritzky, S. Rachwal, B. Rachwal, Tetrahedron 1996, 52, 15031-15070; b) Y. Xia, Z.-Y. Yang, P. Xia, K. F. Bastow, Y. Tachibana, S.-C. Kuo, E. Hamel, T. Hackl, K.-H. Lee, J. Med. Chem. 1998, 41, 1155-1162; c) S. Y. Tamura, E. A. Goldman, P. W.

Bergum, J. E. Semple, Bioorg. Med. Chem. Lett. 1999, 9, 2573-2578; d) Y. Oshiro, Y. Sakurai, S. Sato, N. Kurahashi, T. Tanaka, T. Kikuchi, K. Tottori, Y. Uwahodo, T. Miwa, T. Nishi, J. Med. Chem. 2000, 43, 177-189; e) H. Zhao, A. Thurkauf, J. Braun, R. Brodbeck, A. Kieltyka, Bioorg. Med. Chem. Lett. 2000, 10, 2119-2122; f) B. Nammalwar, R. A. Bunce, Molecules 2014, 19, 204-232.

Example II—Supporting Information

General Information. All reactions were carried out under a nitrogen atmosphere in oven-dried glassware with magnetic stirring. THF, toluene, and DMF were purified by passage through a bed of activated alumina.[1] Purification of reaction products was carried out by flash chromatography using EM Reagent silica gel 60 (230-400 mesh). Analytical thin layer chromatography was performed on EM Reagent 0.25 mm silica gel 60-F plates. Visualization was accomplished with UV light and ceric ammonium nitrate stain or potassium permanganate stain followed by heating. $^1$H NMR spectra were recorded on AVANCE III 500 MHz w/direct cryoprobe (500 MHz) spectrometer and are reported in ppm using solvent as an internal standard (CDCl$_3$ at 7.26 ppm). Data are reported as (ap=apparent, s=singlet, d=doublet, t=apparent triplet, q=quartet, m=multiplet, b=broad; coupling constant(s) in Hz; integration.) Proton-decoupled $^{13}$C NMR spectra were recorded on an AVANCE III 500 MHz w/direct cryoprobe (125 MHz) spectrometer and are reported in ppm using solvent as an internal standard (CDCl$_3$ at 77.16 ppm). $^{19}$F NMR spectra were acquired at 26° C. on a 400 MHz Agilent 400MR-DD2 spectrometer equipped with a OneNMR probe and a 7600AS autosampler. Mass spectra were obtained on a WATERS Acquity-H UPLC-MS with a single quad detector (ESI) or on a Varian 1200 Quadrupole Mass Spectrometer and Micromass Quadro II Spectrometer (ESI). NHC F was prepared according to literature procedures.[2]

Synthesis and Characterization of NHC E

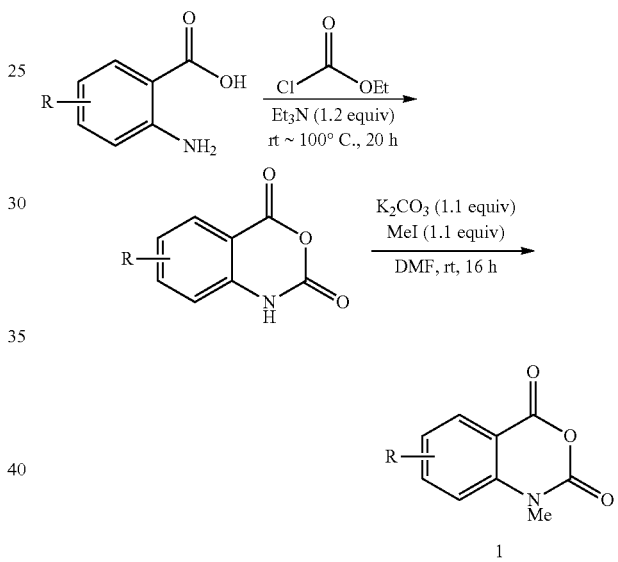

A round-bottom flask was charged with the triazolium chloride F (1.70 g, 4.57 mmol, 1.0 equiv) and NaBF$_4$ (1.51 g, 13.7 mmol, 3.0 equiv). CH$_2$Cl$_2$ (15.0 mL, 0.30 M) was then introduced and the heterogeneous mixture was vigorously stirred at room temperature. After 2 h, the mixture was filtered to remove excess salt. The filtrate was concentrated in vacuo. The resulting residue was purified by column chromatography on silica gel (CH$_2$Cl$_2$:MeOH=9:1) to give the corresponding triazolium tetrafluoroborate E (1.68 g, 87%) as a brown foamy solid.

Analytical data for NHC E. $^1$H NMR (500 MHz, CDCl$_3$) δ 9.56 (s, 1H), 7.49 (t, J=8.5 Hz, 1H), 7.32-7.24 (m, 3H), 7.22-7.14 (m, 2H), 6.69 (d, J=8.5 Hz, 2H), 5.48-5.36 (m, 1H), 3.86 (s, 6H), 3.34 (qd, J=14.0, 5.8 Hz, 2H), 3.06-2.89 (m, 2H), 2.74-2.57 (m, 2H). $^{13}$C{$^1$H} NMR (126 MHz, CDCl$_3$) δ 161.6, 155.6, 142.2, 134.4, 133.7, 129.7, 129.2, 127.8, 113.3, 104.5, 61.7, 56.6, 40.3, 31.8, 21.5. HRMS (ESI): Mass calculated for C$_{20}$H$_{22}$N$_3$O$_2$ [M]$^+$: 336.1707; found: 336.1707.

General Procedure for the Synthesis of N-Methyl Isatoic Anhydrides 1

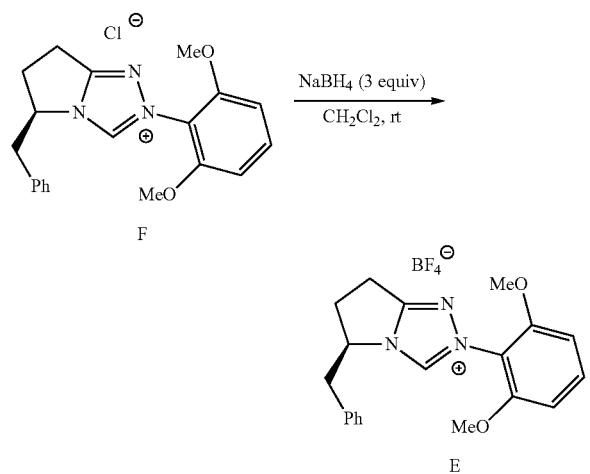

To an oven dried 20 mL reaction vial equipped with a magnetic stir bar was added the corresponding anthranilic acid (2 mmol) and 10 mL of ethyl chloroformate. Triethylamine (0.334 mL, 2.4 mmol) was added over 10 min, and the suspension stirred at ambient temperature for 18 h, then heated to 100° C. for 4 h. After completion of the reaction, the mixture was cooled and then diluted with 10 mL of toluene. The solid was collected by filtration and then recrystallized in ethanol to give the corresponding isatoic anhydride, which was used without further purification.[3]

To a 10 mL reaction vial equipped with a magnetic stir bar was added K$_2$CO$_3$ (1.2 equiv), MeI (1.2 equiv), the corresponding isatoic anhydride, and 5 mL of DMF. The solution was then stirred for 16 h. After completion of the reaction, the solution was poured into 15 mL of ice water and stirred for 10 min. The solid was collected by filtration and purified by silica gel column chromatography with ethyl acetate/hexanes (1:1) to give the corresponding N-methylated isatoic anhydride.[4]

Analytical Data for Substrates 1

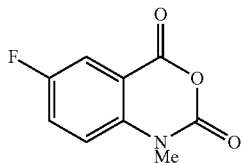

1l, white solid, 175.5 mg, 45% yield, Mp 148.2-153.8° C.
Analytical data for 1l: $^1$H NMR (500 MHz, CDCl$_3$) δ 7.81 (dd, J=7.5, 3.0 Hz, 1H), 7.51 (ddd, J=9.2, 7.6, 3.0 Hz, 1H), 7.20 (dd, J=9.1, 3.9 Hz, 1H), 3.58 (s, 3H). $^{13}$C{$^1$H} NMR (126 MHz, CDCl$_3$) δ 158.7 (d, J=247.1 Hz), 157.7 (d, J=3.4 Hz), 147.7, 138.6, 125.1 (d, J=23.7 Hz), 116.5 (d, J=24.4 Hz), 116.0 (d, J=7.4 Hz), 113.1 (d, J=8.0 Hz), 32.3. $^{19}$F NMR (376 MHz, CDCl$_3$) δ -117.0. FTIR (ATR) cm$^{-1}$ 1708, 1509, 1475, 1299, 1266, 1246, 1066, 1040, 930, 828, 772, 744, 669, 629. HRMS (ESI): Mass calculated for C$_9$H$_6$FNO$_3$ [M+H]: 196.0410; found: 196.0405.

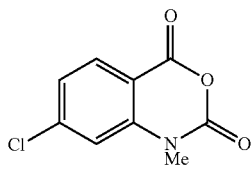

1o, tan solid, 177.2 mg, 42% yield, Mp 203.9-214.2° C.
Analytical data for 1o: $^1$H NMR (500 MHz, CDCl$_3$) δ 8.10 (d, J=8.4 Hz, 1H), 7.29 (dd, J=8.4, 1.7 Hz, 1H), 7.19 (d, J=1.7 Hz, 1H), 3.57 (s, 3H). $^{13}$C{$^1$H} NMR (126 MHz, CDCl$_3$) δ 157.7, 147.8, 144.2, 143.1, 132.2, 124.8, 114.4, 110.2, 32.1. FTIR: (ATR) cm$^{-1}$ 1773, 1718, 1701, 1603, 1584, 1332, 1304, 1030, 874, 765, 743, 678, 670. HRMS (ESI): Mass calculated for C$_9$H$_6$ClNO$_3$ [M+H]: 212.0114; found: 212.0112.

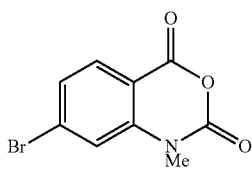 [SMILES: Cn1c(=O)oc(=O)c2ccc(Cl)cc21]

1p, tan solid, 183.6 mg, 36% yield, Mp 244.4-247.9° C.
Analytical data for 1p: $^1$H NMR (500 MHz, CDCl$_3$) δ 8.01 (d, J=8.4 Hz, 1H), 7.45 (dd, J=8.4, 1.6 Hz, 1H), 7.36 (d, J=1.4 Hz, 1H), 3.57 (s, 3H). $^{13}$C{$^1$H} NMR (126 MHz, CDCl$_3$) δ 157.9, 147.7, 142.9, 132.8, 132.1, 127.7, 117.3, 110.6, 32.1. FTIR (ATR) cm$^{-1}$ 1775, 1721, 1598, 1334, 1302, 1255, 1067, 1030, 874, 865, 764, 742, 677. HRMS (ESI): Mass calculated for C$_9$H$_6$BrNO$_3$ [M+H]: 255.9609; found: 255.9603.

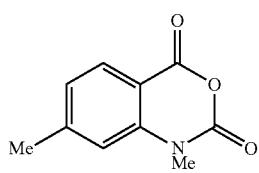 [SMILES: Cc1ccc2c(=O)oc(=O)n(C)c2c1]

1r, tan solid, 214.0 mg, 56% yield, Mp 179-184° C.
Analytical data for 1r: $^1$H NMR (500 MHz, CDCl$_3$) δ 8.02 (d, J=8.0 Hz, 1H), 7.11 (d, J=8.0 Hz, 1H), 6.97 (s, 1H), 3.56 (s, 3H), 2.51 (s, 3H). $^{13}$C NMR (126 MHz, CDCl$_3$) δ 158.5, 149.3, 148.4, 142.2, 130.8, 125.4, 114.2, 109.3, 31.9, 22.7. FTIR (ATR) cm$^{-1}$ 2360, 1763, 1715, 1616, 1588, 1458, 1428, 1341, 1309, 1066, 1032, 830, 767, 743, 684, 669. HRMS (ESI): Mass calculated for C$_{10}$H$_9$NO$_3$ [M+H]: 192.0661; found: 192.0650.

Optimization Tables for Decarboxylative Cycloaddition

TABLE 2

Reaction Conditions Screen

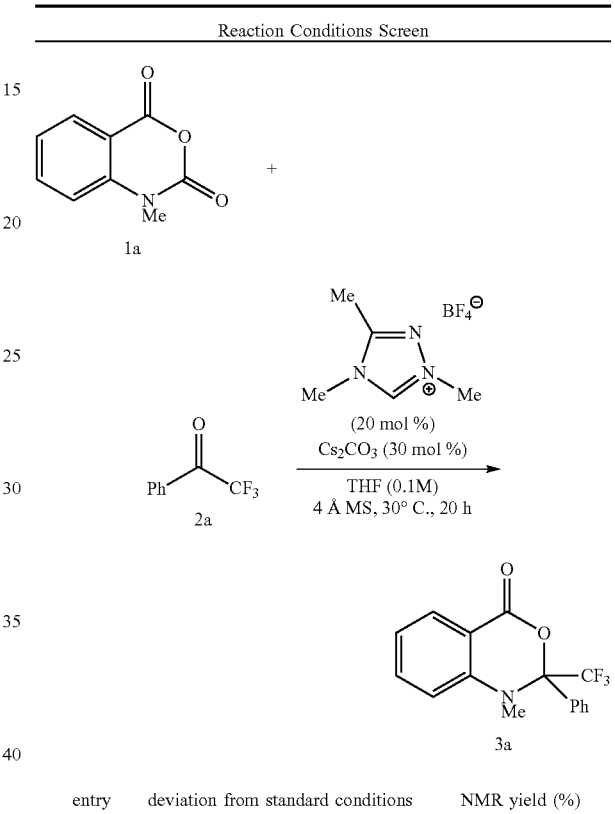

| entry | deviation from standard conditions | NMR yield (%) |
|---|---|---|
| 1 | none | 15 |
| 2 | 100 mol % of Cs$_2$CO$_3$ | 15 |
| 3 | w/o 4 Å MS | 5 |
| 4 | Reaction at 50° C. | 50 |
| 5 | KHMDS and toluene instead of Cs$_2$CO$_3$ and THF | 80 |

To an oven dried 5 mL reaction vial equipped with a magnetic stir bar under N$_2$ was added isatoic anhydride 1a (17.7 mg, 0.1 mmol), achiral triazolium (6.0 mg, 0.02 mmol), Cs$_2$CO$_3$ (9.8 mg, 0.03 mmol), and 50 mg of 4 Å molecular sieve (powder). The reaction vial was capped with a septum cap, removed from the drybox and put under positive N$_2$ pressure. Dry THF (1.0 mL) and 2,2,2-trifluoroacetophenone 2a (15.4 μL, 0.11 mmol) were then added and the heterogeneous mixture was stirred at 30° C. After 20 h, the entire crude reaction mixture was filtered over a pad of silica (4 cm) with ethyl acetate and concentrated under reduced pressure. The yields were determined by $^1$H NMR with 1,3,5-trimethylbenzene (4.6 μL, 0.033 mmol) as internal standard.

TABLE 3

Reaction Optimization

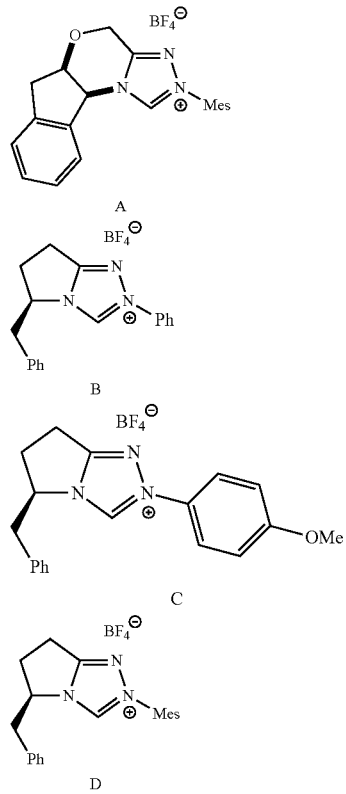

| entry | NHC | solvent | base | temp (° C.) | yield (%) | er |
|---|---|---|---|---|---|---|
| 1 | A | THF | $Cs_2CO_3$ | 50 | trace | — |
| 2 | B | THF | $Cs_2CO_3$ | 50 | trace | — |
| 3 | C | THF | $Cs_2CO_3$ | 50 | trace | — |
| 4 | D | THF | $Cs_2CO_3$ | 50 | 11 | 97:3 |
| 5 | D | DCE | $Cs_2CO_3$ | 50 | trace | — |
| 6 | D | MeCN | $Cs_2CO_3$ | 50 | no product | — |
| 7 | D | DMF | $Cs_2CO_3$ | 50 | no product | — |
| 8 | D | dioxane | $Cs_2CO_3$ | 50 | trace | — |
| 9 | D | PhCl | $Cs_2CO_3$ | 50 | <5 | — |
| 10 | D | toluene | $Cs_2CO_3$ | 50 | 13 | 98:2 |
| 11 | D | toluene | $Cs_2CO_3$ | 80 | <10 | — |
| 12 | D | toluene | $K_2CO_3$ | 50 | <5 | — |
| 13 | D | toluene | KOtBu | 50 | 15 | 98:2 |
| 14 | D | toluene | $Mg(OtBu)_2$ | 50 | trace | — |
| 15 | D | toluene | DBU | 50 | <10 | 97:3 |
| 16 | D | toluene | $iPr_2NEt$ | 50 | trace | — |
| 17 | D | toluene | DABCO | 50 | trace | — |
| 18 | D | toluene | TBD | 50 | 15 | 98:2 |
| 19 | D | toluene | KHMDS | 50 | 21 | 98:2 |
| 20 | D | toluene | KHMDS | 30 | 19 | 98:2 |
| 21 | E | toluene | KHMDS | 30 | 18 | 98:2 |
| 22 | F | toluene | KHMDS | 30 | 23 | 99:1 |
| 23 | D | toluene | KHMDS | 50 | 22 | 97:3 |
| 24 | E | toluene | KHMDS | 50 | 54 | 97:3 |
| 25 | E | toluene | KHMDS | 50, 48 h | 72 | 97:3 |
| 26 | F | toluene | KHMDS | 50, 48 h | 65 | 97:3 |

General Procedure for Decarboxylative Cycloaddition

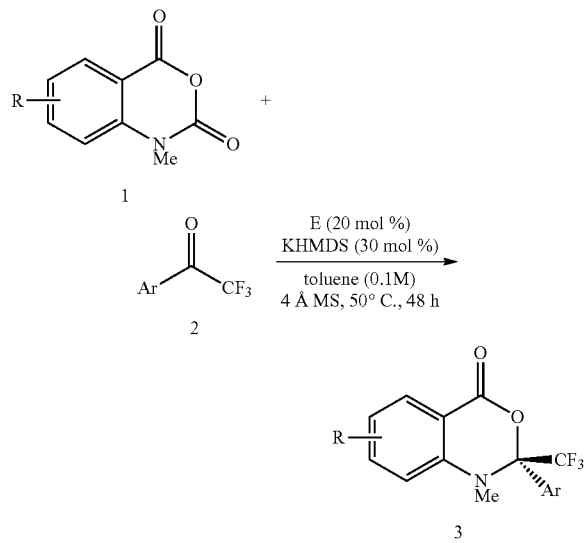

To an oven dried 5 mL reaction vial equipped with a magnetic stir bar under $N_2$ was added isatoic anhydride 1 (0.2 mmol), NHC E (16.9 mg, 0.04 mmol), KHMDS (12.0 mg, 0.06 mmol), and 100 mg of 4 Å molecular sieve (powder). The reaction vial was capped with a septum cap, removed from the drybox and put under positive $N_2$ pressure. Dry toluene (2.0 mL) and trifluoromethyl ketone 2 (0.22 mmol) were then added and the heterogeneous mixture was stirred at 50° C. After 48 h, the entire crude reaction mixture was filtered over a pad of silica (4 cm) with ethyl acetate and concentrated under reduced pressure. The crude was purified by silica gel column chromatography with ethyl acetate/hexane (1:4) to give the corresponding dihydrobenzoxazinone 3.

Analytical Data for Products 3

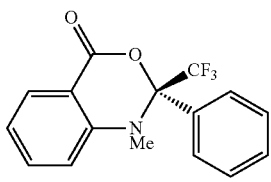 [SMILES: CN1c2ccccc2C(=O)O[C@@]1(c1ccccc1)C(F)(F)F]

3a, white solid, 44.4 mg, 72% yield, 97:3 er, Mp 96.4-100.9° C.

Analytical data for 3a: $^1$H NMR (500 MHz, CDCl$_3$) δ 7.99 (dd, J=7.8, 1.6 Hz, 1H), 7.73-7.67 (m, 2H), 7.59 (ddd, J=8.7, 7.3, 1.7 Hz, 1H), 7.51-7.44 (m, 3H), 7.01 (t, J=7.6 Hz, 1H), 6.93 (d, J=8.4 Hz, 1H), 3.00 (s, 3H). $^{13}$C{$^1$H} NMR (126 MHz, CDCl$_3$) δ 160.6, 147.5, 136.5, 134.8, 130.6, 130.4, 128.8, 128.0, 123.6 (q, J=293.9 Hz), 120.5, 114.1, 113.1, 94.0 (q, J=30.8 Hz), 35.5. $^{19}$F NMR (376 MHz, CDCl$_3$) δ −73.5. FTIR (ATR) cm$^{-1}$ 1737, 1610, 1492, 1354, 1159, 1114, 1065, 1037, 938, 754, 726, 699. HRMS (ESI): Mass calculated for $C_{16}H_{12}F_3NO_2$ [M+H]: 308.0898; found: 308.0890; Enantiomeric ratio was measured by chiral phase SFC (Chiralpak IC-3, 10% MeOH in CO$_2$, flow rate=2.5 mL/min, 210 nm): 1.65 min (major), 1.84 min (minor).

3b, pale yellow solid, 33.0 mg, 49% yield, 98:2 er, Mp 59.0-64.3° C.

Analytical data for 3b: $^1$H NMR (500 MHz, CDCl$_3$) δ 7.93 (dd, J=7.8, 1.6 Hz, 1H), 7.60-7.50 (m, 3H), 6.97-6.84 (m, 4H), 3.82 (s, 3H), 2.94 (s, 3H). $^{13}$C{$^1$H} NMR (126 MHz, CDCl$_3$) δ 161.0, 160.8, 147.5, 136.4, 130.5, 129.4, 126.6, 123.6 (q, J=292.4 Hz), 120.3, 114.1, 114.1, 113.1, 94.0 (q, J=30.6 Hz), 55.5, 35.4. $^{19}$F NMR (376 MHz, CDCl$_3$) δ −73.7. FTIR (ATR) cm$^{-1}$ 1732, 1489, 1169, 1160, 1105, 1058, 1024, 941, 850, 755, 725. HRMS (ESI): Mass calculated for $C_{17}H_{14}F_3NO_3$ [M+H]: 338.1004; found: 338.0094; Enantiomeric ratio was measured by chiral phase SFC (Chiralpak IC-3, 10% MeOH in CO$_2$, flow rate=2.5 mL/min, 250 nm): 2.06 min (major), 2.39 min (minor).

3c, white solid, 43.0 mg, 67% yield, 97:3 er, Mp 85.0-90.5° C.

Analytical data for 3c: $^1$H NMR (500 MHz, CDCl$_3$) δ 7.93 (dd, J=7.8, 1.6 Hz, 1H), 7.57-7.50 (m, 3H), 7.21 (d, J=8.1 Hz, 2H), 6.94 (t, J=7.6 Hz, 1H), 6.87 (d, J=8.4 Hz, 1H), 2.94 (s, 3H), 2.36 (s, 3H). $^{13}$C{$^1$H} NMR (126 MHz, CDCl$_3$) δ 160.7, 147.5, 140.6, 136.4, 131.8, 130.5, 129.5, 127.8, 123.6 (q, J=293.5 Hz), 120.3, 114.0, 113.1, 94.0 (q, J=30.5 Hz), 35.4, 21.3. $^{19}$F NMR (376 MHz, CDCl$_3$) δ −73.6. FTIR (ATR) cm$^{-1}$ 1743, 1602, 1478, 1343, 1159, 1106, 1055, 1033, 1022, 937, 848, 804, 760, 727, 693, 677. FIRMS (ESI): Mass calculated for $C_{17}H_{14}F_3NO_2$ [M+H]: 322.1055; found: 322.1044; Enantiomeric ratio was measured by chiral phase SFC (Chiralpak IC-3, 10% MeOH in CO$_2$, flow rate=2.5 mL/min, 250 nm): 1.80 min (major), 2.02 min (minor).

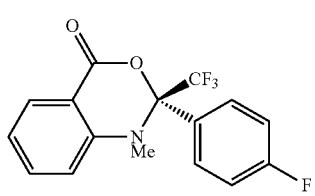 [SMILES: CN1c2ccccc2C(=O)O[C@@]1(c1ccc(F)cc1)C(F)(F)F]

3d, white solid, 44.4 mg, 68% yield, 98:2 er, Mp 93.8-95.6° C.

Analytical data for 3d: $^1$H NMR (500 MHz, CDCl$_3$) δ 7.93 (dd, J=7.8, 1.6 Hz, 1H), 7.64 (dd, J=8.6, 5.1 Hz, 2H), 7.55 (ddd, J=8.8, 7.4, 1.7 Hz, 1H), 7.15-7.07 (m, 2H), 6.97 (t, J=7.6 Hz, 1H), 6.90 (d, J=8.3 Hz, 1H), 2.97 (s, 3H). $^{13}$C{$^1$H} NMR (126 MHz, CDCl$_3$) δ 163.7 (d, J=251.4 Hz), 160.4, 147.4, 136.5, 130.8 (d, J=3.4 Hz), 130.6, 130.2 (d, J=8.3 Hz), 123.4 (q, J=292.7 Hz), 120.9, 116.0 (d, J=21.9 Hz), 114.6, 113.4, 93.7 (q, J=30.9 Hz), 35.7. $^{19}$F NMR (376 MHz, CDCl$_3$) δ −73.7, −110.0. FTIR (ATR) cm$^{-1}$ 1740, 1603, 1490, 1344, 1278, 1237, 1206, 1160, 1107, 1057, 1033, 940, 854, 821, 755, 725, 691, 678. HRMS (ESI): Mass calculated for C$_{16}$H$_{11}$F$_4$NO$_2$ [M+H]: 326.0804; found: 326.0804; Enantiomeric ratio was measured by chiral phase SFC (Chiralpak IG-3, 5% MeOH in CO$_2$, flow rate=2.5 mL/min, 230 nm): 2.04 min (major), 2.25 min (minor).

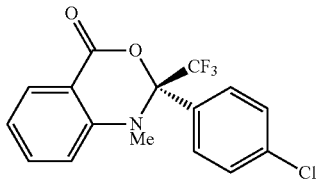 [SMILES: CN1c2ccccc2C(=O)O[C@@]1(c1ccc(Cl)cc1)C(F)(F)F]

3e, white solid, 53.1 mg, 78% yield, 97:3 er, Mp 75.6-77.7° C.

Analytical data for 3e: $^1$H NMR (500 MHz, CDCl$_3$) δ 7.93 (dd, J=7.9, 1.6 Hz, 1H), 7.59 (d, J=8.4 Hz, 2H), 7.55 (ddd, J=8.7, 7.4, 1.7 Hz, 1H), 7.42-7.35 (m, 2H), 6.98 (t, J=7.5 Hz, 1H), 6.91 (d, J=8.3 Hz, 1H), 2.98 (s, 3H). $^{13}$C{$^1$H} NMR (126 MHz, CDCl$_3$) δ 160.4, 147.4, 136.7, 136.6, 133.4, 130.6, 129.5, 129.1, 123.2 (q, J=292.7 Hz), 121.0, 114.8, 113.6, 93.6 (q, J=31.0 Hz), 35.8. $^{19}$F NMR (376 MHz, CDCl$_3$) δ −73.7. FTIR (ATR) cm$^{-1}$ 1742, 1604, 1490, 1345, 1207, 1185, 1166, 1098, 1057, 1040, 1018, 939, 851, 761, 737. HRMS (ESI): Mass calculated for C$_{16}$H$_{11}$ClF$_3$NO$_2$ [M+H]: 342.0509; found: 342.0499; Enantiomeric ratio was measured by chiral phase SFC (Chiralpak IG-3, 5% MeOH in CO$_2$, flow rate=2.5 mL/min, 210 nm): 3.00 min (major), 3.30 min (minor).

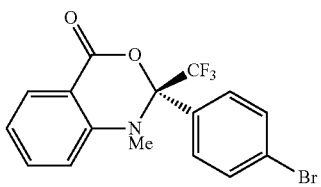 [SMILES: CN1c2ccccc2C(=O)O[C@@]1(c1ccc(Br)cc1)C(F)(F)F]

3f, white solid, 70.5 mg, 91% yield, 98:2 er, Mp 76.1-79.4° C.

Analytical data for 3f: $^1$H NMR (500 MHz, CDCl$_3$) δ 77.93 (dd, J=7.8, 1.6 Hz, 1H), 7.61-7.47 (m, 5H), 6.98 (t, J=7.6 Hz, 1H), 6.91 (d, J=8.4 Hz, 1H), 2.98 (s, 3H). $^{13}$C{$^1$H} NMR (126 MHz, CDCl$_3$) δ 160.2, 147.3, 136.4, 133.8, 132.0, 130.5, 129.6, 124.9, 123.1 (q, J=292.6 Hz), 120.9, 114.7, 113.5, 93.6 (q, J=30.9 Hz), 35.8. $^{19}$F NMR (376 MHz, CDCl$_3$) δ −73.7. FTIR (ATR) cm$^{-1}$ 1746, 1489, 1347, 1162, 1109, 1052, 1038, 1010, 936, 854, 811, 757, 729, 674. HRMS (ESI): Mass calculated for C$_{16}$H$_{11}$BrF$_3$NO$_2$ [M+H]: 386.0004; found: 385.0001; Enantiomeric ratio was measured by chiral phase SFC (Chiralpak IG-3, 20% MeOH in CO$_2$, flow rate=2.5 mL/min, 210 nm): 1.72 min (major), 1.85 min (minor).

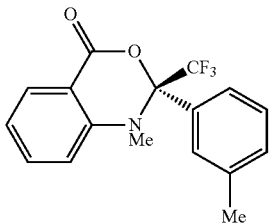 [SMILES: Cc1cccc([C@@]2(C(F)(F)F)OC(=O)c3ccccc3N2C)c1]

3g, white oily solid, 48.4 mg, 75% yield, 97:3 er

Analytical data for 3g: NMR (500 MHz, CDCl$_3$) δ 7.95 (dd, J=7.8, 1.7 Hz, 1H), 7.54 (ddd, J=8.7, 7.3, 1.7 Hz, 1H), 7.46 (s, 1H), 7.43 (d, J=8.0 Hz, 1H), 7.30 (t, J=7.7 Hz, 1H), 7.24 (d, J=7.6 Hz, 1H), 6.95 (t, J=7.6 Hz, 1H), 6.87 (d, J=8.4 Hz, 1H), 2.93 (s, 3H), 2.37 (s, 3H). $^{13}$C{$^1$H} NMR (126 MHz, CDCl$_3$) δ 160.6, 147.4, 138.7, 136.4, 134.7, 131.2, 130.5, 128.6, 124.9, 124.9, 123.7 (q, J=294.1 Hz), 120.3, 113.9, 112.9, 94.1 (q, J=30.5 Hz), 35.4, 21.7. $^{19}$F NMR (376 MHz, CDCl$_3$) δ −73.4. FTIR (ATR) cm$^-$ 1742, 1608, 1490, 1154, 1112, 1062, 1041, 956, 750, 736, 724, 704, 678. HRMS (ESI): Mass calculated for C$_{17}$H$_{14}$F$_3$NO$_2$ [M+H]: 322.1055; found: 322.1053; Enantiomeric ratio was measured by chiral phase SFC (Chiralpak IC-3, 10% MeOH in CO$_2$, flow rate=2.5 mL/min, 250 nm): 1.62 min (major), 1.81 min (minor).

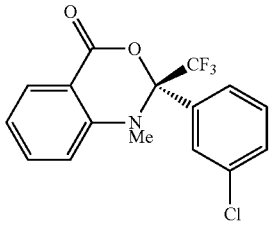 [SMILES: CN1c2ccccc2C(=O)O[C@@]1(c1cccc(Cl)c1)C(F)(F)F]

3h, white solid, 49.9 mg, 73% yield, 95:5 er, Mp 126.5-130.2° C.

Analytical data for 3h: $^1$H NMR (500 MHz, CDCl$_3$) δ 7.94 (dd, J=7.8, 1.6 Hz, 1H), 7.65 (s, 1H), 7.59-7.53 (m, 2H), 7.44-7.40 (m, 1H), 7.36 (t, J=7.9 Hz, 1H), 6.99 (t, J=7.5 Hz, 1H), 6.91 (d, J=8.3 Hz, 1H), 2.97 (s, 3H). $^{13}$C{$^1$H} NMR (126 MHz, CDCl$_3$) δ 160.2, 147.3, 136.8, 136.6, 135.1, 130.8, 130.6, 130.1, 128.4, 126.2, 123.3 (q, J=293.3 Hz), 121.0, 114.7, 113.4, 93.5 (q, J=31.2 Hz), 35.8. $^{19}$F NMR (376 MHz, CDCl$_3$) δ −73.6. FTIR (ATR) cm$^{-1}$ 1739, 1483, 1348, 1162, 1109, 1061, 1016, 999, 950, 886, 795, 763, 740, 725, 705, 691. HRMS (ESI): Mass calculated for C$_{16}$H$_{11}$ClF$_3$NO$_2$ [M+H]: 342.0509; found: 342.0499; Enantiomeric ratio was measured by chiral phase SFC (Chiralpak IG-3, 5% MeOH in CO$_2$, flow rate=2.5 mL/min, 230 nm): 2.63 min (major), 3.20 min (minor).

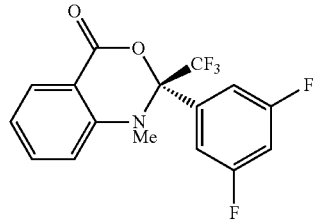 [SMILES: CN1c2ccccc2C(=O)O[C@@]1(c1cc(F)cc(F)c1)C(F)(F)F]

3i, pale yellow solid, 38.2 mg, 56% yield, 97:3 er, Mp 97.5-100.4° C.

Analytical data for 3i: $^1$H NMR (500 MHz, CDCl$_3$) δ 7.94 (dd, J=7.8, 1.6 Hz, 1H), 7.57 (ddd, J=8.7, 7.4, 1.7 Hz, 1H), 7.23-7.17 (m, 2H), 7.02 (t, J=7.6 Hz, 1H), 6.95 (d, J=8.3 Hz, 1H), 6.89 (tt, J=8.5, 2.3 Hz, 1H), 3.03 (s, 3H). $^{13}C\{^{1}H\}$ NMR (126 MHz, CDCl$_3$) δ 163.0 (dd, J=250.7, 12.2 Hz), 159.9, 147.3, 138.6 (t, J=8.7 Hz), 136.7, 130.7, 122.9 (q, J=292.6 Hz), 121.6, 115.4, 113.9, 112.89-110.93 (m), 106.3 (t, J=25.0 Hz), 93.1 (q, J=31.6 Hz), 36.2. $^{19}F$ NMR (376 MHz, CDCl$_3$) δ -73.8, -107.3. FTIR (ATR) cm$^{-1}$ 1746, 1603, 1491, 1296, 1185, 1169, 1152, 1124, 1063, 1023, 972, 847, 751, 739, 724, 674. HRMS (ESI): Mass calculated for C$_{16}$H$_{10}$F$_5$NO$_2$ [M+H]: 344.0710; found: 344.0699; Enantiomeric ratio was measured by chiral phase SFC (Chiralpak IG-3, 5% MeOH in CO$_2$, flow rate=2.5 mL/min, 230 nm): 1.43 min (major), 1.60 min (minor).

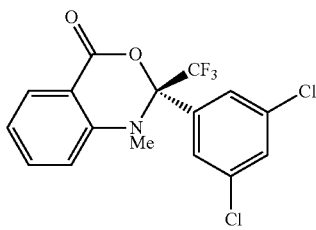 [SMILES: CN1c2ccccc2C(=O)O[C@@]1(c1cc(Cl)cc(Cl)c1)C(F)(F)F]

3j, white solid, 57.7 mg, 77% yield, 95:5 er, Mp 104.8-109.2° C.

Analytical data for 3j: $^{1}H$ NMR (500 MHz, CDCl$_3$) δ 7.95 (dd, J=7.9, 1.6 Hz, 1H), 7.58 (ddd, J=8.7, 7.3, 1.5 Hz, 1H), 7.54 (s, 2H), 7.45-7.41 (m, 1H), 7.03 (t, J=7.6 Hz, 1H), 6.94 (d, J=8.3 Hz, 1H), 3.00 (s, 3H). $^{13}C\{^{1}H\}$ NMR (126 MHz, CDCl$_3$) δ 159.8, 147.2, 138.2, 136.8, 135.8, 130.9, 130.7, 126.8, 122.9 (q, J=292.7 Hz), 121.6, 115.3, 113.7, 93.1 (q, J=31.4 Hz), 36.2. $^{19}F$ NMR (376 MHz, CDCl$_3$) δ -73.6. FTIR (ATR) cm$^{-1}$ 1744, 1297, 1225, 1184, 1120, 1062, 1038, 988, 965, 867, 800, 768, 744, 732, 705, 679. HRMS (ESI): Mass calculated for C$_{16}$H$_{10}$Cl$_2$F$_3$NO$_2$ [M+H]: 376.0119; found: 376.0110; Enantiomeric ratio was measured by chiral phase SFC (Chiralpak IG-3, 5% MeOH in CO$_2$, flow rate=2.5 mL/min, 230 nm): 2.19 min (major), 2.46 min (minor).

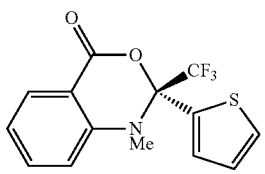 [SMILES: CN1c2ccccc2C(=O)O[C@@]1(c1cccs1)C(F)(F)F]

3k, pale yellow solid, 35.7 mg, 57% yield, 97:3 er, Mp 88.7-90.6° C.

Analytical data for 3k: $^{1}H$ NMR (500 MHz, CDCl$_3$) δ 7.96 (dd, J=7.8, 1.7 Hz, 1H), 7.56 (ddd, J=8.7, 7.3, 1.7 Hz, 1H), 7.47 (dd, J=5.1, 1.2 Hz, 1H), 7.40-7.36 (m, 1H), 7.02 (dd, J=5.1, 3.7 Hz, 1H), 6.97 (t, J=7.6 Hz, 1H), 6.87 (d, J=8.4 Hz, 1H), 2.99 (s, 3H). $^{13}C\{^{1}H\}$ NMR (126 MHz, CDCl$_3$) δ 159.9, 147.0, 137.7, 136.6, 130.6, 129.6, 128.9, 126.8, 123.4 (q, J=294.5 Hz), 120.4, 113.5, 112.4, 92.3 (q, J=31.9 Hz), 34.9. $^{19}F$ NMR (376 MHz, CDCl$_3$) δ -74.7. FTIR (ATR) cm$^{-1}$ 1747, 1491, 1200, 1181, 1162, 1108, 1054, 1039, 888, 751, 718, 694, 677. HRMS (ESI): Mass calculated for C$_{14}$H$_{10}$F$_3$NO$_2$S [M+H]: 314.0463; found: 314.0452; Enantiomeric ratio was measured by chiral phase SFC (Chiralpak IC-3, 10% MeOH in CO$_2$, flow rate=2.5 mL/min, 230 nm): 1.95 min (major), 2.22 min (minor).

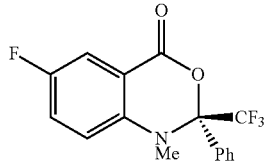

3l, white oily solid, 50.8 mg, 78% yield, 96:4 er

Analytical data for 3l: $^{1}H$ NMR (500 MHz, CDCl$_3$) δ 7.63 (d, J=7.6 Hz, 2H), 7.60 (dd, J=8.0, 3.1 Hz, 1H), 7.45-7.37 (m, 3H), 7.26 (td, J=8.5, 3.1 Hz, 1H), 6.92 (dd, J=9.0, 4.1 Hz, 1H), 2.99 (s, 3H). $^{13}C\{^{1}H\}$ NMR (126 MHz, CDCl$_3$) δ 160.0 (d, J=3.1 Hz), 157.1 (d, J=242.5 Hz), 144.3, 134.5, 130.5, 128.8, 128.0, 123.8 (d, J=23.5 Hz), 123.2 (q, J=292.3 Hz), 117.6 (d, J=7.2 Hz), 116.1 (d, J=24.2 Hz), 115.5 (d, J=7.8 Hz), 94.4 (q, J=30.8 Hz), 36.7. $^{19}F$ NMR (376 MHz, CDCl$_3$) δ -73.6, -1211 FTIR (ATR) cm$^{-1}$ 1739, 1500, 1273, 1183, 1167, 1154, 1057, 1021, 939, 914, 892, 815, 790, 740, 726, 698. FIRMS (ESI): Mass calculated for C$_{16}$H$_{11}$F$_4$NO$_2$ [M+H]: 326.0804; found: 322.1045; Enantiomeric ratio was measured by chiral phase SFC (Chiralpak IC-3, 5% MeOH in CO$_2$, flow rate=2.5 mL/min, 210 nm): 1.64 min (major), 1.85 min (minor).

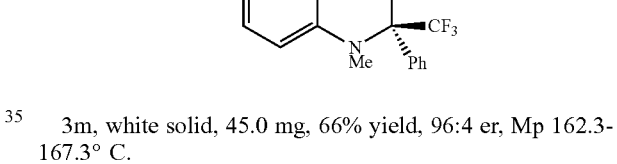

3m, white solid, 45.0 mg, 66% yield, 96:4 er, Mp 162.3-167.3° C.

Analytical data for 3m: $^{1}HNMR$ (500 MHz, CDCl$_3$) δ 7.90 (d, J=2.6 Hz, 1H), 7.62 (d, J=7.3 Hz, 2H), 7.50-7.39 (m, 4H), 6.84 (d, J=8.8 Hz, 1H), 2.95 (s, 3H). $^{13}C\{^{1}H\}$ NMR (126 MHz, CDCl$_3$) δ 159.5, 146.0, 136.3, 134.3, 130.7, 129.9, 128.9, 127.9, 125.9, 123.4 (q, J=293.3 Hz), 115.8, 114.2, 94.1 (q, J=30.8 Hz), 35.7. $^{19}F$ NMR (376 MHz, CDCl$_3$) δ -73.5. FTIR (ATR) cm$^{-1}$ 1740, 1492, 1183, 1167, 1154, 1056, 1026, 939, 819, 775, 727, 713, 695, 675. HRMS (ESI): Mass calculated for C$_{16}$H$_{11}$ClF$_3$NO$_2$ [M+H]: 342.0509; found: 326.0794; Enantiomeric ratio was measured by chiral phase SFC (Chiralpak IC-3, 5% MeOH in CO$_2$, flow rate=2.5 mL/min, 210 nm): 2.47 min (major), 3.25 min (minor).

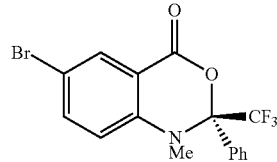 [SMILES: CN1c2ccc(Cl)cc2C(=O)O[C@@]1(c1ccccc1)C(F)(F)F]

3n, white solid, 55.2 mg, 73% yield, 95:5 er Mp 155.0-159.9° C.

Analytical data for 3n: $^{1}H$ NMR (500 MHz, CDCl$_3$) δ 8.03 (d, J=2.4 Hz, 1H), 7.65-7.57 (m, 3H), 7.48-7.38 (m, 3H), 6.76 (d, J=8.8 Hz, 1H), 2.92 (s, 3H). $^{13}C\{^{1}H\}$ NMR (126 MHz, CDCl$_3$) δ 159.3, 146.3, 139.1, 134.3, 132.9, 130.7, 129.0, 127.9, 123.4 (q, J=293.3 Hz), 115.9, 114.5, 112.7, 94.1 (q, J=30.8 Hz), 35.6. $^{19}F$ NMR (376 MHz, CDCl₃) δ −73.6. FTIR (ATR) cm⁻¹ 1738, 1604, 1490, 1207, 1183, 1165, 1153, 1114, 1063, 1021, 938, 819, 767, 726, 705, 696, 667. FIRMS (ESI): Mass calculated for C₁₆H₁₁BrF₃NO₂ [M+H]: 386.0004; found: 385.9997; Enantiomeric ratio was measured by chiral phase SFC (Chiralpak IC-3, 10% MeOH in CO₂, flow rate=2.5 mL/min, 230 nm): 1.93 min (major), 2.46 min (minor).

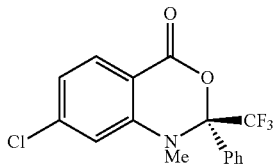

3o, oily yellow solid, 49.6 mg, 73% yield, 96:4 er

Analytical data for 3o: ¹H NMR (500 MHz, CDCl₃) δ 7.88 (d, J=8.3 Hz, 1H), 7.67-7.59 (m, 2H), 7.50-7.40 (m, 3H), 6.92 (dd, J=8.3, 1.8 Hz, 1H), 6.85 (d, J=1.8 Hz, 1H), 2.91 (s, 3H). ¹³C{¹H} NMR (126 MHz, CDCl₃) δ 159.6, 148.0, 143.0, 134.2, 131.9, 130.7, 129.0, 127.8, 123.6 (q, J=293.8 Hz), 120.5, 113.5, 110.7, 94.1 (q, J=30.7 Hz), 35.1. ¹⁹F NMR (376 MHz, CDCl₃) δ −73.5. FTIR (ATR) cm⁻¹ 1742, 1603, 1422, 1164, 1098, 1056, 1033, 941, 762, 730, 695. HRMS (ESI): Mass calculated for C₁₆H₁₁ClF₃NO₂ [M+H]: 342.0509; found: 342.0492; Enantiomeric ratio was measured by chiral phase SFC (Chiralpak IC-3, 5% MeOH in CO₂, flow rate=2.5 mL/min, 210 nm): 2.31 min (major), 2.84 min (minor).

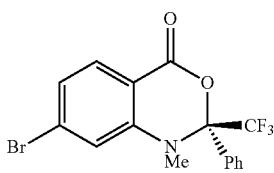 [SMILES: CN1c2cc(Cl)ccc2C(=O)O[C@@]1(c1ccccc1)C(F)(F)F]

3p, waxy white solid, 54.8 mg, 71% yield, 96:4 er

Analytical data for 3p: ¹H NMR (500 MHz, CDCl₃) δ 7.79 (d, J=8.3 Hz, 1H), 7.63 (d, J=7.4 Hz, 2H), 7.51-7.40 (m, 3H), 7.08 (dd, J=8.3, 1.6 Hz, 1H), 7.03 (d, J=1.5 Hz, 1H), 2.91 (s, 3H). ¹³C{¹H} NMR (126 MHz, CDCl₃) δ 159.8, 147.9, 134.2, 131.9, 131.7, 130.7, 129.0, 127.8, 123.6 (q, J=293.8 Hz), 123.5, 116.5, 111.1, 94.0 (q, J=30.9 Hz), 35.1. ¹⁹F NMR (376 MHz, CDCl₃) δ −73.5. FTIR: (ATR) cm⁻¹ 1737, 1596, 1280, 1207, 1176, 1132, 1113, 1082, 1056, 765, 734, 701. HRMS (ESI): Mass calculated for C₁₆H₁₁BrF₃NO₂ [M+H]: 386.0004; found: 385.9997; Enantiomeric ratio was measured by chiral phase SFC (Chiralpak IC-3, 5% MeOH in CO₂, flow rate=2.5 mL/min, 250 nm): 2.63 min (major), 3.29 min (minor).

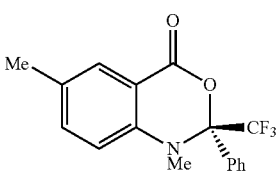 [SMILES: Cc1ccc2c(c1)C(=O)O[C@@](c1ccccc1)(C(F)(F)F)N2C]

3q, white solid, 31.0 mg, 48% yield, 96:4 er, Mp 126.3-129.1° C.

Analytical data for 3q: ¹H NMR (500 MHz, CDCl₃) δ 7.73 (d, J=2.1 Hz, 1H), 7.68-7.61 (m, 2H), 7.44-7.37 (m, 3H), 7.34 (dd, J=8.4, 2.2 Hz, 1H), 6.82 (d, J=8.4 Hz, 1H), 2.96 (s, 3H), 2.28 (s, 3H). ¹³C{¹H} NMR (126 MHz, CDCl₃) δ 161.0, 145.6, 137.3, 135.0, 130.5, 130.3, 130.3, 128.7, 128.0, 123.4 (q, J=292.6 Hz), 115.2, 113.8, 94.1 (q, J=30.5 Hz), 36.1, 20.4. ¹⁹F NMR (376 MHz, CDCl₃) δ −73.5. FTIR (ATR) cm⁻¹ 1734, 1509, 1165, 1120, 1057, 1023, 938, 828, 785, 776, 737, 724, 693, 663. FIRMS (ESI): Mass calculated for C₁₇H₁₄F₃NO₂ [M+H]: 322.1055; found: 322.1045; Enantiomeric ratio was measured by chiral phase SFC (Chiralpak IC-3, 10% MeOH in CO₂, flow rate=2.5 mL/min, 210 nm): 1.73 min (major), 2.03 min (minor)

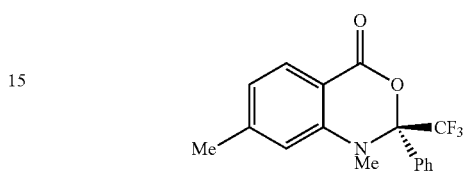

3r, white solid, 30.2 mg, 47% yield, 97:3 er, Mp 125.7-127.8° C.

Analytical data for 3r: ¹H NMR (500 MHz, CDCl₃) δ 7.82 (d, J=7.9 Hz, 1H), 7.68-7.60 (m, 2H), 7.46-7.37 (m, 3H), 6.77 (d, J=7.9 Hz, 1H), 6.68 (s, 1H), 2.94 (s, 3H), 2.39 (s, 3H). ¹³C{¹H} NMR (126 MHz, CDCl₃) δ 160.6, 147.8, 147.5, 135.0, 130.5, 130.4, 128.8, 127.9, 123.6 (q, J=293.5 Hz), 121.7, 114.4, 110.5, 94.0 (q, J=30.5 Hz), 35.4, 22.6. ¹⁹F NMR (376 MHz, CDCl₃) δ −73.5. FTIR (ATR) cm⁻¹ 1730, 1616, 1295, 1210, 1194, 1174, 1133, 1114, 1054, 768, 749, 725, 704. FIRMS (ESI): Mass calculated for C₁₇H₁₄F₃NO₂ [M+H]: 322.1055; found: 322.1045; Enantiomeric ratio was measured by chiral phase SFC (Chiralpak IC-3, 10% MeOH in CO₂, flow rate=2.5 mL/min, 250 nm): 2.01 min (major), 2.22 min (minor).

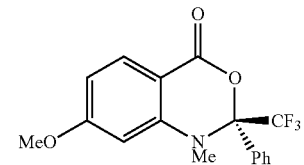 [SMILES: COc1ccc2c(c1)N(C)[C@](c1ccccc1)(C(F)(F)F)OC2=O]

3s, colorless oily solid, 54.0 mg, 80% yield, 97:3 er

Analytical data for 3s: ¹H NMR (500 MHz, CDCl₃) δ 7.89 (d, J=8.7 Hz, 1H), 7.67-7.57 (m, 2H), 7.47-7.38 (m, 3H), 6.48 (dd, J=8.7, 2.3 Hz, 1H), 6.30 (d, J=2.2 Hz, 1H), 3.87 (s, 3H), 2.92 (d, J=1.0 Hz, 3H). ¹³C{¹H} NMR (126 MHz, CDCl₃) δ 166.4, 160.2, 149.2, 135.0, 132.9, 130.4, 128.8, 127.9, 123.7 (q, J=293.8 Hz), 106.2, 105.7, 99.0, 93.9 (q, J=30.5 Hz), 55.7, 35.2. ¹⁹F NMR (376 MHz, CDCl₃) δ −73.5. LRMS (ESI): Mass calculated for C₁₇H₁₄F₃NO₃ [M+H]: 338.1; found: 338.1; Enantiomeric ratio was measured by chiral phase SFC (Chiralpak IC-3, 5% MeOH in CO₂, flow rate=2.5 mL/min, 230 nm): 4.59 min (major), 5.39 min (minor).

Decarboxylative Cycloaddition of Unsuccessful Substrates

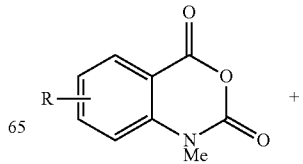

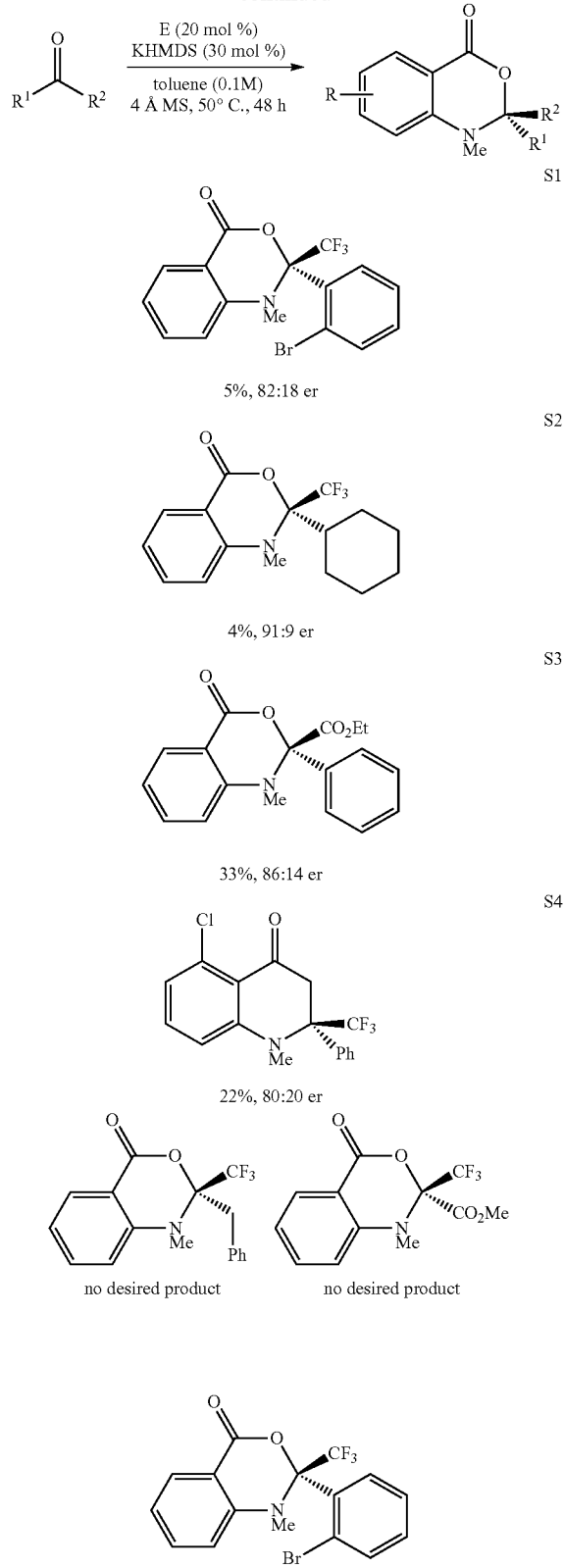

(td, J=7.7, 1.4 Hz, 1H), 7.34 (td, J=7.7, 1.6 Hz, 1H), 6.98-6.89 (m, 1H), 6.75 (d, J=8.3 Hz, 1H), 2.78 (s, 3H). $^{13}C\{^1H\}$ NMR (126 MHz, CDCl$_3$) δ 159.9, 146.5, 136.7, 132.1, 131.8, 130.7, 129.2, 129.2 (q, J=4.5 Hz), 127.4, 123.9 (q, J=297.0 Hz), 123.5, 119.1, 111.9, 110.2, 94.6 (q, J=30.9 Hz), 33.7. $^{19}F$ NMR (376 MHz, CDCl$_3$) δ −75.0. FTIR (ATR) cm$^1$ 1742, 1493, 1181, 1159, 1127, 1112, 1076, 1038, 938, 748, 725, 686, 675. HRMS (ESI): Mass calculated for C$_{16}$H$_{11}$BrF$_3$NO$_2$ [M+H]: 386.0004; found: 385.9982; Enantiomeric ratio was measured by chiral phase SFC (Chiralpak IG-3, 10% MeOH in CO$_2$, flow rate=2.5 mL/min, 210 nm): 3.01 min (major), 3.76 min (minor).

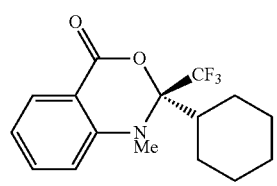 [SMILES: CN1c2ccccc2C(=O)O[C@@]1(C1CCCCC1)C(F)(F)F]

S2, yellow oily solid, 2.5 mg, 4% yield, 91:9 er.
Analytical data for S2: $^1$H NMR (500 MHz, CDCl$_3$) δ 7.92 (dd, J=7.8, 1.7 Hz, 1H), 7.50 (ddd, J=8.8, 7.3, 1.8 Hz, 1H), 6.87 (t, J=7.5 Hz, 1H), 6.74 (d, J=8.5 Hz, 1H), 2.98 (s, 3H), 2.29 (tt, J=11.8, 3.2 Hz, 1H), 1.97-1.82 (m, 3H), 1.77-1.58 (m, 3H), 1.43 (qd, J=12.7, 3.2 Hz, 1H), 1.35-1.15 (m, 3H). $^{13}C\{^1H\}$ NMR (126 MHz, CDCl$_3$) δ 160.2, 148.3, 136.6, 130.6, 124.4 (q, J=298.6 Hz), 118.9, 111.5, 109.9, 94.9 (q, J=28.3 Hz), 41.4, 31.9, 26.3, 26.2, 26.1, 25.9, 25.5. $^{19}F$ NMR (376 MHz, CDCl$_3$) δ −72.4. LRMS (ESI): Mass calculated for C$_{16}$H$_{18}$F$_3$NO$_2$ [M+H]: 314.1; found: 314.1; Enantiomeric ratio was measured by chiral phase SFC (Chiralpak IG-3, 10% MeOH in CO$_2$, flow rate=2.5 mL/min, 210 nm): 1.91 min (major), 2.15 min (minor).

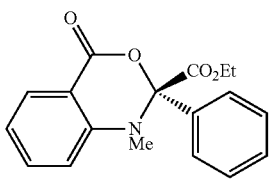

S3, colorless oily solid, 20.4 mg, 33% yield, 86:14 er
Analytical data for S3: $^1$H NMR (500 MHz, CDCl$_3$) δ 8.00 (dd, J=7.8, 1.6 Hz, 1H), 7.67-7.60 (m, 2H), 7.58-7.51 (m, 1H), 7.49-7.43 (m, 3H), 6.99 (t, J=7.6 Hz, 1H), 6.92 (d, J=8.4 Hz, 1H), 4.21 (q, J=7.1 Hz, 2H), 2.80 (s, 3H), 1.12 (t, J=7.1 Hz, 3H). $^{13}C\{^1H\}$ NMR (126 MHz, CDCl$_3$) δ 169.6, 162.6, 149.1, 136.2, 134.7, 130.9, 130.4, 128.9, 127.6, 120.6, 114.5, 113.8, 96.2, 62.8, 35.1, 14.1. LRMS (ESI): Mass calculated for C$_{18}$H$_{17}$NO$_4$ [M+H]: 312.1; found: 312.1; Enantiomeric ratio was measured by chiral phase SFC (Chiralpak IC-3, 30% MeOH in CO$_2$, flow rate=2.5 mL/min, 250 nm): 1.96 min (major), 2.61 min (minor).

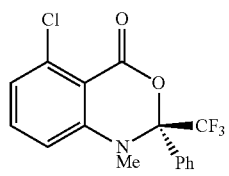 [SMILES: CN1c2cccc(Cl)c2C(=O)O[C@@]1(c1ccccc1)C(F)(F)F]

S4, waxy white solid, 15.1 mg, 22% yield, 80:20 er
Analytical data for S4: $^1$H NMR (500 MHz, CDCl$_3$) δ 7.58 (d, J=7.8 Hz, 2H), 7.44-7.33 (m, 4H), 6.98 (dd, J=8.1, 1.0 Hz, 1H), 6.82 (dd, J=8.5, 0.9 Hz, 1H), 3.00 (s, 3H). $^{13}C\{^1H\}$ NMR (126 MHz, CDCl$_3$) δ 157.2, 149.8, 137.5, 135.5, 134.5, 130.6, 128.9, 128.0, 124.2, 123.2 (q, J=292.1 Hz), 113.8, 112.0, 93.4 (q, J=30.9 Hz), 36.5. $^{19}F$ NMR (376 MHz, CDCl$_3$) 5-73.5. FTIR (ATR) cm$^{-1}$ 1748, 1594, 1479, 1183, 1156, 1124, 1091, 1063, 938, 791, 728, 721, 698, 621. HRMS (ESI): Mass calculated for $C_{16}H_{11}C_1F_3NO_2$ [M+H]: 342.0509; found: 342.0479; Enantiomeric ratio was measured by chiral phase SFC (Chiralpak IC-3, 5% MeOH in CO$_2$, flow rate=2.5 mL/min, 210 nm): 3.42 min (major), 4.12 min (minor).

Synthesis of Dihydroquinolinone 5

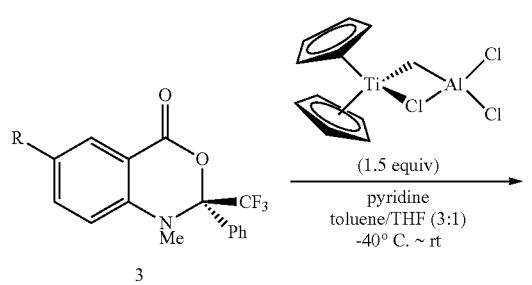

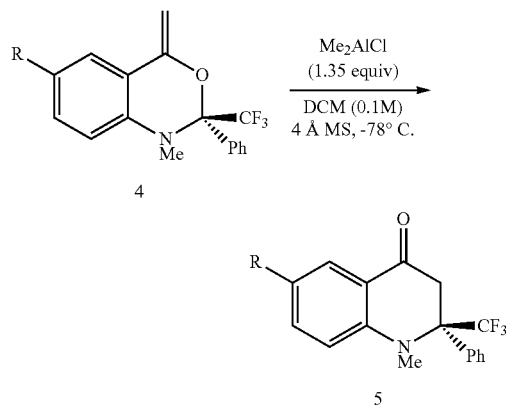

The dihydrobenzoxazinone 3 (0.2 mmol, 1.0 equiv) was dissolved in 0.8 mL of toluene-THF (3:1) and 2.0 μL of pyridine and cooled to −40° C. A solution of Tebbe reagent (0.60 mL, 1.5 equiv, 0.5 M in toluene) was added dropwise. The reaction was stirred at the same temperature for 30 min and then allowed to warm to ambient temperature for 2 h. The reaction was quenched by the addition of 0.15 mL of 15% aqueous NaOH solution and diluted with excess diethyl ether, dried with sodium sulfate, and filtered through a Celite pad. The crude vinyl ether 4 was used without purification.

To a solution of 4 in CH$_2$Cl$_2$ (2.0 mL) at −78° C. was added dimethylaluminum chloride (0.3 mL, 1.35 equiv, 0.9 M in heptane). The crude mixture was stirred for 10 min at the same temperature and then warmed to ambient temperature. The reaction was quenched with saturated NaHCO$_3$ solution (5 mL) and then extracted by CH$_2$Cl$_2$ (3×20 mL). The organic solution was dried with sodium sulfate and concentrated under reduced pressure. The crude was purified by silica gel column chromatography with ethyl acetate/hexane (1:19) or dichloromethane/hexane (1:2) to give the corresponding dihydroquinolinone 5.

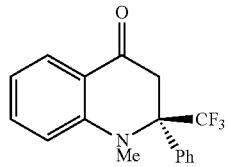 [SMILES: CN1c2ccccc2C(=O)C[C@@]1(c1ccccc1)C(F)(F)F]

5a, colorless oily solid, 40.1 mg, 66% yield, 95:5 er from 97:3 er of 3a

Analytical data for 5a: $^1H$ NMR (500 MHz, CDCl$_3$) δ 7.88 (dd, J=8.0, 1.8 Hz, 1H), 7.55 (d, J=8.2 Hz, 2H), 7.52-7.48 (m, 1H), 7.46-7.41 (m, 2H), 7.41-7.36 (m, 1H), 6.88-6.82 (m, 2H), 3.26 (d, J=17.0 Hz, 1H), 3.18 (d, J=17.0 Hz, 1H), 2.83 (d, J=1.5 Hz, 3H). $^{13}C\{^1H\}$ NMR (126 MHz, CDCl$_3$) δ 189.7, 150.8, 138.3, 136.3, 129.3, 128.8, 127.2, 127.1 (q, J=294.0 Hz), 126.8, 119.6, 117.9, 113.2, 71.2 (q, J=25.3 Hz), 47.4, 36.2. $^{19}F$ NMR (376 MHz, CDCl$_3$) 5-68.7. LRMS (ESI): Mass calculated for $C_{17}H_{14}F_3NO$ [M+H]: 306.1; found: 306.1; Enantiomeric ratio was measured by chiral phase SFC (Chiralpak IB-3, 2% MeOH in CO$_2$, flow rate=2.5 mL/min, 230 nm): 2.83 min (major), 3.19 min (minor).

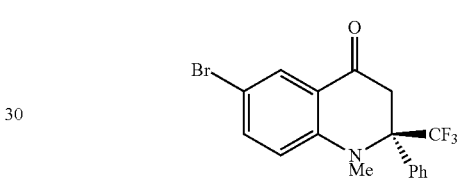

5n, white solid, 46.1 mg, 60% yield, 95:5 er from 95:5 er of 3n

Analytical data for 5n: $^1H$ NMR (500 MHz, CDCl$_3$) δ 7.96 (s, 1H), 7.59-7.50 (m, 3H), 7.48-7.36 (m, 3H), 6.74 (d, J=9.0 Hz, 1H), 3.25 (d, J=17.1 Hz, 1H), 3.18 (d, J=17.1 Hz, 1H), 2.81 (s, 3H). $^{13}C\{^1H\}$ NMR (126 MHz, CDCl$_3$) δ 188.4, 149.6, 138.6, 137.7, 129.5, 129.4, 129.0, 126.9 (q, J=293.8 Hz), 126.8, 120.8, 115.3, 110.6, 71.2 (q, J=25.6 Hz), 47.2, 36.3. $^{19}F$ NMR (376 MHz, CDCl$_3$) δ −68.8. LRMS (ESI): Mass calculated for $C_{17}H_{13}BrF_3NO$ [M+H]: 384.0; found: 384.0; Enantiomeric ratio was measured by chiral phase SFC (Chiralpak IB-3, 5% MeOH in CO$_2$, flow rate=2.5 mL/min, 230 nm): 2.99 min (major), 3.32 min (minor).

Detection of Intermediate II by HRMS-ESI

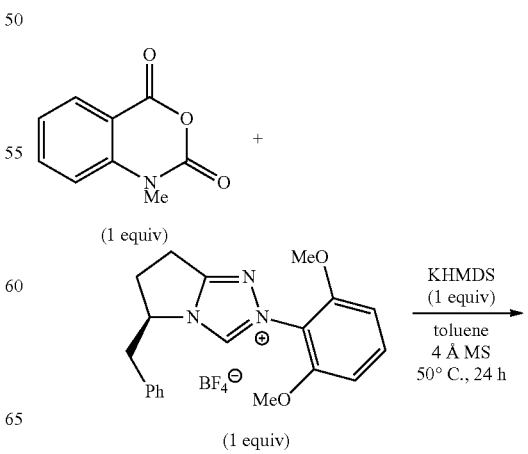

-continued

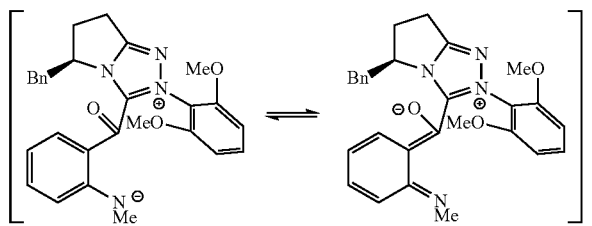

Intermediate II
Chemical Formula: $C_{28}H_{28}N_4O_3$
Exact Mass: 468.2161
Molecular Weight: 468.5570
m/z: 468.2161 (100.0%), 469.2195 (30.3%),
470.2229 (2.7%), 470.2229 (1.7%), 469.2132 (1.5%)
Elemental Analysis: C, 71.78; H, 6.02; N, 11.96; O, 10.24

X-Ray Characterization Data

X-ray quality crystals for (S)-3n were obtained by slow diffusion in $CH_2Cl_2$/hexanes at 23° C.

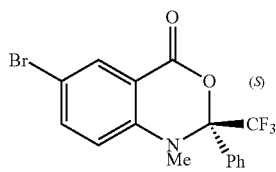

ORTEP representation (50% probability) of the crystal structure (CCDC 1876027).

| Empirical formula | $C_{16}H_{11}BrF_3NO_2$ |
|---|---|
| Formula weight | 386.17 |
| Temperature/K | 99.99 |
| Crystal system | orthorhombic |
| Space group | $P2_12_12_1$ |
| a/Å | 8.0236(8) |
| b/Å | 12.2687(12) |
| c/Å | 14.7137(15) |
| α/° | 90 |
| β/° | 90 |
| γ/° | 90 |
| Volume/Å$^3$ | 1448.4(3) |
| Z | 4 |
| $\rho_{calc}$g/cm$^3$ | 1.771 |
| μ/mm$^{-1}$ | 4.286 |
| F(000) | 768.0 |
| Crystal size/mm$^3$ | 0.265 × 0.166 × 0.054 |
| Radiation | CuKα (λ = 1.54178) |
| 2Θ range for data collection/° | 9.386 to 135.97 |
| Index ranges | −9 ≤ h ≤ 9, −14 ≤ k ≤ 14, −16 ≤ l ≤ 17 |
| Reflections collected | 22744 |
| Independent reflections | 2630 [$R_{int}$ = 0.0285, $R_{sigma}$ = 0.0200] |
| Data/restraints/parameters | 2630/0/209 |
| Goodness-of-fit on F$^2$ | 1.057 |
| Final R indexes [I >= 2σ (I)] | $R_1$ = 0.0158, $wR_2$ = 0.0399 |
| Final R indexes [all data] | $R_1$ = 0.0158, $wR_2$ = 0.0399 |
| Largest diff. peak/hole/e Å$^{-3}$ | 0.29/−0.18 |
| Flack parameter | 0.015(4) |

Figure 12:
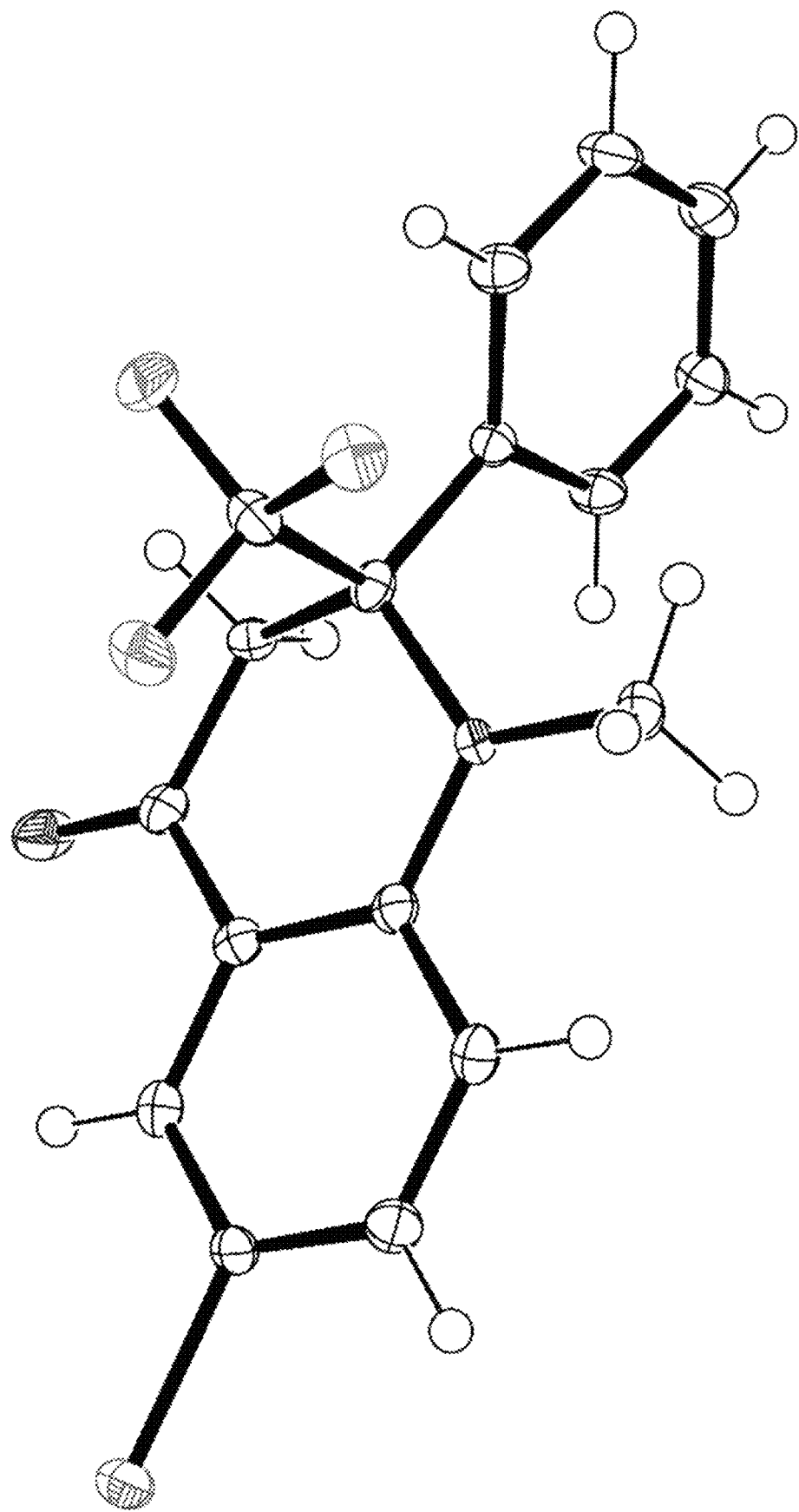
FIG. 12. X-ray crystal structure of 5n.

X-ray quality crystals for (R)-5n were obtained by slow evaporation in pentane at 4° C. See FIG. 12 for the X-ray crystal structure of 5n.

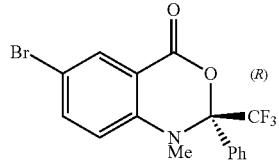

ORTEP representation (50% probability) of the crystal structure (CCDC 1888653).

| Empirical formula | $C_{17}H_{13}BrF_3NO$ |
|---|---|
| Formula weight | 384.19 |
| Temperature/K | 100.0 |
| Crystal system | orthorhombic |
| Space group | $P2_12_12_1$ |
| a/Å | 8.0249(7) |
| b/Å | 12.3902(9) |
| c/Å | 14.8827(12) |
| α/° | 90 |
| β/° | 90 |
| γ/° | 90 |
| Volume/Å$^3$ | 1479.8(2) |
| Z | 4 |
| $\rho_{calc}$g/cm$^3$ | 1.724 |
| μ/mm$^{-1}$ | 2.814 |
| F(000) | 768.0 |
| Crystal size/mm$^3$ | 0.157 × 0.135 × 0.057 |
| Radiation | MoKα (λ = 0.71073) |
| 2Θ range for data collection/° | 4.278 to 61.21 |
| Index ranges | −11 ≤ h ≤ 11, −12 ≤ k ≤ 17, −21 ≤ l ≤ 21 |
| Reflections collected | 22492 |
| Independent reflections | 4533 [$R_{int}$ = 0.0762, $R_{sigma}$ = 0.0644] |
| Data/restraints/parameters | 4533/0/209 |
| Goodness-of-fit on F$^2$ | 1.030 |
| Final R indexes [I >= 2σ (I)] | $R_1$ = 0.0362, $wR_2$ = 0.0667 |
| Final R indexes [all data] | $R_1$ = 0.0494, $wR_2$ = 0.0707 |
| Largest diff. peak/hole/e Å$^{-3}$ | 0.45/−0.40 |
| Flack parameter | 0.005(7) |

Computational Data

Part I: Complete Authorship of Gaussian 09

Gaussian 09, Revision D.01, M. J. Frisch, G. W. Trucks, H. B. Schlegel, G. E. Scuseria, M. A. Robb, J. R. Cheeseman, G. Scalmani, V. Barone, G. A. Petersson, H. Nakatsuji, X. Li, M. Caricato, A. Marenich, J. Bloino, B. G. Janesko, R. Gomperts, B. Mennucci, H. P. Hratchian, J. V. Ortiz, A. F. Izmaylov, J. L. Sonnenberg, D. Williams-Young, F. Ding, F. Lipparini, F. Egidi, J. Goings, B. Peng, A. Petrone, T. Henderson, D. Ranasinghe, V. G. Zakrzewski, J. Gao, N. Rega, G. Zheng, W. Liang, M. Hada, M. Ehara, K. Toyota, R. Fukuda, J. Hasegawa, M. Ishida, T. Nakajima, Y. Honda, O. Kitao, H. Nakai, T. Vreven, K. Throssell, J. A. Montgomery, Jr., J. E. Peralta, F. Ogliaro, M. Bearpark, J. J. Heyd, E. Brothers, K. N. Kudin, V. N. Staroverov, T. Keith, R. Kobayashi, J. Normand, K. Raghavachari, A. Rendell, J. C. Burant, S. S. Iyengar, J. Tomasi, M. Cossi, J. M. Millam, M. Klene, C. Adamo, R. Cammi, J. W. Ochterski, R. L. Martin, K. Morokuma, O. Farkas, J. B. Foresman, and D. J. Fox, Gaussian, Inc., Wallingford Conn., 2016.

Part II: General Computational Procedure

Manual, exhaustive conformation searches were performed to locate all relevant structures. All conformers were optimized using the Gaussian 09 suite of programs (see above reference) using PBE/6-31G(d) in the gas phase, unless noted otherwise. Stationary points were confirmed with vibrational frequency computations, with ground states having zero imaginary frequencies, and transition states having one imaginary vibrational frequency. Solvation corrections were obtained at the PBE/6-31G(d) level of theory using SMD (Solvation Model based on Density) for toluene. Single point corrections were computed at ωB97X/6-311++G(2df, p) level of theory. Additionally, the referees requested the optimizations of these structures using DFT methods that include dispersion. We therefore optimized these structures using ωB97XD/6-31G(d)/SMD(Toluene) at 323 K. Final free energies were calculated by adding the solvation and thermal corrections to the gas phase electronic energies.

Computed structures were rendered in CYLview visualization software: C. Y. Legault, CYLview, 1.0b. Université de Sherbrooke; 2009.

Part III: Conformational Analysis

Figure 3:
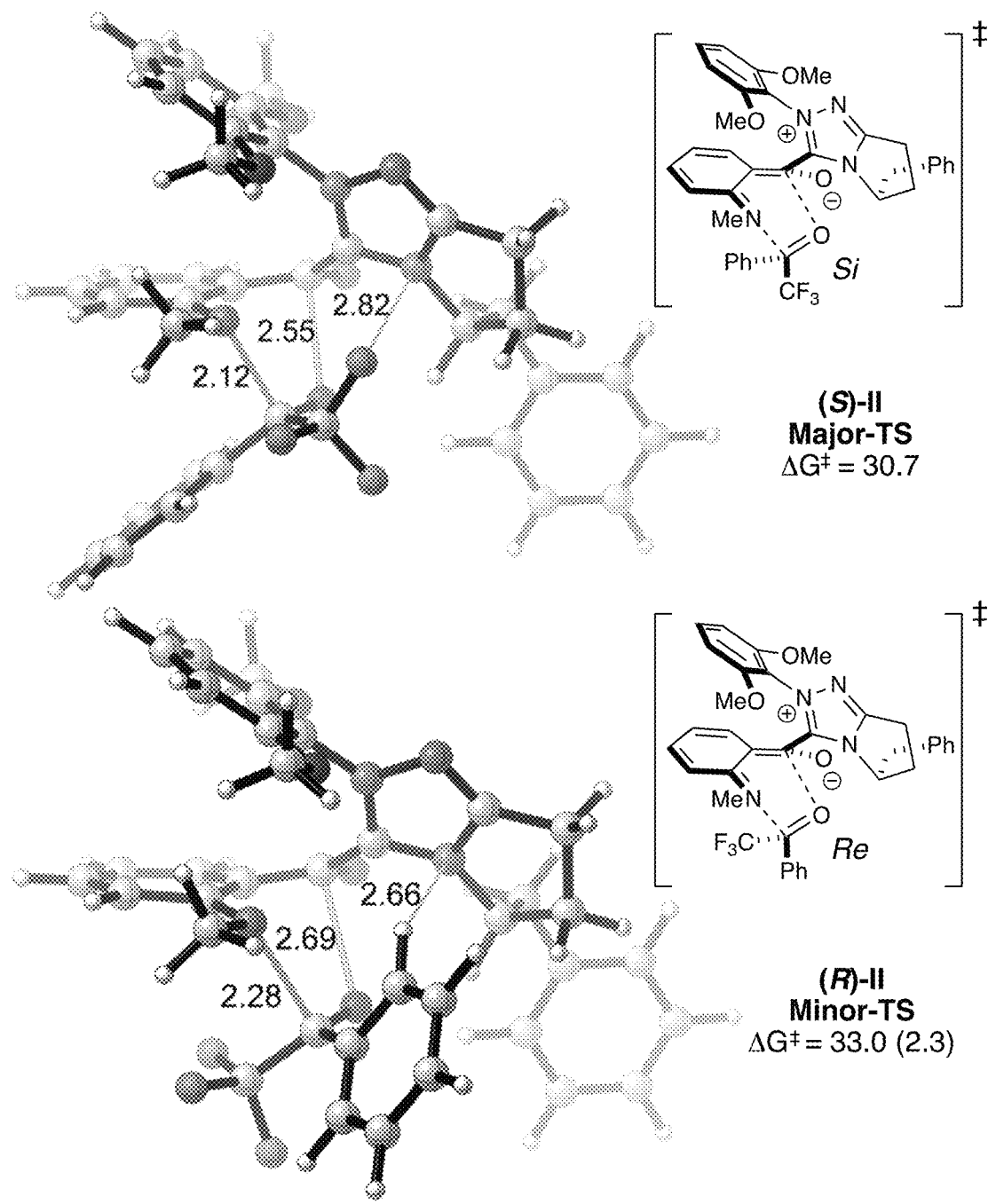
FIG. 3. DFT major and minor [4+2] cycloaddition transition structures. Structures were optimized using PBE/6-31G(d) in gas phase. With solvation corrections obtained using SMD in toluene. Single-point corrections were calculated using ωB97X/6-311++G(2df,p)/SMD (Toluene). Distances in Å and energies in kcal/mol.
Figure 4:
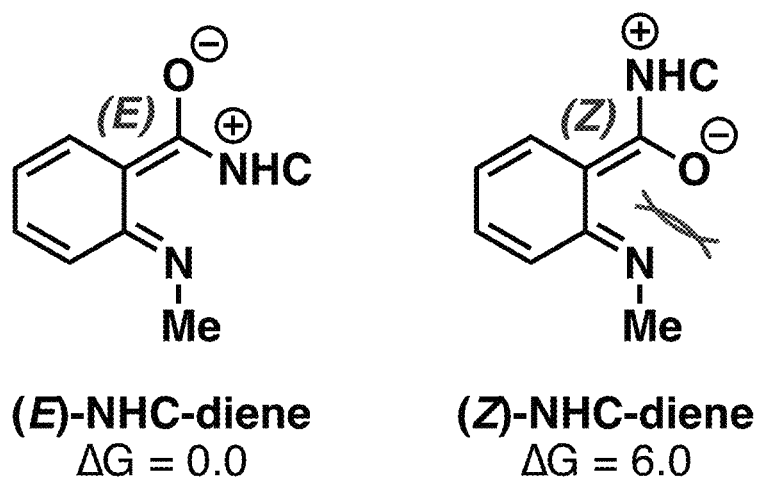
FIG. 4. (E)- vs (Z)-NHC-diene preference. The (Z)-isomer is likely disfavored due to electrostatic repulsion between the lone pairs on the anionic oxygen and the ortho-quinone methide nitrogen.

We manually constructed and examined different conformations of the transition state (TS) structure for this reaction. (FIG. 3) Taking into consideration restrictions that arise from forming and breaking bonds in the TS, we have discovered that the TS can only accommodate a few conformations that avoid steric interactions and electrostatic repulsion. The NHC-diene complex prefers the (E)-isomer by 6.0 kcal/mol over the (Z)-isomer (FIG. 4). This preference is likely due to the electrostatic repulsion between the lone pairs on the anionic oxygen and those on the ortho-quinone methide nitrogen.

Figure 5:
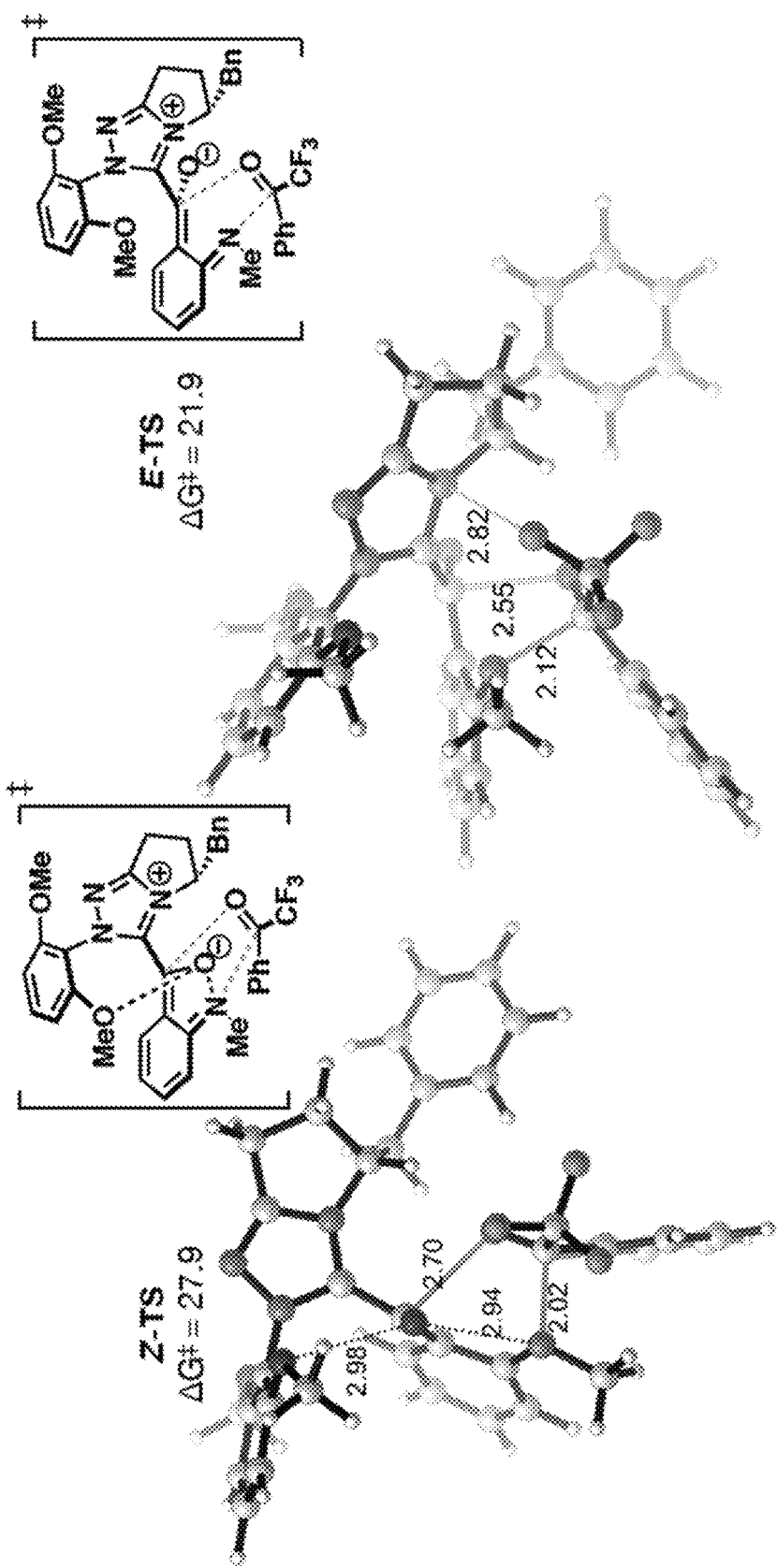
FIG. 5. The NHC-diene (Z)-configuration is disfavored (left) over the (K)-configuration (right) due to two destabilizing electrostatic repulsion interactions (dotted lines). Distances are in Ångströms and energies are in kcal/mol.

The NHC-dienes in the major and minor transition states adopt the lower-energy (E)-configuration (vide supra, FIG. 2). (Z)-configuration transition states were located, but were always higher in energy. The lowest energy (Z)-configuration transition state is shown in FIG. 5. In this structure, there are two destabilizing interactions shown as dotted lines that do not manifest in the (E)-configuration: 1) O . . . O electrostatic repulsion (2.98 Å); 2) N . . . O electrostatic repulsion (2.94 Å).

Part IV: Origins of Stereoselectivity (Distortion Interaction Analysis[5])

Figure 6:
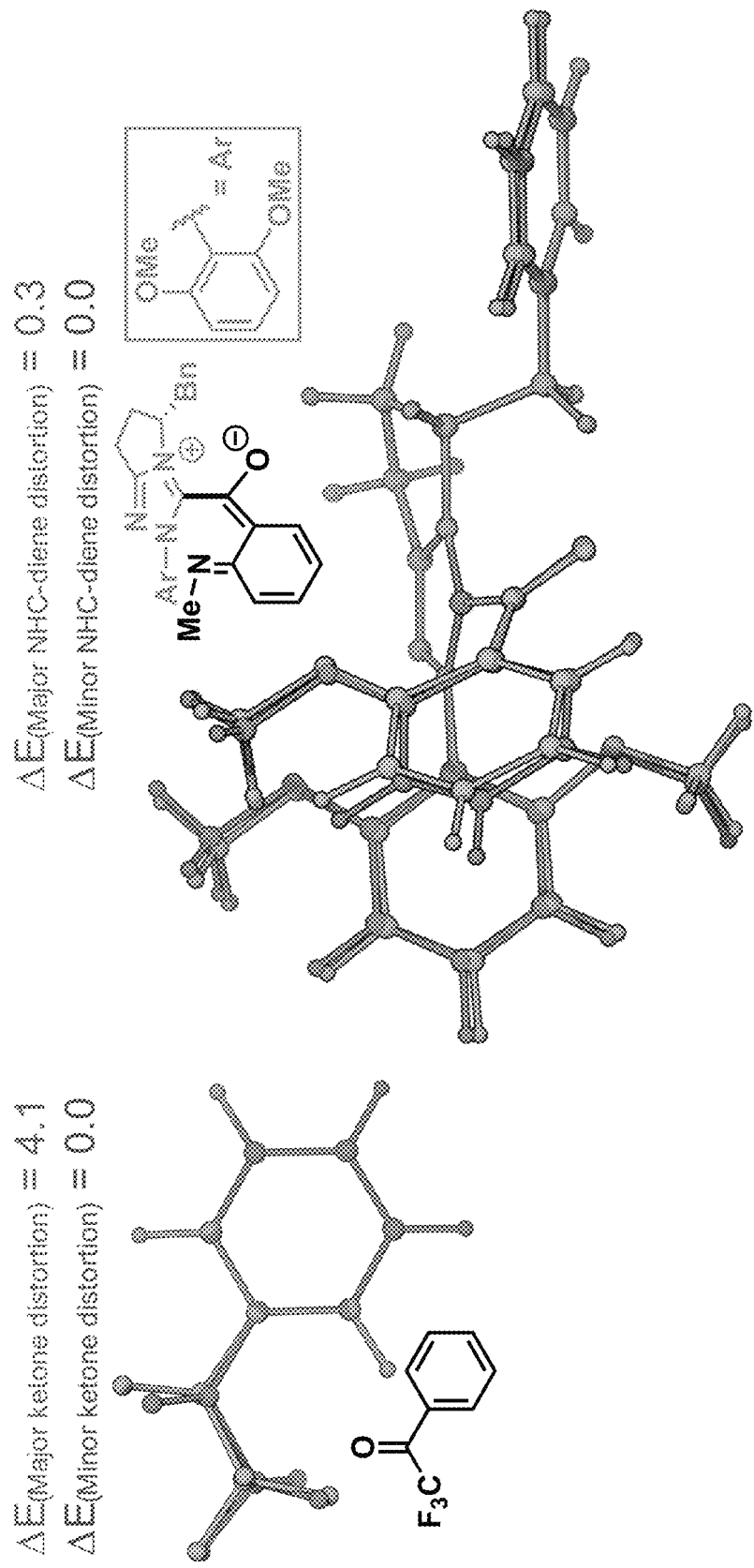
FIG. 6. Overlay of Major-TS (green) and Minor-TS (red) trifluoromethyl ketone (left) and NHC-diene complex (right). Energies are in kcal/mol.

Distortion energies: Gas phase electronic energies with single point energy corrections were used to calculate distortion energies from the ground state to the transition state conformations. The trifluoromethyl ketone distortion for the Major-TS was 15.3 kcal/mol and was 11.2 kcal/mol for the Minor-TS (ΔE=4.1 kcal/mol). The trifluoromethyl ketones were overlaid for visual inspection (FIG. 6, left; Major-TS=green and Minor-TS=red). The major visual difference lies in the trifluoroacetyl group.

The NHC-diene distortion energy for the Major-TS was 24.9 kcal/mol and 24.6 kcal/mol for the Minor-TS (ΔE=0.3 kcal/mol). The NHC-dienes were also overlaid to visually inspect the difference in conformation (FIG. 6, right; Major-TS=green and Minor-TS=red). The major visual difference lies in the aza-ortho-quinone methide.

Distortion energies that were calculated using ωB97XD/6-31G(d) resulted in the same trend. The trifluoromethyl ketone distortion for the Major-TS was 8.0 kcal/mol and was 6.2 kcal/mol for the Minor-TS (ΔE=1.8 kcal/mol). The NHC-diene distortion energy for the Major-TS was 30.8 kcal/mol and 31.8 kcal/mol for the Minor-TS (AE=1.0 kcal/mol).

Figure 7:
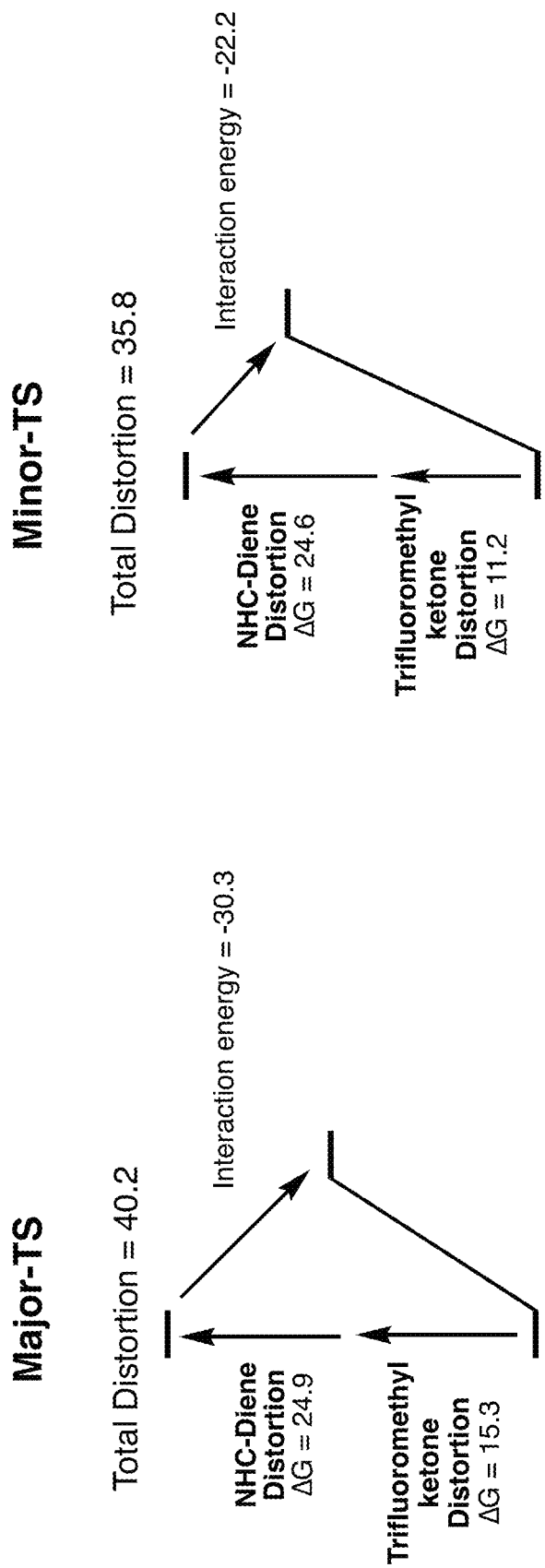
FIG. 7. Distortion and interaction barriers for the Major- and the Minor-TSs. Energies are in kcal/mol.

Interaction energies: The difference in distortion energies for both the Major- and Minor-TSs was 4.4 kcal/mol (vide supra), but the difference in interaction energies was much larger, 8.1 kcal/mol. This suggests that the origin of selectivity arises from the interaction between the trifluoromethyl ketone and the NHC-diene (FIG. 7).

When ωB97XD/6-31G(d) was used the difference in distortion energies for both the Major- and Minor-TSs was 0.8 kcal/mol (vide supra), but the difference in interaction energies was 5.7 kcal/mol (interaction energy for the Major-TS is –33.6 kcal/mol and is –27.9 kcal/mol for the Minor-TS).

Trifluoromethyl Ketone Analysis

Figure 8:
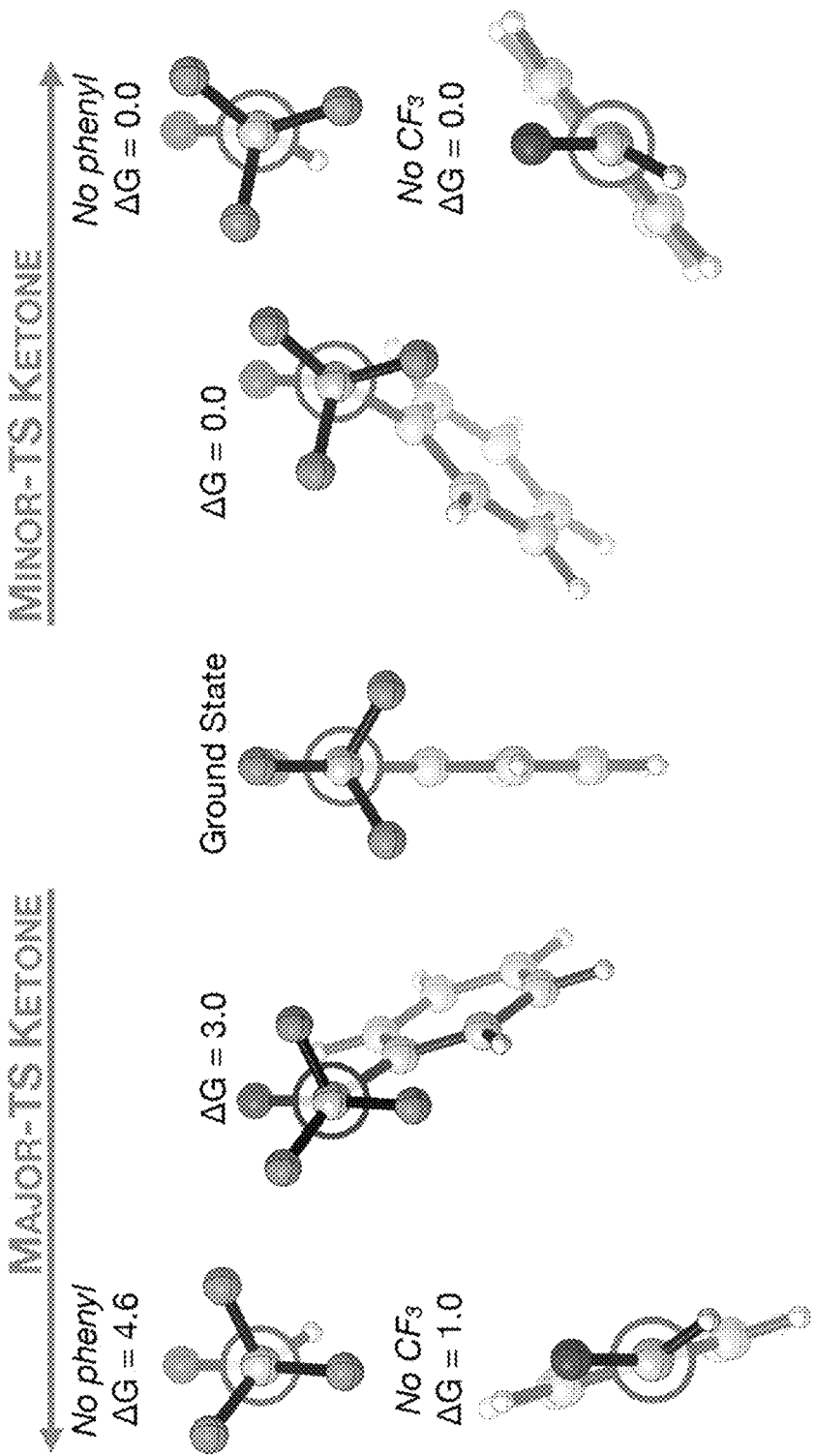
FIG. 8. Different conformation of the ketone substrate. Energies are reported in kcal/mol.

FIG. 8 shows the trifluoromethyl ketone structures in the Major- and Minor-TSs as well as model systems that reflect the substituent geometries. The trifluoromethyl ketone in the Major-TS is more distorted because the trifluoromethyl group is bisected by the carbonyl rather than the favored eclipsed conformation. The phenyl is only slightly more distorted in the Major-TS, presumably again due to the staggered conformation rather than the favored eclipsed conformation.

Potential Energy Surface Plots

Figure 9:
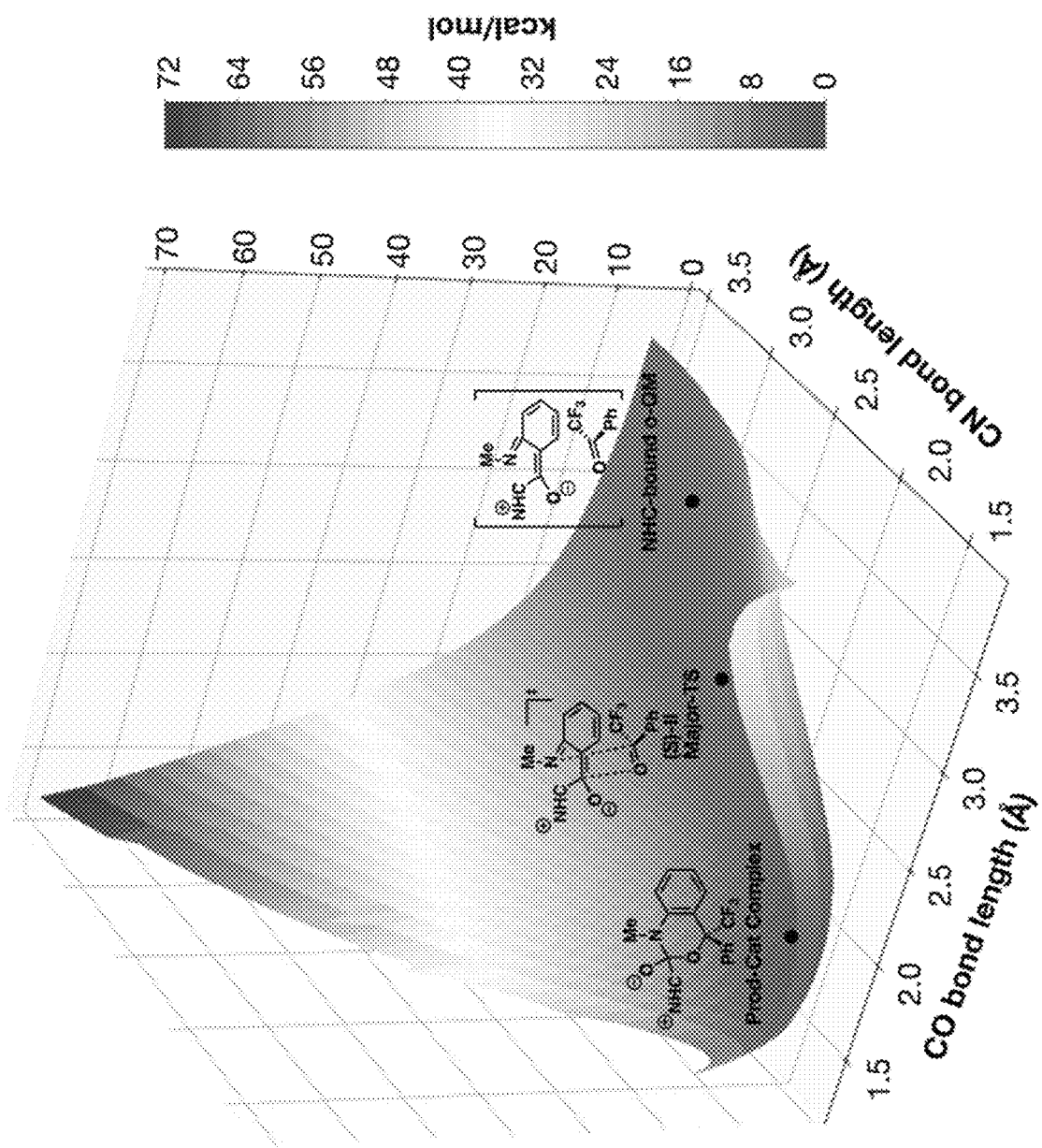
FIG. 9. Potential energy surface plot for conversion of the ketone and NHC-bound o-QM to the Prod-Cat Complex through the (S)-II Major-TS. Energies are in kcal/mol and distances are in Ångströms.
Figure 10:
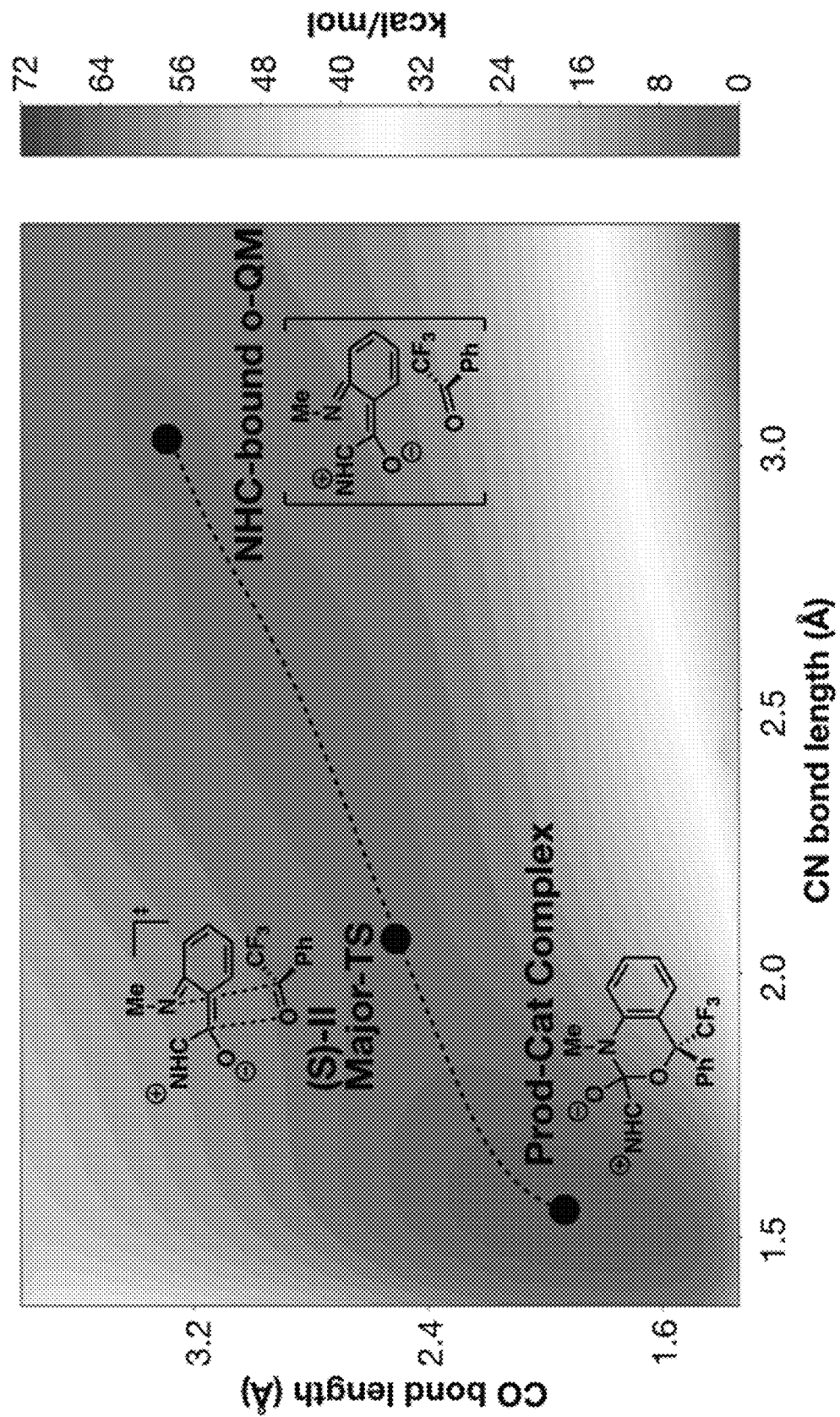
FIG. 10. Two dimensional potential energy surface plot for conversion of the ketone and NHC-bound o-QM to the Prod-Cat Complex through the (S)-II Major-TS. Energies are in kcal/mol and distances are in Angstroms.

The potential energy surface is shown in FIG. 9. A two dimensional version is presented in FIG. 10. These plots were generated using PBE/6-31G(d) with (S)-II Major-TS used as the starting point. The energies were calculated by fixing the distance between the nucleophilic nitrogen of the NHC-bound o-QM and the electrophilic carbon of the ketone (CN bond, x-axis) and varying distances corresponding to the second forming bond (CO bond, y-axis). The associated energies at each of the 2100 data points are plotted on the z-axis in kcal/mol.

References for Example II

1. Pangborn, A. B.; Giardello, M. A.; Grubbs, R. H.; Rosen, R. K.; Timmers F. J. *Organometallics* 1996, 15, 1518-1520.
2. Wurz, N. E.; Daniliuc, C. G.; Glorius, F. *Chem. Eur. J.* 2012, 18, 16297-16301.
3. Bose, D. S.; Chary, M. V. *Synthesis* 2010, 4, 643-650.
4. Beutner, G. L.; Kuethe, J. T.; Yasuda, N. *J. Org. Chem.* 2007, 72, 7058-7061.
5. Chen, S.; Zheng, Y.; Cui, T.; Meggers, E.; Houk, K. N. *J. Am. Chem. Soc.* 2018, 140, 5146-5152.
6. PBE: J. P. Perdew, K. Burke and M. Ernzerhof, *Physical Review Letters*, 1996, 77, 3865-3868
7. 6-31G(d): W. J. Hehre, R. Ditchfield and J. A. Pople, *J. Chem. Phys.*, 1972, 56, 2257-2261
8. SMD: A. V. Marenich, C. J. Cramer and D. G. Truhlar, *J. Phys. Chem.*, 2009, 113, 6378-6396
9. ωB97X: J. Chai and M. Head-Gordon, *J. Chem. Phys.*, 2008, 128, 084106
10. ωB97XD: J. Chai and M. Head-Gordon, *J. Chem. Phys.*, 2008, 10, 6615-6620
11. 6-311++G(2df, p): J. R. Cheeseman, G. W. Trucks, T. A. Keith and J. Frisch, *J. Chem. Phys.*, 1996, 104, 5497-5509.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A compound of the following formula or a salt or hydrate thereof:

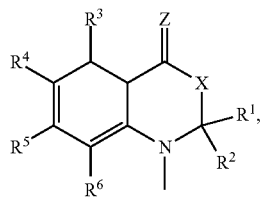

wherein:
R$^1$ is selected from alkyl, alkoxy, carboxyalkyl, haloalkyl, and amino;
R$^2$ is selected from cycloalkyl, aryl, heteroaryl, which optionally is substituted at one or more positions with a substituent selected from alkyl, alkoxy, halo, haloalkyl, and amino;
R$^3$, R$^4$, R$^5$, and R$^6$ are independently selected from hydrogen, alkyl, alkoxy, halo, haloalkyl, and amino;
X is selected from O and CH$_2$; and
Z is selected from O and CH$_2$.

2. The compound of claim 1, wherein R$^1$ is trifluoroalkyl.
3. The compound of claim 1, wherein R$^2$ is phenyl.
4. The compound of claim 1, wherein R$^2$ is thiophene.
5. The compound of claim 1, wherein R$^2$ is aryl substituted at one more positions with a substituent selected from alkyl, alkoxy, halo, and haloalkyl.
6. The compound of claim 5, wherein R$^2$ is ortho-substituted, meta-substituted, di-meta-substituted, or para-substituted.
7. The compound of claim 1, wherein at least one of R$^3$, R$^4$, R$^5$, and R$^6$ is bromo.
8. The compound of claim 1, wherein at least one of R$^3$, R$^4$, R$^5$, and R$^6$ is fluoro.
9. The compound of claim 1, wherein at least one of R$^3$, R$^4$, R$^5$, and R$^6$, is chloro.
10. The compound of claim 1, wherein at least one of R$^3$, R$^4$, R$^5$, and R$^6$ is methoxy.
11. The compound of claim 1, wherein at least one of R$^3$, R$^4$, R$^5$, and R$^6$ is methyl.
12. The compound of claim 1, wherein R$^3$ is hydrogen.
13. The compound of claim 1, wherein R$^6$ is hydrogen.
14. The compound of claim 1, having a formula:

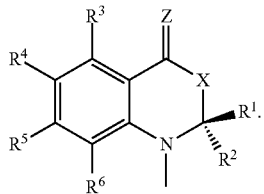

15. The compound of claim 1, wherein the compound has a formula selected from the group consisting of:

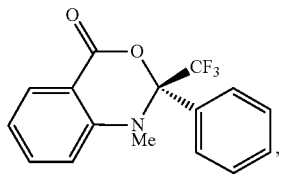

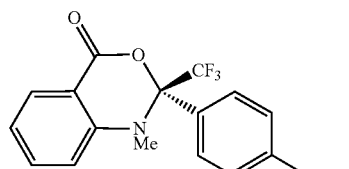

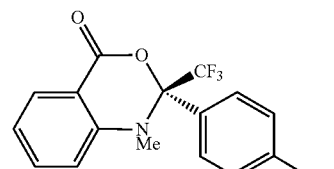

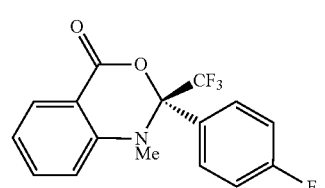

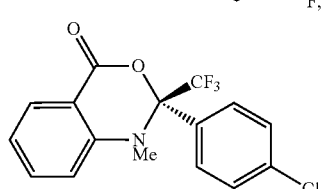

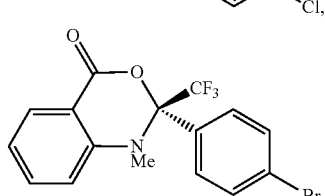

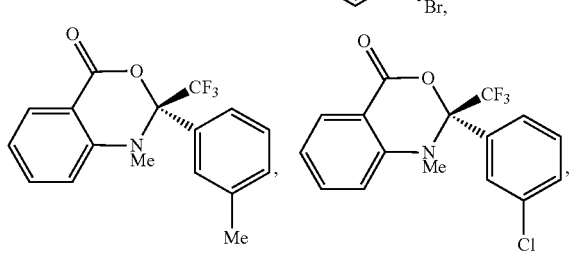

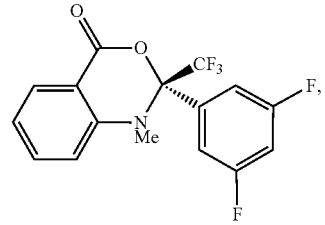

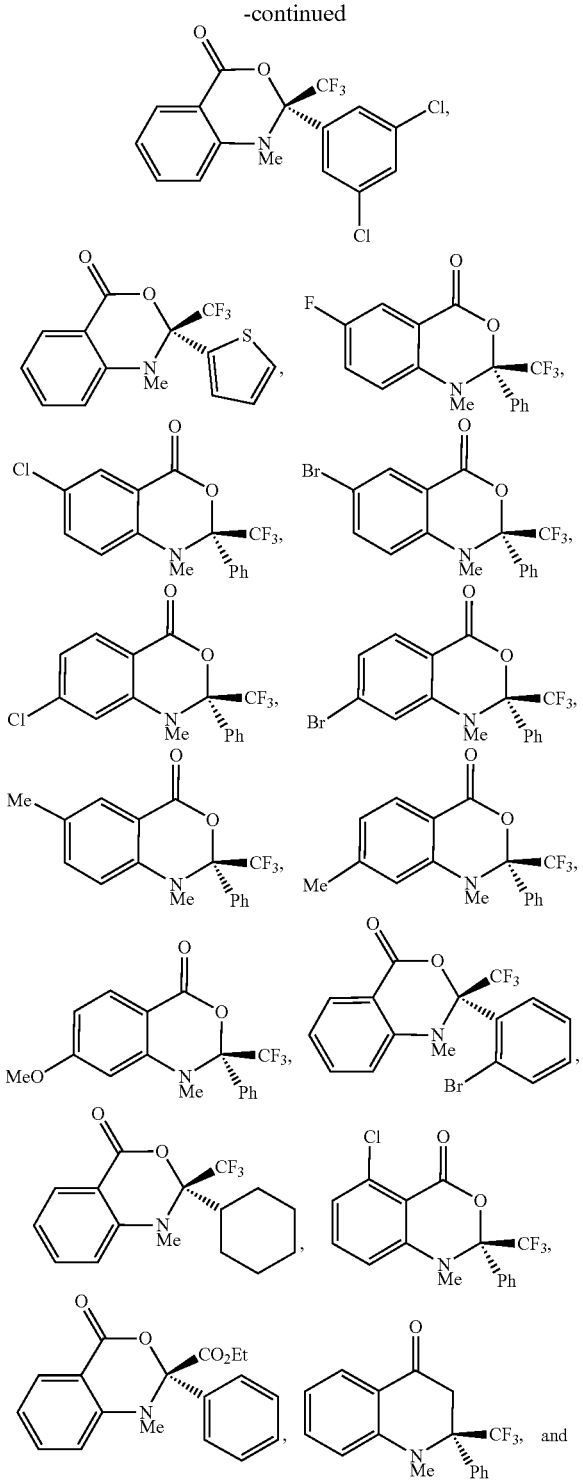

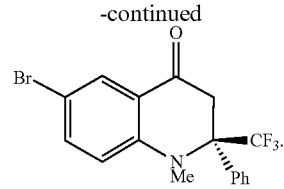

16. An enantiomerically pure composition comprising the compound of claim 1.

17. A racemic mixture of compounds comprising the compound of claim 1,
wherein the compound represents at least about 80%, 85%, 90%, 95%, 96%, 97%, 98%, or 99% of the racemic mixture of compounds.

18. A pharmaceutical composition comprising: (a) an effective amount of the compound of claim 1; and (b) at least one of a carrier, excipient, or diluent.

19. A method of synthesizing any of the compounds of claim 1, the method comprising reacting:
(a) a compound of a formula

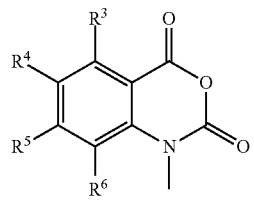

wherein:
$R^3$, $R^4$, $R^5$, and $R^6$ are independently selected from hydrogen, alkyl, alkoxy, halo, haloalkyl, and amino; and (b) a compound of a formula

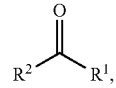

wherein:
$R^1$ is selected from alkyl, carboxyalkyl, and haloalkyl;
$R^2$ is selected from cycloalkyl, aryl, and heteroaryl, which optionally is substituted at one or more positions with a substituent selected from alkyl, alkoxy, halo, haloalkyl, and amino; wherein the compound (a) and the compound (b) are reacted in the presence of an N-heterocyclic carbene (NHC) catalyst to perform a NHC-catalyzed decarboxylative cycloaddition.

* * * * *